US010111688B2

(12) United States Patent
Raven, III et al.

(10) Patent No.: US 10,111,688 B2
(45) Date of Patent: Oct. 30, 2018

(54) SYSTEM FOR TREATING BONE FRACTURES

(71) Applicant: McGinley Engineered Solutions, LLC, Casper, WY (US)

(72) Inventors: Raymond B. Raven, III, Pasadena, CA (US); Dan A. Zlotolow, Wyndmoor, PA (US)

(73) Assignee: McGinley Engineered Solutions, LLC, Casper, WY (US)

( * ) Notice: Subject to any disclaimer, the term of this patent is extended or adjusted under 35 U.S.C. 154(b) by 0 days.

(21) Appl. No.: 15/595,580

(22) Filed: May 15, 2017

(65) Prior Publication Data

US 2018/0055548 A1 Mar. 1, 2018

Related U.S. Application Data

(60) Continuation of application No. 13/957,677, filed on Aug. 2, 2013, now Pat. No. 9,649,141, which is a division of application No. 13/101,483, filed on May 5, 2011, now Pat. No. 8,603,148.

(60) Provisional application No. 61/405,822, filed on Oct. 22, 2010, provisional application No. 61/332,439, filed on May 7, 2010.

(51) Int. Cl.
*A61B 17/56* (2006.01)
*A61B 17/80* (2006.01)

(52) U.S. Cl.
CPC .............. *A61B 17/56* (2013.01); *A61B 17/80* (2013.01); *A61B 17/8004* (2013.01); *A61B 17/809* (2013.01); *A61B 17/8061* (2013.01); *A61B 17/8052* (2013.01); *A61B 2017/564* (2013.01)

(58) Field of Classification Search
CPC ... A61B 17/56; A61B 2017/564; A61B 17/80; A61B 17/8004; A61B 17/8052; A61B 17/8061; A61B 17/809
See application file for complete search history.

(56) References Cited

U.S. PATENT DOCUMENTS

| | | |
|---|---|---|
| 2,561,550 A | 7/1951 | Wright |
| 4,651,724 A | 3/1987 | Berentey |
| 4,683,878 A | 8/1987 | Carter |
| 5,006,120 A | 4/1991 | Carter |
| 5,197,966 A | 3/1993 | Sommerkamp |
| 5,586,985 A | 12/1996 | Putnam et al. |
| 5,662,649 A | 9/1997 | Huebner |
| 5,709,682 A | 1/1998 | Medoff |
| 5,718,704 A | 2/1998 | Medoff |
| 5,853,413 A | 12/1998 | Carter et al. |

(Continued)

FOREIGN PATENT DOCUMENTS

| | | | |
|---|---|---|---|
| FR | 2650500 | 2/1991 | |
| FR | 2650500 A1 * | 2/1991 | ........... A61B 17/746 |

(Continued)

*Primary Examiner* — Larry E. Waggle, Jr.
(74) *Attorney, Agent, or Firm* — Marsh Fischmann & Breyfogle LLP

(57) ABSTRACT

According to one embodiment, a bone fixation system includes a plate having a first opening a beam configured to traverse through the first opening and reside proximate to a subchondral fragment of bone in an installed position. The beam may be operable to rotate about an axis of rotation proximate to the first opening and reposition the subchondral fragment of bone.

3 Claims, 42 Drawing Sheets

(56) References Cited

U.S. PATENT DOCUMENTS

| | | |
|---|---|---|
| 5,931,839 A | 8/1999 | Medoff |
| 5,935,128 A | 8/1999 | Carter et al. |
| 5,941,878 A | 8/1999 | Medoff |
| 6,001,099 A | 12/1999 | Huebner |
| 6,007,536 A | 12/1999 | Yue |
| 6,096,040 A | 8/2000 | Esser |
| 6,123,704 A | 9/2000 | Hajianpour |
| 6,183,475 B1 * | 2/2001 | Lester ............... A61B 17/8095 606/281 |
| 6,197,027 B1 | 3/2001 | Hajianpour |
| 6,221,073 B1 | 4/2001 | Weiss |
| 6,283,969 B1 | 9/2001 | Grusin |
| 6,355,042 B2 | 3/2002 | Winquist et al. |
| 6,358,250 B1 | 3/2002 | Orbay |
| 6,364,882 B1 | 4/2002 | Orbay |
| 6,379,359 B1 | 4/2002 | Dahners |
| 6,440,135 B2 | 8/2002 | Orbay et al. |
| 6,508,819 B1 | 1/2003 | Orbay |
| 6,585,736 B2 | 7/2003 | Haijanpour |
| 6,629,976 B1 | 10/2003 | Gnos et al. |
| 6,635,059 B2 | 10/2003 | Randall et al. |
| 6,702,817 B2 | 3/2004 | Beger et al. |
| 6,706,046 B2 | 3/2004 | Orbay et al. |
| 6,712,820 B2 | 3/2004 | Orbay |
| 6,730,090 B2 | 5/2004 | Orbay et al. |
| 6,755,831 B2 | 6/2004 | Putnam et al. |
| 6,767,351 B2 | 7/2004 | Orbay et al. |
| 6,866,665 B2 | 3/2005 | Orbay |
| 6,893,444 B2 | 5/2005 | Orbay |
| 6,926,720 B2 | 8/2005 | Casteneda |
| 7,001,388 B2 | 2/2006 | Orbay et al. |
| 7,090,676 B2 | 8/2006 | Huebner |
| 7,137,987 B2 | 11/2006 | Patterson et al. |
| 7,153,309 B2 | 12/2006 | Huebner et al. |
| 7,160,302 B2 | 1/2007 | Warburton |
| 7,189,237 B2 | 3/2007 | Huebner |
| 7,195,633 B2 | 3/2007 | Medoff |
| 7,229,445 B2 * | 6/2007 | Hayeck ............... A61B 17/74 606/70 |
| 7,250,053 B2 * | 7/2007 | Orbay ............... A61B 17/8057 606/291 |
| 7,267,678 B2 | 9/2007 | Medoff |
| 7,282,053 B2 | 10/2007 | Orbay |
| 7,294,130 B2 | 11/2007 | Orbay |
| 7,299,561 B2 | 11/2007 | Castenda |
| 7,316,687 B2 | 1/2008 | Aikens et al. |
| 7,341,589 B2 | 3/2008 | Weaver et al. |
| 7,367,977 B2 | 5/2008 | Estada, Jr. |
| 7,527,639 B2 | 5/2009 | Orbay et al. |
| 7,537,596 B2 | 5/2009 | Jensen |
| 7,537,604 B2 | 5/2009 | Huebner |
| 7,578,825 B2 | 8/2009 | Huebner |
| 7,588,577 B2 | 9/2009 | Fencl et al. |
| 7,603,192 B2 | 10/2009 | Martin et al. |
| 7,604,657 B2 | 10/2009 | Orbay et al. |
| 7,635,381 B2 | 12/2009 | Orbay |
| 7,648,508 B2 | 1/2010 | Lutz et al. |
| 7,686,808 B2 | 3/2010 | Orbay et al. |
| 7,695,502 B2 | 4/2010 | Orbay et al. |
| 7,719,260 B2 | 5/2010 | Uchida et al. |
| 7,727,264 B2 | 6/2010 | Orbay et al. |
| 7,740,634 B2 | 6/2010 | Orbay |
| 7,771,433 B2 | 8/2010 | Orbay et al. |
| 7,771,457 B2 | 8/2010 | Kay et al. |
| 7,780,711 B2 | 8/2010 | Orbay et al. |
| 7,799,061 B2 | 9/2010 | Kay et al. |
| 7,857,838 B2 | 12/2010 | Orbay |
| 7,867,260 B2 | 1/2011 | Meyer |
| 7,887,569 B2 | 2/2011 | Frigg |
| 7,905,909 B2 | 3/2011 | Orbay |
| 7,951,176 B2 | 5/2011 | Grady, Jr. |
| 7,951,178 B2 | 5/2011 | Jensen |
| 8,021,402 B2 | 9/2011 | Martin |
| 8,043,297 B2 | 10/2011 | Grady, Jr. |
| 8,062,296 B2 | 11/2011 | Orbay |
| 8,100,952 B2 | 1/2012 | Matityahu |
| 8,114,081 B2 | 2/2012 | Kohut |
| 8,147,530 B2 | 4/2012 | Strnad |
| 8,172,886 B2 | 5/2012 | Castaneda |
| 8,394,098 B2 | 3/2013 | Orbay |
| 8,394,130 B2 | 3/2013 | Orbay, Jr. |
| 8,579,899 B2 | 11/2013 | Ahmadi |
| 8,603,148 B2 | 12/2013 | Raven, III |
| 8,926,675 B2 | 1/2015 | Leung |
| 2003/0040748 A1 * | 2/2003 | Aikins ............... A61B 17/1668 606/70 |
| 2003/0153918 A1 | 8/2003 | Putnam |
| 2004/0102775 A1 | 5/2004 | Huebner |
| 2004/0111090 A1 | 6/2004 | Dahners |
| 2004/0153073 A1 | 8/2004 | Orbay |
| 2004/0193155 A1 | 9/2004 | Castenda |
| 2004/0193164 A1 | 9/2004 | Orbay |
| 2004/0193165 A1 | 9/2004 | Orbay |
| 2004/0220570 A1 | 11/2004 | Frigg |
| 2004/0260291 A1 | 12/2004 | Jensen |
| 2004/0260292 A1 | 12/2004 | Orbay |
| 2004/0260293 A1 | 12/2004 | Orbay et al. |
| 2004/0260294 A1 | 12/2004 | Orbay |
| 2004/0260295 A1 | 12/2004 | Orbay et al. |
| 2005/0010226 A1 | 1/2005 | Grady, Jr. |
| 2005/0065522 A1 | 3/2005 | Orbay |
| 2005/0065523 A1 | 3/2005 | Orbay |
| 2005/0065524 A1 | 3/2005 | Orbay |
| 2005/0085818 A1 | 4/2005 | Huebner |
| 2005/0107795 A1 | 5/2005 | Morris et al. |
| 2005/0143736 A1 | 6/2005 | deFrota Carrera |
| 2005/0154392 A1 | 7/2005 | Medoff |
| 2005/0159747 A1 | 7/2005 | Orbay |
| 2005/0171544 A1 | 8/2005 | Falkner, Jr. |
| 2005/0234458 A1 | 10/2005 | Huebner |
| 2005/0240186 A1 | 10/2005 | Orbay |
| 2006/0009771 A1 | 1/2006 | Orbay |
| 2006/0015101 A1 | 1/2006 | Warburton et al. |
| 2006/0041260 A1 | 2/2006 | Orbay |
| 2006/0089648 A1 | 4/2006 | Masini |
| 2006/0095044 A1 | 5/2006 | Grady, Jr. |
| 2006/0100624 A1 | 5/2006 | Orbay |
| 2006/0116679 A1 | 6/2006 | Lutz |
| 2006/0149250 A1 | 7/2006 | Castaneda |
| 2006/0161156 A1 | 7/2006 | Orbay et al. |
| 2006/0161158 A1 | 7/2006 | Orbay |
| 2006/0173458 A1 | 8/2006 | Forstein et al. |
| 2006/0200145 A1 | 9/2006 | Kay |
| 2006/0200151 A1 | 9/2006 | Ducharme et al. |
| 2006/0229619 A1 | 10/2006 | Orbay |
| 2006/0235404 A1 | 10/2006 | Orbay |
| 2006/0259039 A1 | 11/2006 | Pitkanen et al. |
| 2006/0264949 A1 | 11/2006 | Kohut |
| 2007/0043366 A1 | 2/2007 | Pfefferle et al. |
| 2007/0055253 A1 | 3/2007 | Orbay |
| 2007/0083202 A1 | 4/2007 | Eli Running et al. |
| 2007/0088360 A1 | 4/2007 | Orbay |
| 2007/0123886 A1 | 5/2007 | Meyer |
| 2007/0173843 A1 | 7/2007 | Matityahu |
| 2007/0212915 A1 | 9/2007 | Strnad |
| 2007/0233112 A1 | 10/2007 | Orbay |
| 2007/0265629 A1 | 11/2007 | Martin |
| 2007/0270853 A1 | 11/2007 | Leung |
| 2008/0021477 A1 | 1/2008 | Strnad et al. |
| 2008/0027439 A1 | 1/2008 | Sasing |
| 2008/0051786 A1 | 2/2008 | Jensen |
| 2008/0091198 A1 | 4/2008 | Libel et al. |
| 2009/0062862 A1 | 3/2009 | Perrow |
| 2009/0228047 A1 | 9/2009 | Derouet et al. |
| 2009/0234359 A1 | 9/2009 | Onoue et al. |
| 2012/0203228 A1 | 8/2012 | Raven, III |

FOREIGN PATENT DOCUMENTS

| | | |
|---|---|---|
| JP | 03930812 | 5/2004 |
| JP | 2007190115 | 8/2007 |
| JP | 2008206789 | 9/2008 |

* cited by examiner

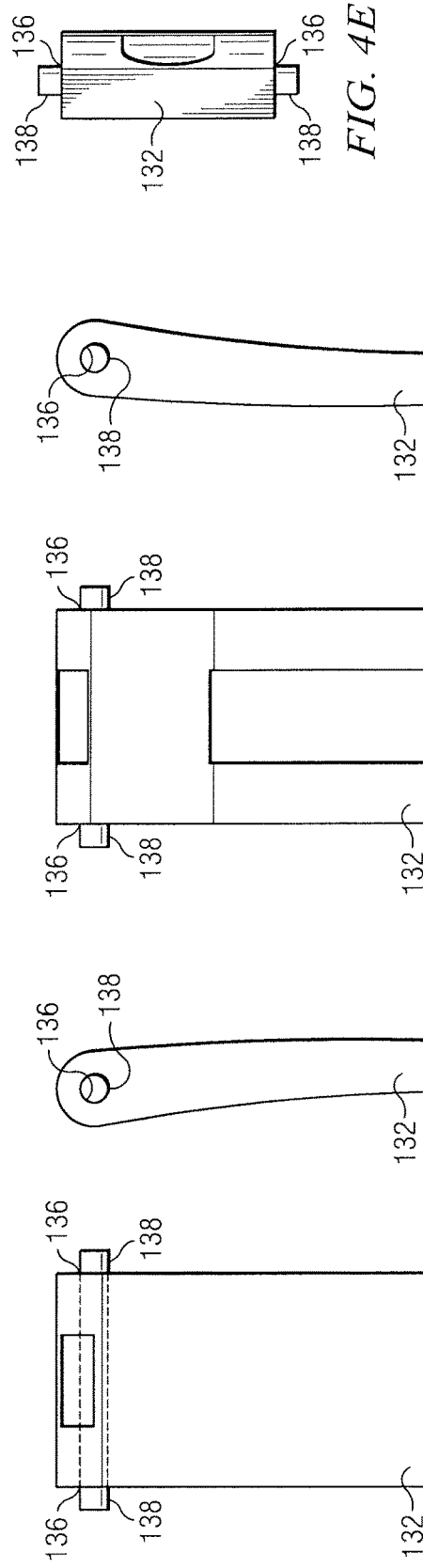

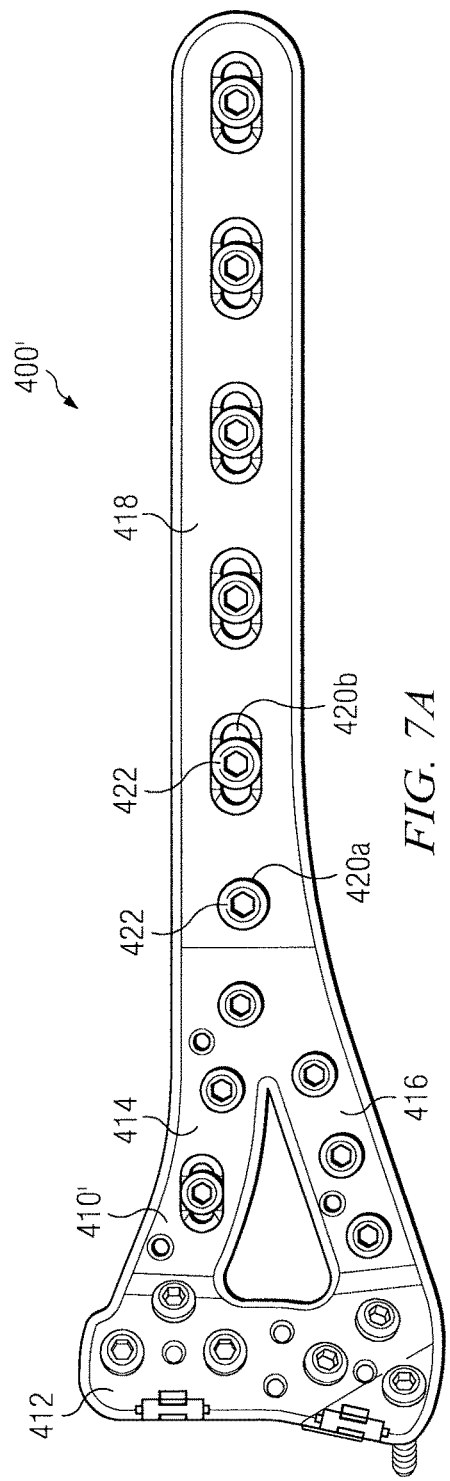
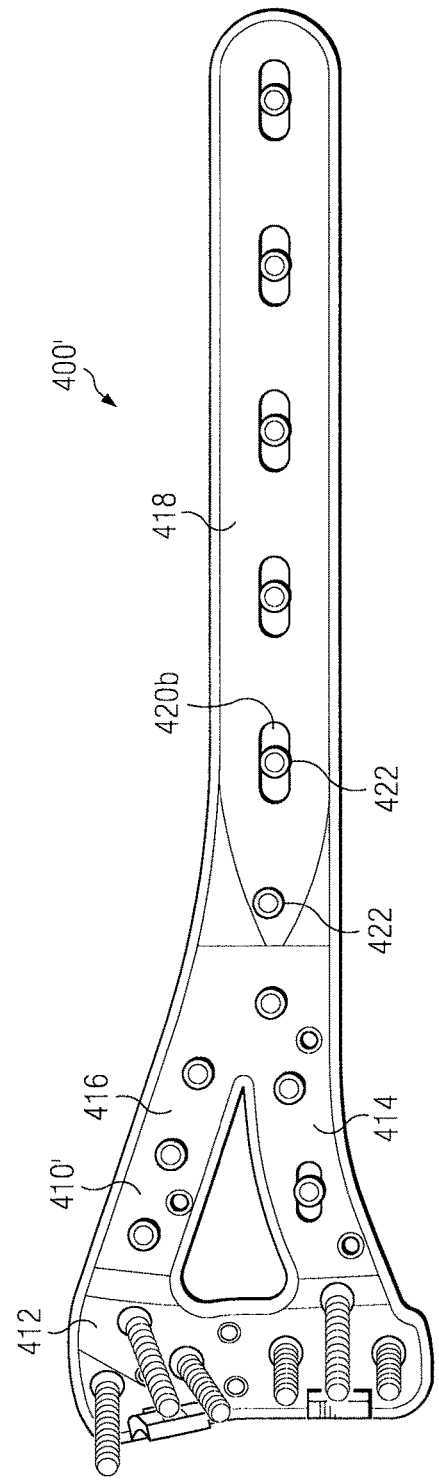
FIG. 7A
FIG. 7B

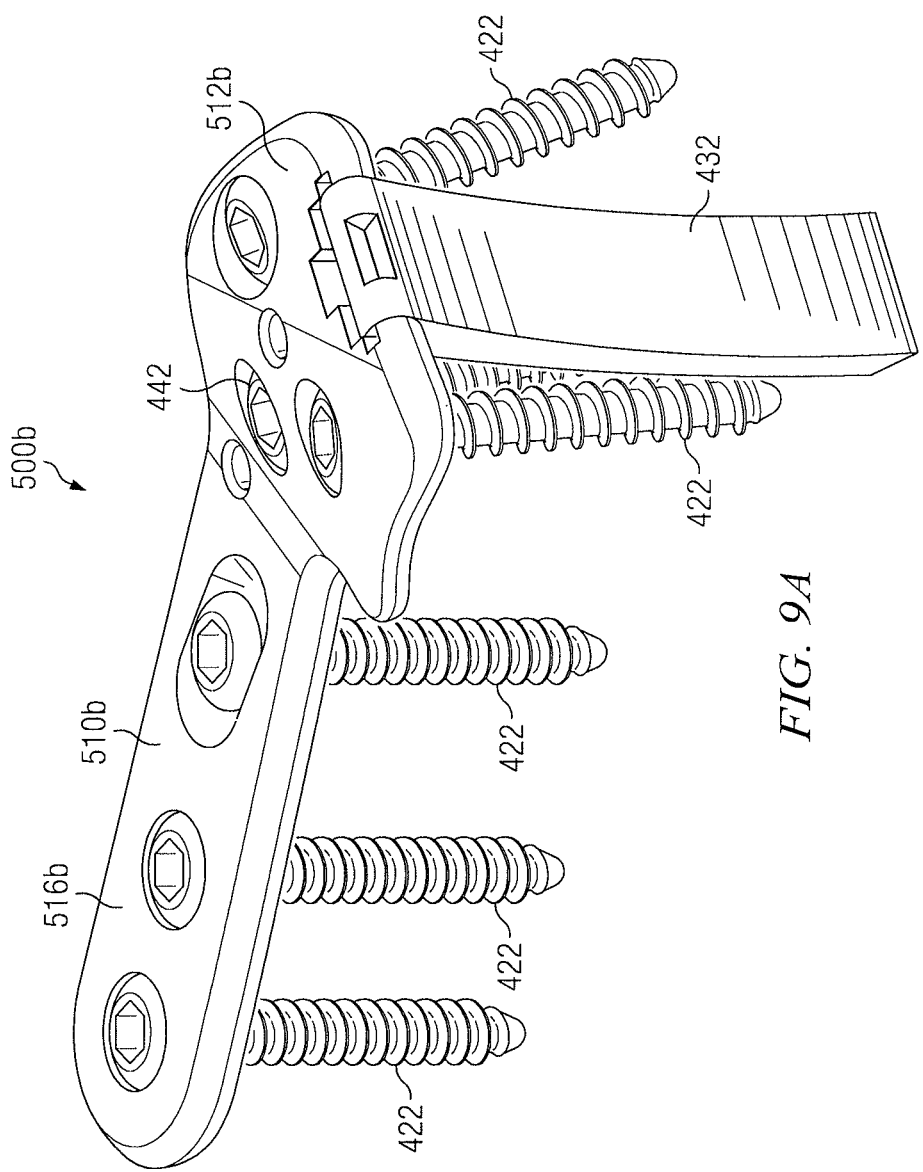

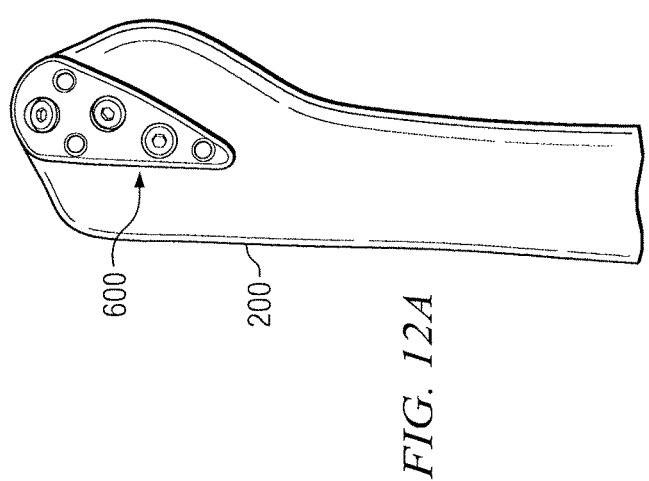
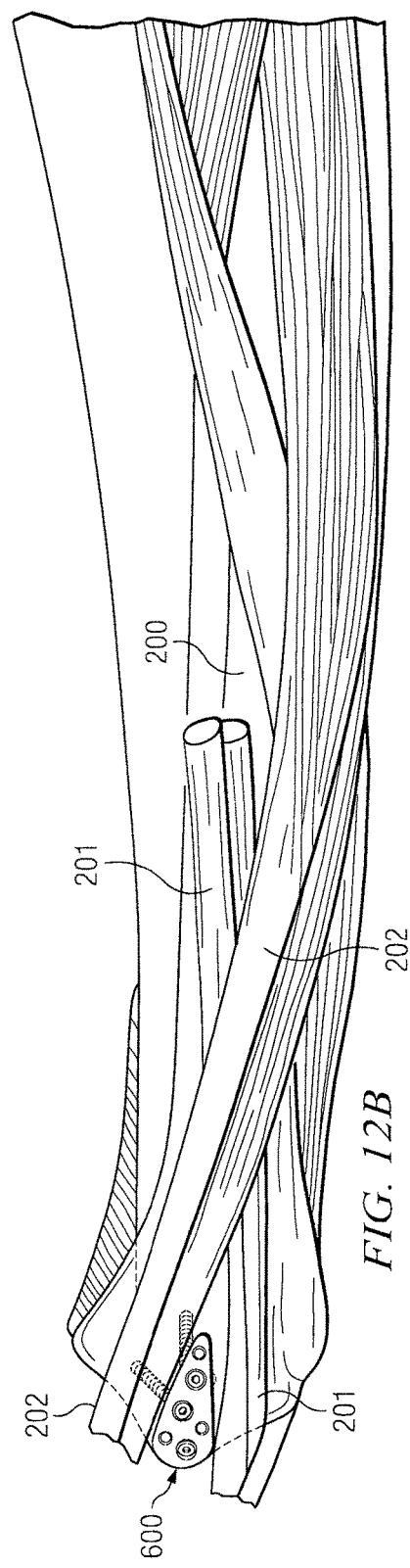
FIG. 12A
FIG. 12B

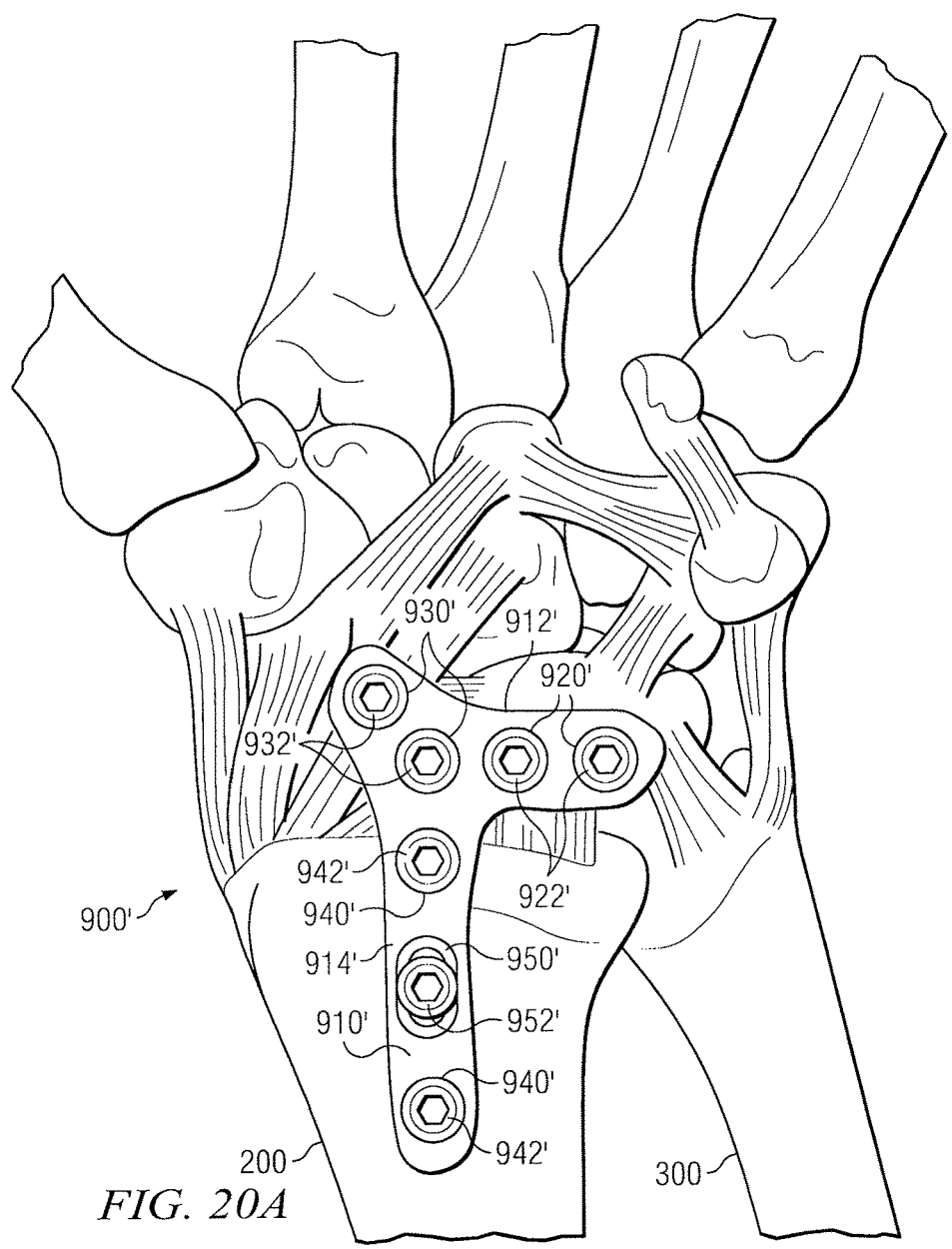
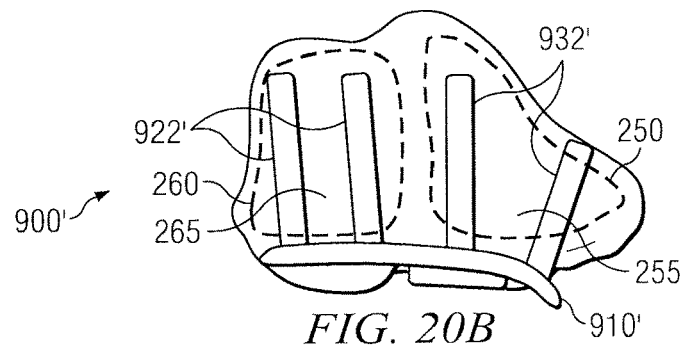
FIG. 20A
FIG. 20B

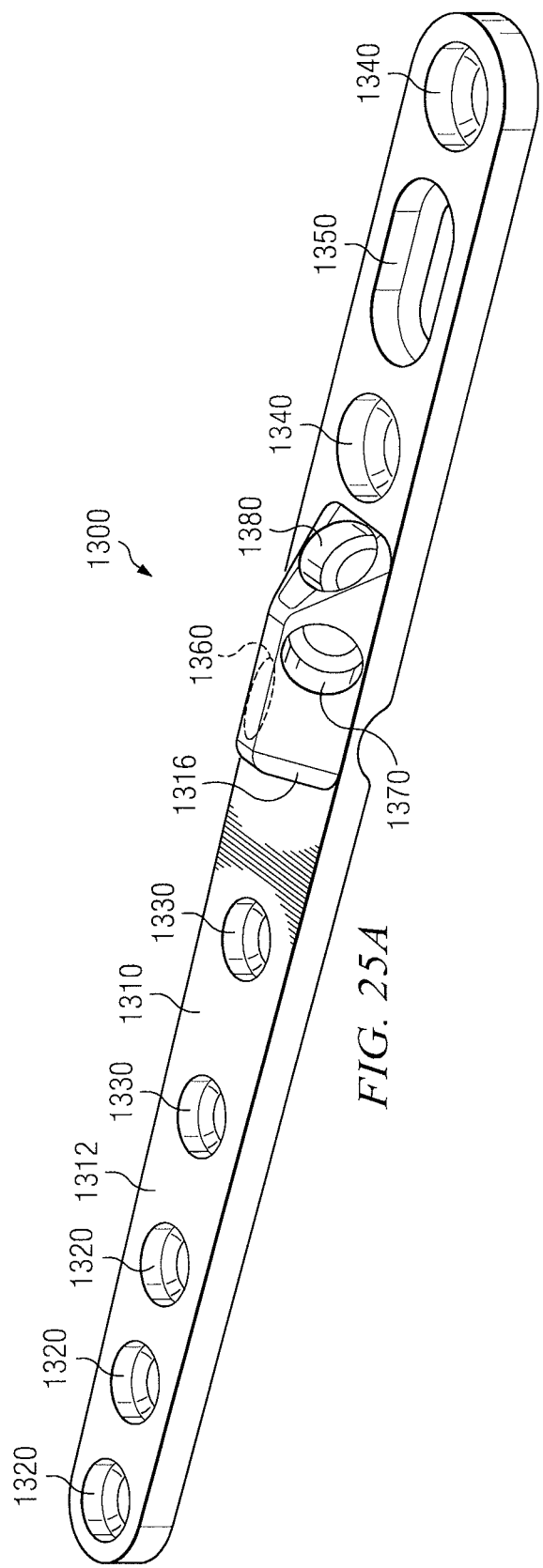

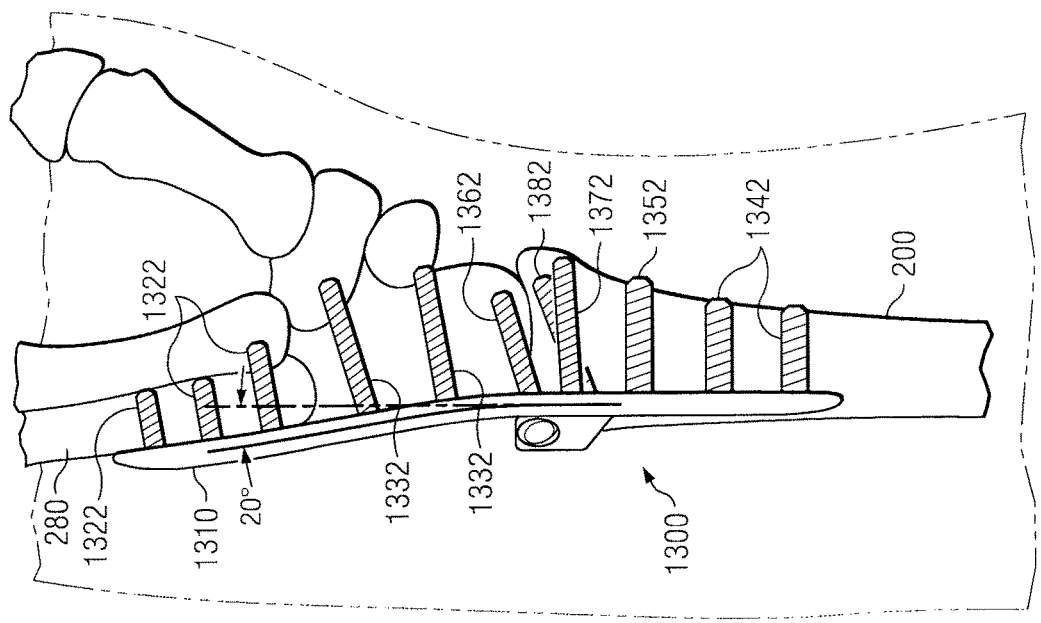
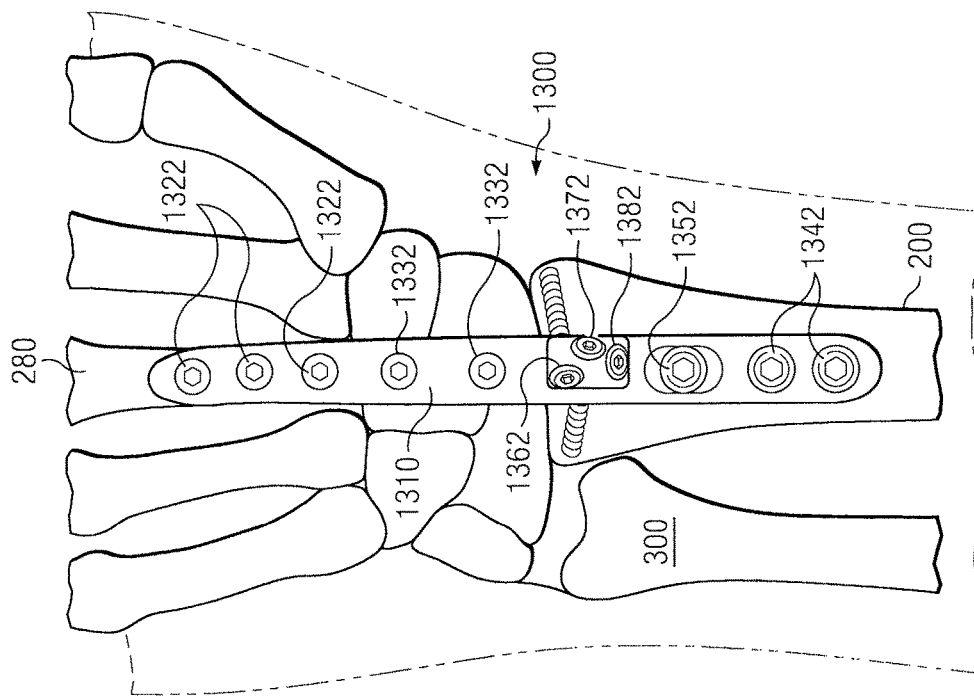

SYSTEM FOR TREATING BONE FRACTURES

RELATED APPLICATIONS

This application claims priority to U.S. patent application Ser. No. 61/332,439, entitled "RADIAL FUSION PLATE APPARATUS," which was filed on May 7, 2010. This application also claims priority to U.S. patent application Ser. No. 61/405,822, entitled "HIGHLY ADAPTABLE RECONSTRUCTION AND PLATING SYSTEM AND METHOD II," which was filed on Oct. 22, 2010.

TECHNICAL FIELD

This disclosure generally relates to bone fractures, and more particularly, to a system for treating bone fractures.

BACKGROUND

A bone fracture is a medical condition in which there is a break in a bone. In some circumstances, a bone fracture can be the result of high force impact or stress.

SUMMARY

Some embodiments may provide numerous technical advantages. For example, a technical advantage of some embodiments may include the capability to treat different classes of fractures, such as different classes of radial and ulnar fractures. A technical advantage of some embodiments may include, for example, the capability to restore a subchondral fragment to its original position. As another example, a technical advantage of some embodiments may include the capability to provide fixation, fusion, and/or spanning to a variety of radial and ulnar fractures.

Various embodiments of the invention may include none, some, or all of the above technical advantages. One or more other technical advantages may be readily apparent to one skilled in the art from the figures, descriptions, and claims included herein.

BRIEF DESCRIPTION OF THE DRAWINGS

A more complete understanding of embodiments of the disclosure will be apparent from the detailed description taken in conjunction with the accompanying drawings in which:

FIGS. 4A-4F show front, back, side, top, and bottom views of a beam of FIG. 2A according to one embodiment;
FIGS. 7A and 7B show a variation of the bone fixation system of FIGS. 6A-6D according to one embodiment;
FIG. 9A shows a bone fixation system according to one embodiment;
FIGS. 12A and 12B show the bone fixation system of FIGS. 11A-11F installed between the first and second extensor compartments of the radius of FIG. 5;
FIGS. 20A and 20B show a bone fusion system according to one embodiment;
FIGS. 25A-25D show a bone fusion/fixation/spanning system according to one embodiment.

DETAILED DESCRIPTION OF EXAMPLE EMBODIMENTS

It should be understood at the outset that, although example implementations of embodiments are illustrated below, various embodiments may be implemented using a number of techniques, whether currently known or not. The present disclosure should in no way be limited to the example implementations, drawings, and techniques illustrated below.

Bone fractures may be classified in a variety of ways. For example, fractures may be classified anatomically. Anatomical classifications may begin with specifying the involved body part, such as the skull, spine, ribs, sternum, shoulder, arm, hand, pelvis, femur, patella, lower leg, or foot. Within each anatomical classification, fractures may be classified based on a more specific localization. For example, arm fractures may be categorized into humerus fractures, ulnar fractures, and radius fractures. Anatomical classifications may also have additional definition criteria that distinguish between different types of fractures at the same location. For example, radius fractures may include various types of distal-radius fractures.

Teachings of certain embodiments recognize the capability to provide fixation and/or fusion plates for treating different classes of fractures, such as different classes of radial and ulnar fractures. Teachings of certain embodiments also recognize the capability to apply treatment techniques across multiple classes of fractures.

Subchondral Beams

Figure 1A:
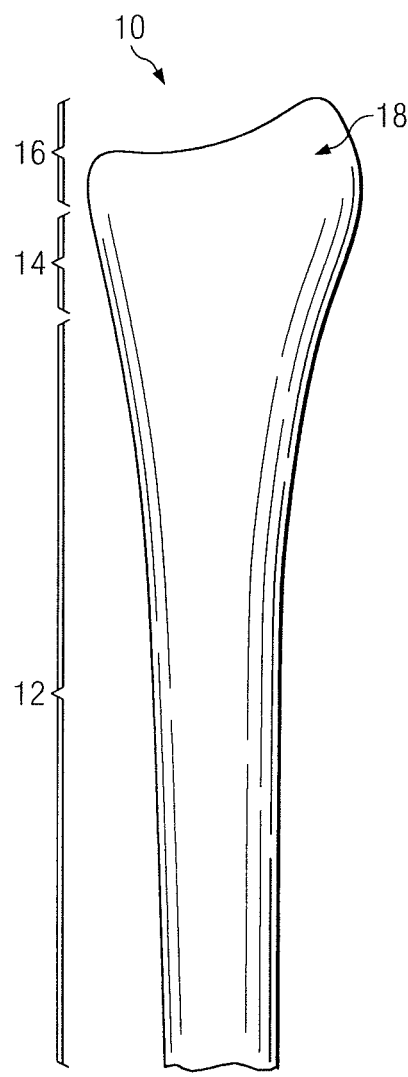
FIG. 1A shows an example bone.

FIG. 1A shows a bone 10. In this example, bone 10 is a long bone having a diaphysis 12, a metaphysis 14, and an epiphysis 16. Diaphysis 12 may represent a mid section or shaft of bone 10. Metaphysis 14 may represent a wider portion of bone 10 adjacent to diaphysis 12. Epiphysis 16 may represent a rounded end of bone 10 adjacent to metaphysis 14. Epiphysis 16 may include a region of subchondral bone 18. Subchondral bone 18 may represent a portion of bone located below cartilage in epiphysis 16.

Figure 1B:
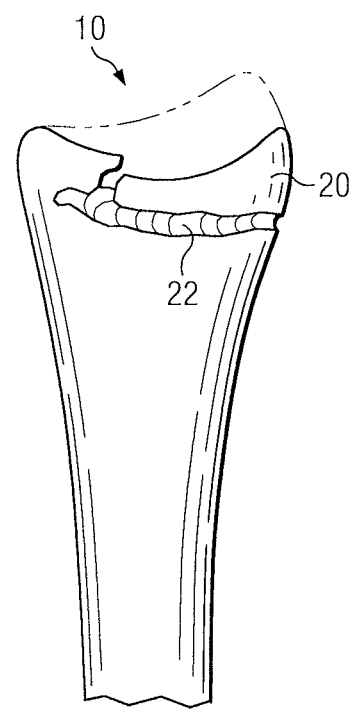
FIG. 1B shows the bone of FIG. 1A having a fracture.

FIG. 1B shows a bone 10 having a fracture 22. In this example, fracture 22 is an intra-articular fracture resulting in subchondral fragment 20 becoming partially or completely dislodged from bone 10. As shown in FIG. 1B, subchondral fragment 20 has moved from its original position. Teachings of certain embodiments recognize the capability to restore a subchondral fragment, such as subchondral fragment 20, to its original position.

Figure 2A:
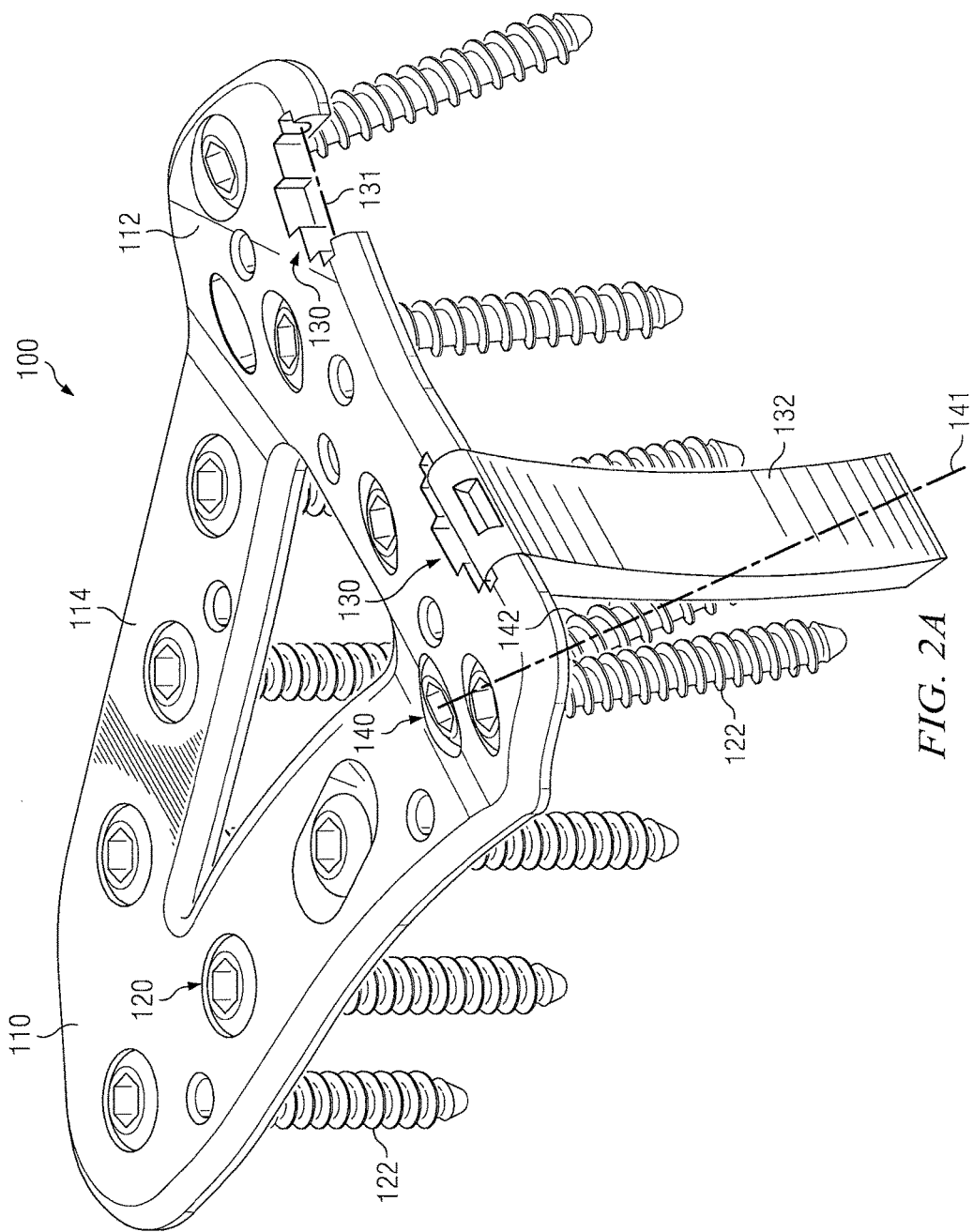
FIG. 2A shows a bone fixation system according to one embodiment.
Figure 2B:
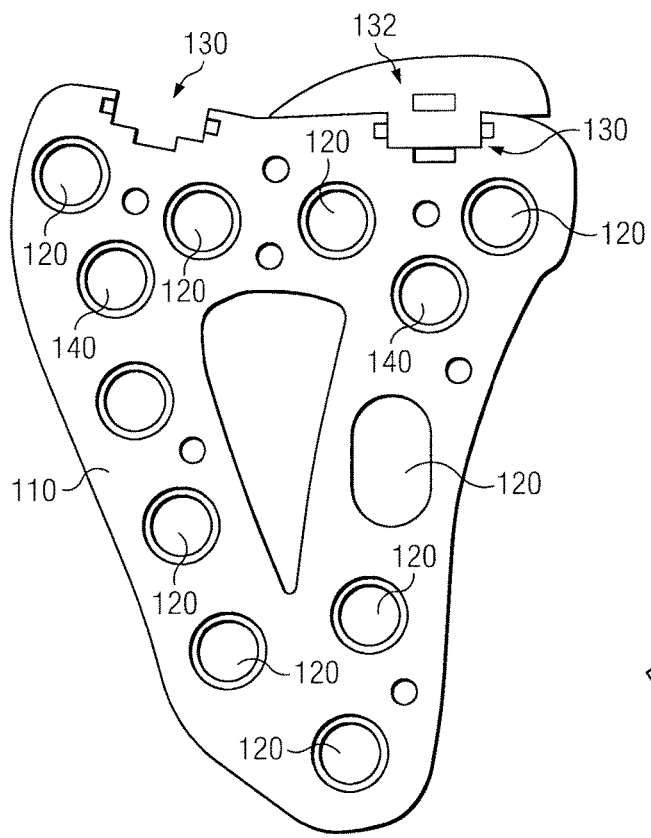
FIGS. 2B and 2C show the bone fixation system of FIG. 2A with fixation devices and positioning devices removed.
Figure 2C:
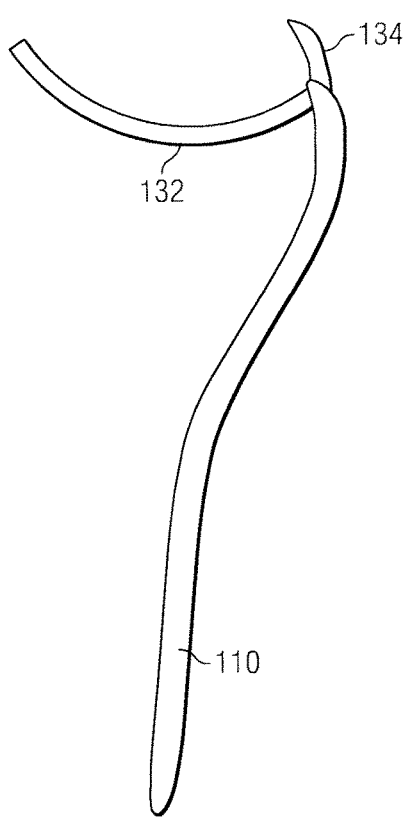

FIG. 2A shows a bone fixation system 100 according to one embodiment. In the example of FIG. 2A, bone fixation system 100 includes a plate 110 having one or more openings 120, 130, and 140; one or more fixation devices 122; one or more beams 132; and one or more positioning devices 142. FIGS. 2B and 2C show the bone fixation system 100 of FIG. 2A with fixation devices 122 and positioning devices 142 removed.

Plate 110 may be comprised of any suitable material. For example, embodiments of plate 110 may be comprised of a bioabsorbable material, a non-bioabsorbable material, or a combination of both. Examples of materials for plate 110 may include, but are not limited to, metals such as titanium alloy, polymers, and laminates. In some embodiments, plate 110 may also include radio-opaque materials to allow visualization on radiographs.

Plate 110 may include any number of openings, such as openings 120, 130, and 140. An opening may include any threaded or unthreaded, fixed or variable angle, locking or non-locking, partially or fully enclosed void in plate 110. In some embodiments, openings may be recessed such that they may receive a fixation device without the head of the fixation device extending above the surface of the plate.

In FIG. 2B, for example, openings 120 are shown as fully-enclosed holes, and openings 130 are shown as partially-enclosed holes positioned along the outer edge of plate 110. In the example embodiment of FIGS. 2A-2C, openings 120 are configured to receive fixation devices 122, openings 130 are configured to receive beams 132, and openings 140 are configured to receive positioning devices 142.

In some embodiments, plate 110 may be configured to conform to bone 10. In the embodiment illustrated in FIGS. 2A-2C, for example, plate 110 is configured to conform to the metaphysis and the diaphysis of a radial bone. Openings 120, 130, and 140 may be positioned in either the metaphysis portion of plate 110, the diaphysis portion of plate 110, or both. For example, in one embodiment, openings 120 are positioned in both the metaphysis and diaphysis portions, and openings 130 and 140 are positioned in the metaphysis portion. For example, FIG. 2A shows plate 110 having a metaphysis portion 112 with a row of two openings 130 distal to a row of four openings 120, which is distal to a row of two openings 140; and a diaphysis portion 114 having two columns of openings 120. In this example, metaphysis portion 112 may be angled relative to diaphysis portion 114 such that plate 110 conforms to bone 10.

Plate 110 may be dimensioned in any suitable manner. In some embodiments, the dimensions and contour of plate 110 is determined based on measurements from scans of a bone. As one example, plate 110 may be dimensioned based on measurements determined from a particular fractured bone. As another example, bones may be categorized according to size and/or contour, and different variations of plate 110 may be configured to conform to one or more of the different categories. Plate 110 may still be considered to conform to a bone even if such conformance is only approximate or imperfect. For example, plate 110 may be manufactured such that it generally conforms to a large number of bones in the population.

Fixation device 122 may include any device for engaging bone 10. For example, in one embodiment, fixation device 122 is a screw or peg operable to secure plate 110 to bone 10. Additional examples of fixation device 122 may include locking and non-locking smooth pegs, locking and non-locking cortical screws, and locking and non-locking cannulated compression screws. In some embodiments, fixation-device 122 may have a smooth tip.

Fixation device 122 may be comprised of any suitable material. For example, embodiments of fixation device 122 may be comprised of a bioabsorbable material, a non-bioabsorbable material, or a combination of both. Examples of materials for fixation device 122 may include, but are not limited to, metals such as titanium alloy. In some embodiments, fixation device 122 may also include radio-opaque materials to allow visualization on radiographs.

In some embodiments, opening 120 is defined by a threaded hole in plate 110, and fixation device 122 has a threaded head portion configured to engage the threaded hole. In some embodiments, fixation device 122 also includes a threaded shaft portion for engaging bone.

Beam 132 may include any device for traversing through opening 130 and residing proximate to subchondral fragment 20 when plate 110 is placed on bone 10. In the example of FIG. 2A, beam 132 comprises an elongated member having a first end configured to engage the plate proximate to axis of rotation 131 and a second end opposite the first end. Thus, beam 132 may rotate about axis of rotation 131, which projects through opening 130 and plate 110.

In the example of FIG. 2C, beam 132 also comprises a buttress member 134 rigidly coupled to the elongated member at the first end. Teachings of certain embodiments recognize the capability for beam 132 with buttress member 134 to help prevent movement of small bone fragments. For example, in some embodiments, buttress member 134 may prevent small fragments from where the ligament attaches to the lunate bone from shifting forward. In particular, a loose fragment on the distal radius may be connected by ligament to the lunate, and buttress member 134 may prevent the lunate bone from migrating out of position.

In some embodiments, beam 132 comprises a straight, elongated member. In the example of FIGS. 2A and 2C, however, beam 132 has a curvature from the first end to the second end. Teachings of certain embodiments recognize that beam 132 may be curved to allow beam 132 to reside closer to subchondral fragment 20 when beam 132 is installed.

Beam 132 may be comprised of any suitable material. For example, embodiments of beam 132 may be comprised of a bioabsorbable material, a non-bioabsorbable material, or a combination of both. In some embodiments, buttress member 134 may be bioabsorbable so as to minimize the possibility of tendon irritation. Examples of materials for beam 132 may include, but are not limited to, metals such as titanium alloy. In some embodiments, beam 132 may also include radio-opaque materials to allow visualization on radiographs.

Positioning device 142 may include any device for traversing through opening 140 and engaging beam 132 when beam 132 is installed. In some embodiments, positioning device 142 may traverse through opening 140 along central axis 141. Central axis may project through any portion of opening 140 and is not necessarily in the center of opening 140.

In some embodiments, central axis 141 projects through beam 132 when beam 132 is installed. Thus, inserting positioning device 142 through opening 140 along central axis 141 may cause positioning device 142 to engage beam 132 when beam 132 is installed. In some embodiments, positioning device 142 may have a blunt tip for engaging beam 132. For example, in some embodiments positioning device 142 may have a rounded or flat tip.

In some embodiments, opening 140 is defined by a threaded hole in plate 110, and positioning device 142 has a threaded head portion configured to engage the threaded hole. In some embodiments, positioning device 142 also includes a threaded shaft portion for engaging bone. In some embodiments, the shaft portion is partially threaded. For example, in one embodiment, the shaft portion near the head may be threaded, but the shaft portion near the tip is not. In one example embodiment, positioning device 142 has a blunt tip, and the region of the shaft portion within ten millimeters of the tip is not threaded.

Positioning device 142 may be comprised of any suitable material. For example, embodiments of positioning device 142 may be comprised of a bioabsorbable material, a non-bioabsorbable material, or a combination of both. Examples of materials for positioning device 142 may include, but are not limited to, metals such as titanium alloy. In some embodiments, positioning device 142 may also include radio-opaque materials to allow visualization on radiographs.

In operation, positioning device 142 may traverse along central axis 141 and, after engaging beam 132, cause beam 132 to rotate about axis of rotation 131. Causing beam 132 to rotate may cause beam 132 to reposition subchondral fragment 20. Teachings of certain embodiments recognize that rotating beam 132 may result in subchondral fragment 20 being restored at or near its original position. In some embodiments, variations of positioning device 142 are provided with different lengths so as to rotate beam 132 to different angles.

In some embodiments, opening 140 may define the direction of central axis 141. In other embodiments, however, opening 140 may allow for a range of orientations of central axis 141. In some embodiments, a drill guide or jig may be used to direct positioning device 142 in a direction along central axis 141.

Figure 3A:
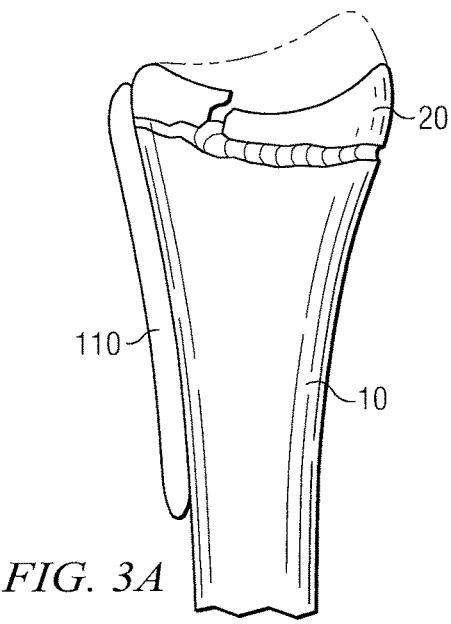
FIGS. 3A-3F show progressive views of the bone fixation system of FIG. 2A being installed on the fractured bone of FIG. 1B according to one embodiment.
Figure 3B:
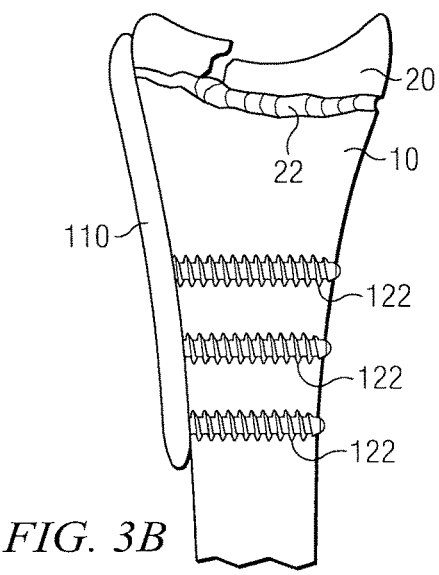

FIGS. 3A-3F show progressive views of the bone fixation system 100 of FIG. 2A being installed on bone 10 of FIG. 1B according to one embodiment. In FIG. 3A, plate 110 is placed on bone 10. In this example, plate 110 is placed on the volar side of bone 10. In FIG. 3B, fixation devices 122 are installed to secure plate 110 to bone 10.

Figure 3C:
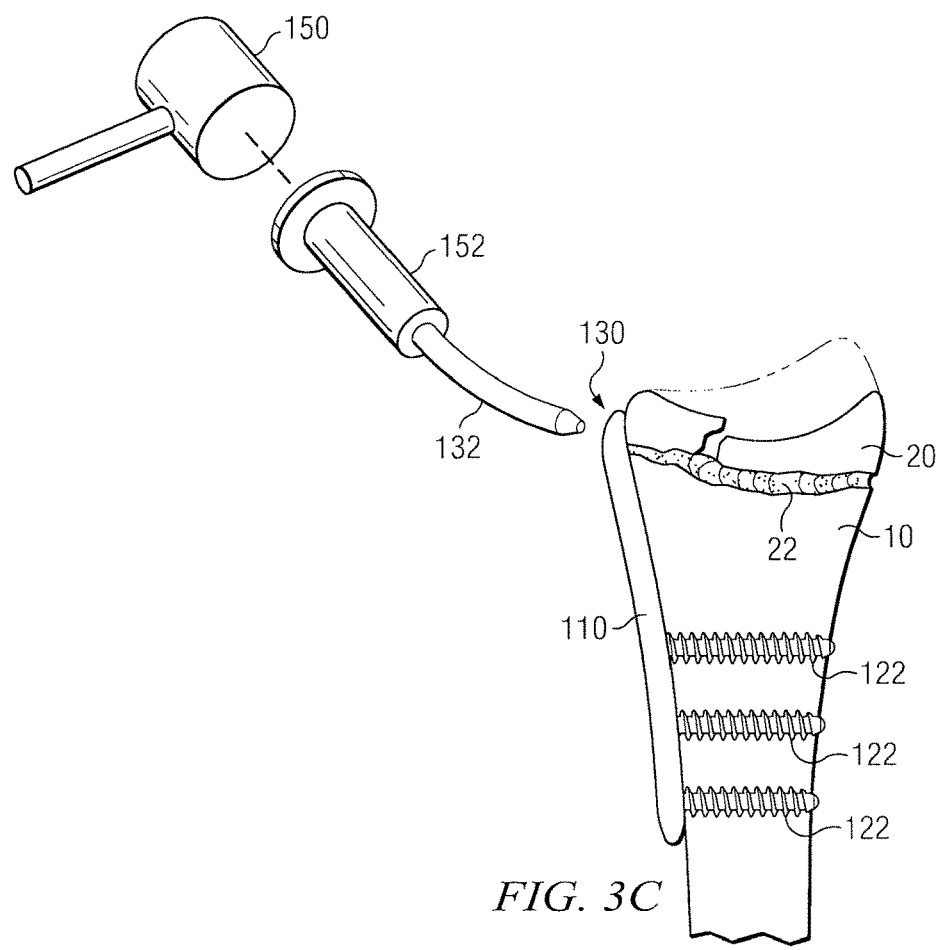
Figure 3D:
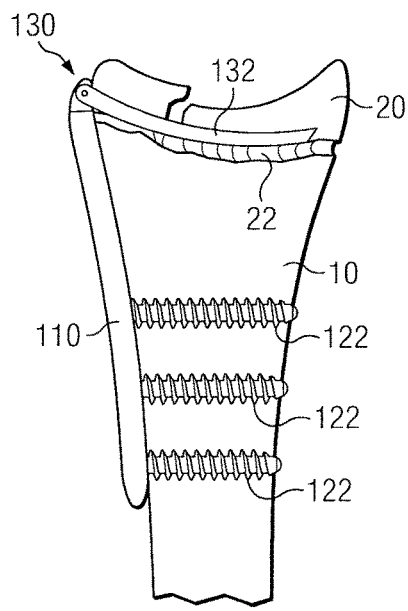

In FIG. 3C, beam 132 is aligned over opening 130. In this example, opening 130 is positioned over fracture 22. Beam 132 may be inserted into or proximate to bone 10 proximate to subchondral fragment 20 in any suitable manner. In one example embodiment, beam 132 may be inserted using a first driving device 150 and an insertion guide 152. One example of first driving device 150 may include a mallet, and one example of insertion guide 152 may include an awl. FIG. 3D shows beam 132 inserted through opening 130 in an installed position.

Figure 3E:
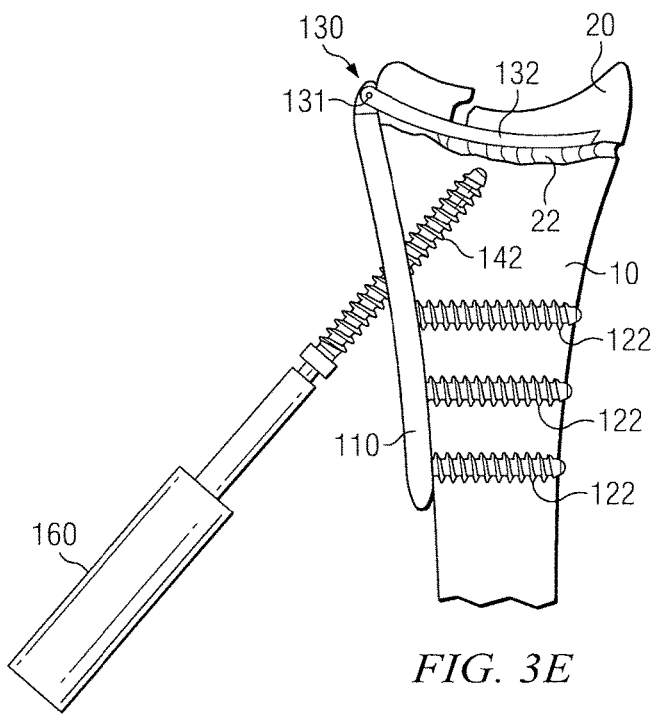

In FIG. 3E, positioning device 142 is inserted through opening 140 and bone 10. In some embodiments, a hole, such as a pilot hole, is drilled into bone 10 prior to inserting positioning device 142. Positioning device 142 may be inserted into bone 10 in any suitable manner. In one example embodiment, positioning device 142 may be inserted using a second driving device 160. One example of second driving device 160 may include a screwdriver. In some embodiments, positioning device 142 is aligned along central axis 141 using a drill guide.

Figure 3F:
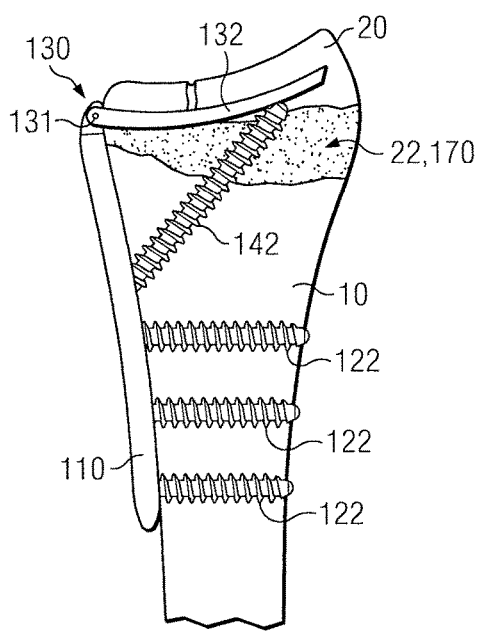

FIG. 3F shows positioning device 142 inserted through bone 10 such that it has engaged beam 132 and caused beam 132 to rotate about axis of rotation 131. In this example, positioning device 142 has caused beam 132 such that subchondral fragment 20 has been repositioned near its original position. In some embodiments, beam 132 rotates approximately 40-60 degrees. In one example embodiment, beam 132 rotates approximately 51 degrees from a position 40 degrees proximal to the perpendicular to plate 110 to a position 11 degrees distal to the perpendicular to plate 110.

As shown in FIG. 3F, repositioning subchondral fragment 20 has created a void between bone 10 and subchondral fragment 20. Teachings of certain embodiments recognize the capability to backfill this void with fill material 170 such as a biological or synthetic bone graft. In some embodiments, inserting material into this void may stabilize the location of subchondral fragment 20, allowing some or all of bone fixation system 100 to be removed. For example, in one embodiment, inserting fill material 170 may allow positioning device 142 to be removed. In other embodiments, components of bone fixation system 100, such as positioning device 142, may remain installed after fill material 170 is inserted.

FIGS. 4A-4F show front, back, side, top, and bottom views of beam 132 according to one embodiment. In some embodiments, beam 132 may include a pin opening 136 configured to receive a pin 138. In some embodiments, pin 138 may become approximately collinear with axis of rotation 131 when beam 132 is installed into opening 130. In some embodiments, pin 138 is removable. In other embodiments, pin 138 is a permanent structure of beam 132. In some embodiments, beam 132 does not have a pin opening 136, and pin 138 is a contiguous part of beam 132. For example, in one embodiment, beam 132 and pin 138 are machined from the same piece of contiguous material. In some embodiments, pin 138 is sized to be received by a corresponding notch in opening 130.

Volar Plates

Figure 5:
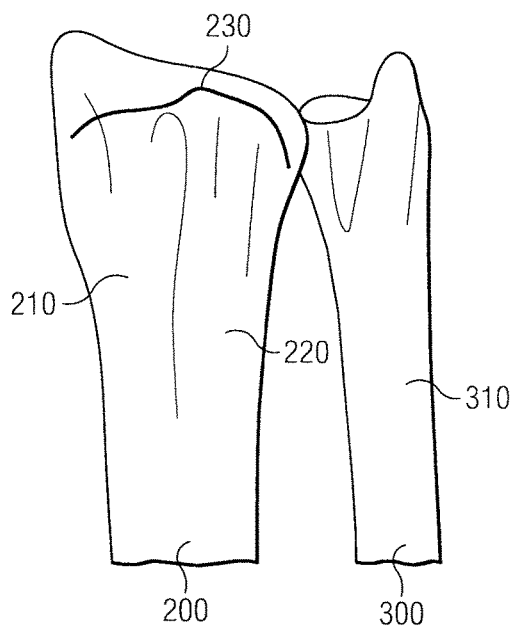
FIG. 5 shows an example radius and an example ulna.

FIG. 5 shows an example radius 200 and an example ulna 300. According to column theory, radius 200 and ulna 300 may be divided into three longitudinal columns: lateral column 210, central column 220, and ulnar column 310. Lateral column 210, which may also be referred to as the radial column, includes the portion of radius 200 extending from the radial styloid and the scaphoid facet 255 to the radius shaft. Central column 220, which may also be referred to as the intermediate column, includes the portion of radius 200 extending from the lunate facet 265 and the sigmoid notch to the radius shaft. Ulnar column 310 includes the portion of ulna 300 extending from the ulnar head and the ulnar styloid towards the humerus.

Radius 200 may also include a watershed line 230. Watershed line 230 may represent a theoretical line marking the most volar aspect of the volar margin of radius 200. Watershed line 230 may correspond to where the concavity of the distal radius ends and where the flexor tendons are in contact with radius 200.

In some circumstances, radius 200 may suffer from fractures along lateral column 210 and/or central column 220. Teachings of certain embodiments recognize the capability to provide a volar plate to provide fixation of these and other fractures.

Figure 6A:
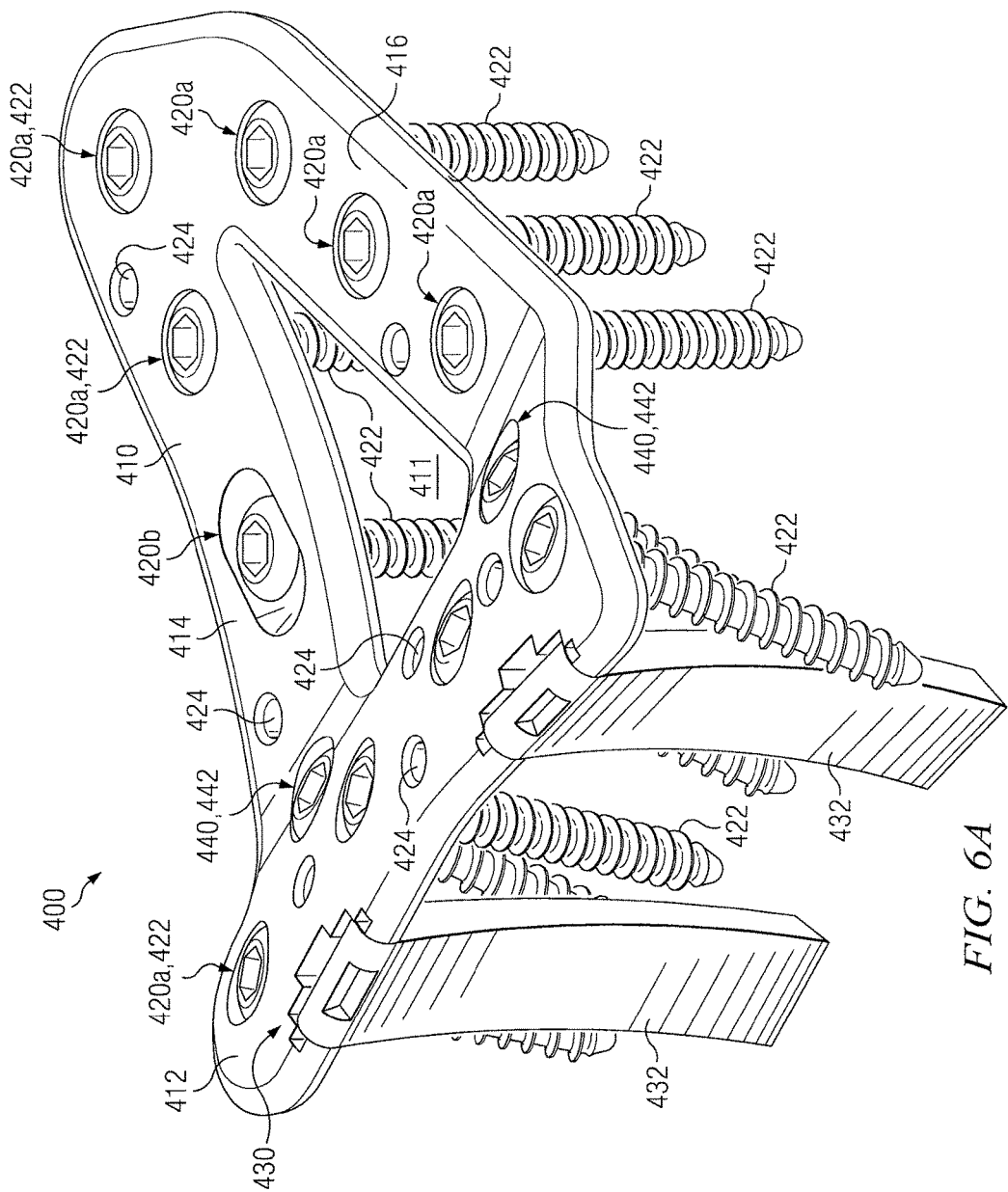
FIGS. 6A-6D show a bone fixation system according to one embodiment.
Figure 6B:
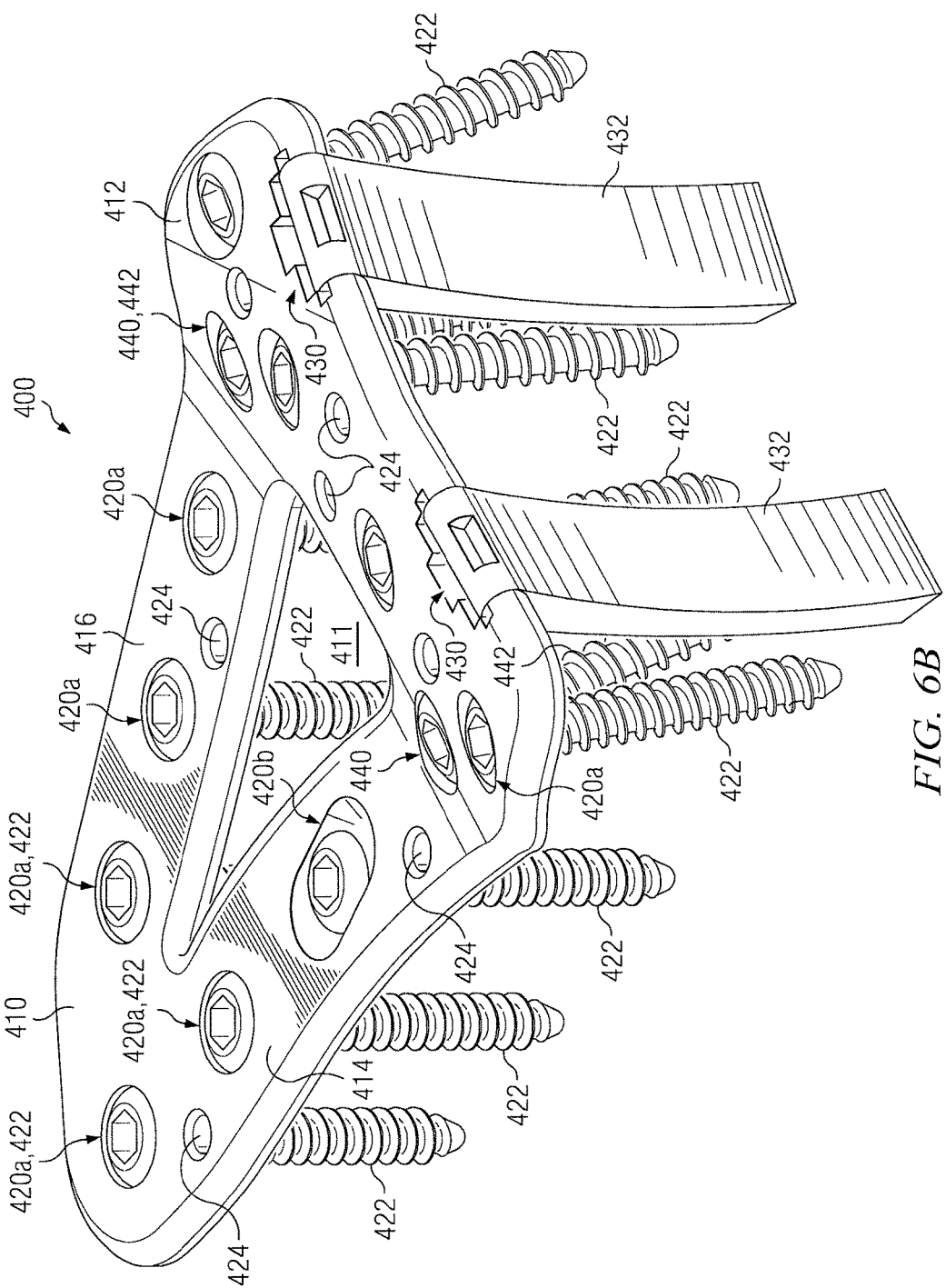
Figure 6C:
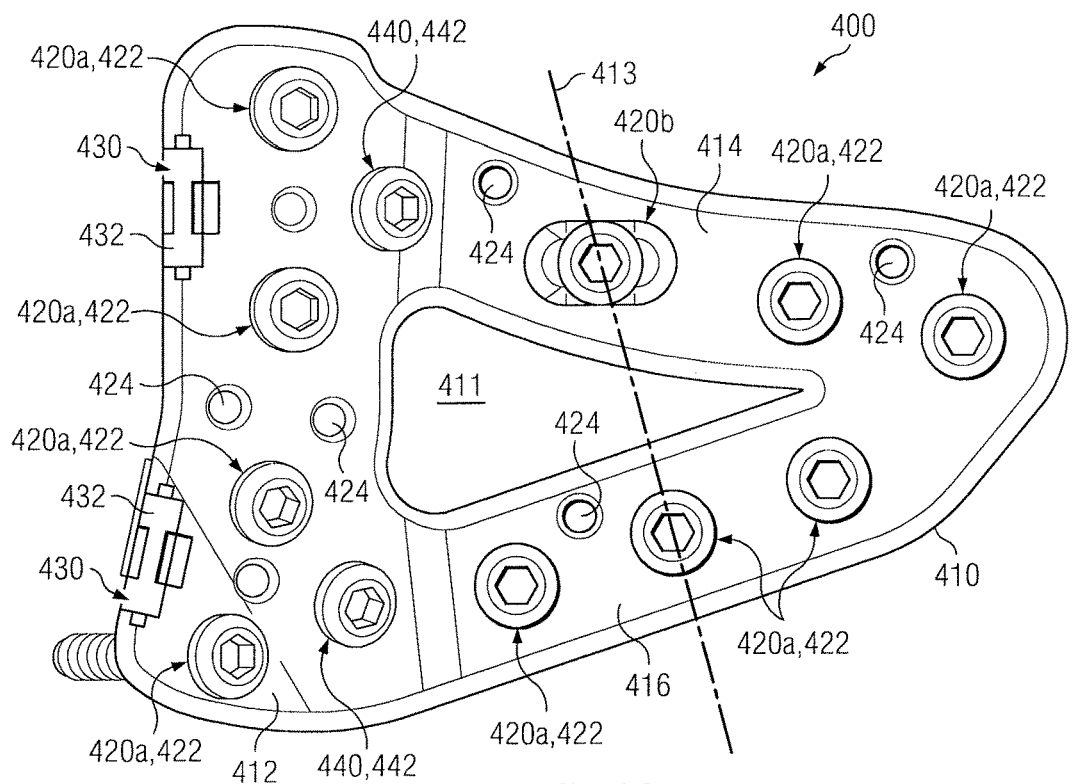
Figure 6D:
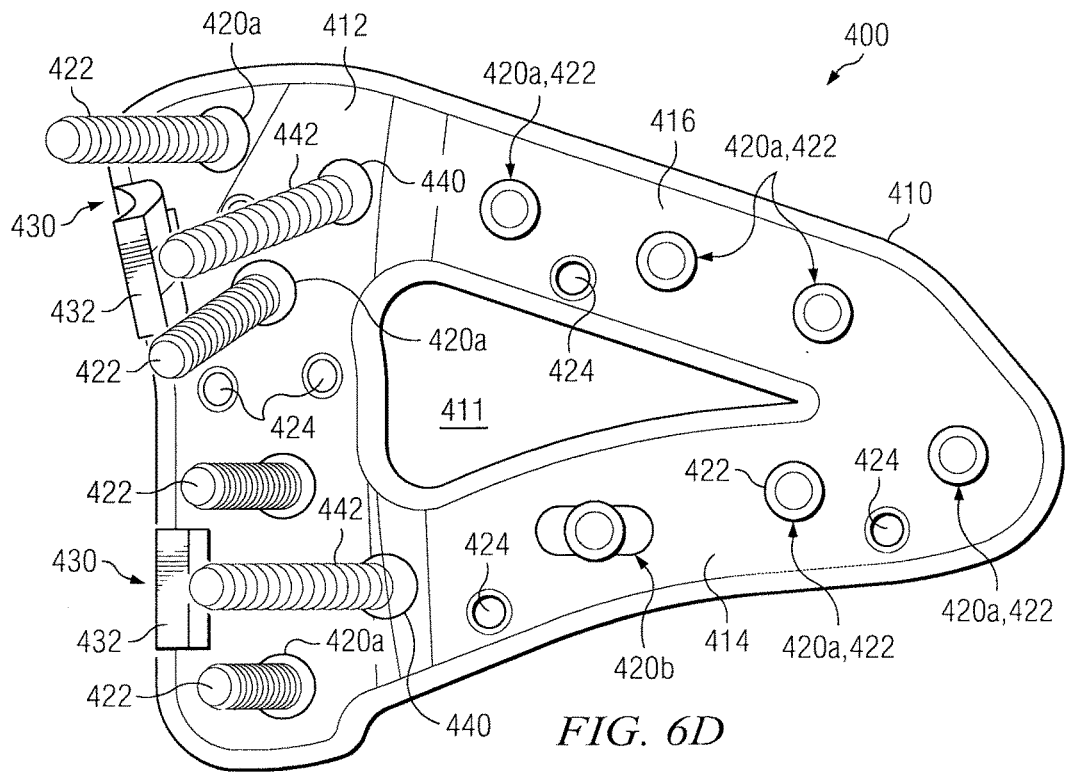

FIGS. 6A, 6B, 6C, and 6D show a bone fixation system 400 according to one embodiment. FIGS. 6A and 6B show perspective views of bone fixation system 400, FIG. 6C shows a top view of bone fixation system 400, and FIG. 6D shows a bottom view of bone fixation system 400. Bone fixation system 400 may include a plate 410 having one or more openings 420a, 420b, 430, and 440, and one or more Kirschner wire (k-wire) holes 424; one or more fixation devices 422; one or more beams 432; and one or more positioning devices 442.

Plate 410 may be comprised of any suitable material. For example, embodiments of plate 410 may be comprised of a bioabsorbable material, a non-bioabsorbable material, or a combination of both. Examples of materials for plate 110 may include, but are not limited to, metals such as titanium alloy, polymers, and laminates. In some embodiments, plate 410 may also include radio-opaque materials to allow visualization on radiographs.

In some embodiments, plate 410 may be configured to conform to the volar side of radius 200. In the embodiment illustrated in FIGS. 6A-6D, for example, plate 410 is configured to conform to the metaphysis and the diaphysis of radius 200. In this example, plate 410 includes a metaphysis portion 412 configured to conform to the metaphysis of radius 200, a central column portion 414 configured to conform to the central column of the diaphysis of radius 200, and a lateral column portion 416 configured to conform to the lateral column of the diaphysis of radius 200.

In the embodiment illustrated in FIGS. 6A-6D, metaphysis portion 412, central column portion 414, and lateral column portion 416 are joined together to form a central window 411 through plate 410. Teachings of certain embodiments recognize that central window 411 may increase visibility for placing plate 410 on radius 200. Teachings of certain embodiments also recognize that central window 411 may provide an opening for fill material, such as fill material 170, to be inserted proximate to radius 200.

Plate 410 may be dimensioned in any suitable manner. In some embodiments, the dimensions and contour of plate 410 is determined based on measurements from scans of a bone. As one example, plate 410 may be dimensioned based on measurements determined from a particular fractured bone. As another example, bones may be categorized according to size and/or contour, and different variations of plate 410 may be configured to conform to one or more of the different categories. Plate 410 may still be considered to conform to a bone even if such conformance is only approximate or imperfect. For example, plate 410 may be manufactured such that it generally conforms to a large number of bones in the population, each of which may have a unique shape.

The outer boundaries of plate 410 may have any suitable dimensions. In one example embodiment, metaphasis portion 412 of plate 410 is dimensioned to conform to radius 200 such that metaphasis portion 412 ends proximal to watershed line 230 along the central column. In another example embodiment, metaphasis portion 412 of plate 410 is dimensioned to conform to radius 200 such that metaphasis portion 412 ends distal to watershed line 230 along the lateral column. Teachings of certain embodiments recognize that dimensioning plate 410 such that the metaphasis portion 412 ends distal to watershed line 230 may allow bone fixation system 400 to have stronger fixation to the radio styloid and to provide a volar buttress for lateral column fractures. In another example embodiment, plate 410 is dimensioned to abut without violating the distal radio-ulnar joint or its ligaments. In yet another example embodiment, plate 410 is dimensioned to abut without violating the first extensor compartment of radius 200.

Plate 410 may include any number of openings, such as openings 420a, 420b, 430, and 440, and one or more Kirschner wire (k-wire) holes 424. An opening may include any threaded or unthreaded, fixed or variable angle, locking or non-locking, partially or fully enclosed void in plate 410. In some embodiments, openings may be recessed such that they may receive a fixation device without the head of the fixation device extending above the surface of the plate.

In the example embodiment of FIGS. 6A-6D, openings 420a, 430, and 440 are configured to receive fixation devices 422 and/or positioning devices 442, and openings 430 are configured to receive beams 432.

In the example of FIGS. 6A-6D, metaphasis portion 412 includes openings 420a, 430, and 440 arranged in three rows. The most distal row in metaphasis portion 412 includes two openings 430 configured to receive positioning devices 442. The second most distal row includes four openings 420 configured to receive fixation devices 422. Teachings of certain embodiments recognize that inserting fixation devices 422 into openings 420 in the second most distal row may allow for fixation of plate 410 and/or capture of fracture fragments. In some embodiments, the second most distal row may include at least one opening 420 configured to receive a fixation device 422 for engaging the radial styloid. The first proximal row in metaphasis portion 412 includes two openings 440. Openings 440 in metaphasis portion 412 may be configured to receive fixation devices 422 and/or positioning devices 442. For example, openings 440 in metaphasis portion 412 may receive fixation devices 422 if beams 432 are not inserted in the most distal row of openings 430.

In some embodiments, openings such as openings 420a and 420b are provided along the length of central column portion 414 and lateral column portion 416. Teachings of certain embodiments recognize the capability to provide central column portion 414 and lateral column portion 416 with sufficient width such that they are wide enough to contain openings such as 420a and 420b. Thus, openings may be provided adjacent to central window 411. For example, in some embodiments, openings on central column portion 414 may be coplanar with central window 411 and openings on lateral column portion 416. For example, in FIG. 6C, an imaginary plane 413 may be drawn extending through an opening on central column portion 414, central window 411, and an opening on lateral column portion 416.

Fixation device 422 may include any device for engaging radius 200. One example of fixation devices 422 may include fixation device 122. In one embodiment, fixation device 422 is a screw or peg operable to secure plate 410 to radius 200. Additional examples of fixation device 422 may include locking and non-locking smooth pegs, locking and non-locking cortical screws, and locking and non-locking cannulated compression screws. In some embodiments, fixation-device 422 may have a smooth tip.

Fixation device 422 may be comprised of any suitable material. For example, embodiments of fixation device 422 may be comprised of a bioabsorbable material, a non-bioabsorbable material, or a combination of both. Examples of materials for fixation device 422 may include, but are not limited to, metals such as titanium alloy. In some embodiments, fixation device 422 may also include radio-opaque materials to allow visualization on radiographs.

In some embodiments, opening 420a is defined by a threaded hole in plate 410, and fixation device 422 has a threaded head portion configured to engage the threaded hole. In some embodiments, fixation device 422 also includes a threaded shaft portion for engaging bone.

In some embodiments, opening 420b may be an oblong opening. Teachings of certain embodiments recognize that an oblong opening may aid in positioning a plate on a bone and may be used to provide compression. For example, plate 410 may be attached to radius 200 by inserting fixation device 422 through oblong opening 420b to engage bone. Plate 410 may then be repositioned relative to radius 200, allowing fixation device 422 to move relative to oblong opening 420b. Once plate 410 is in a suitable position, fixation device 422 may be tightened to radius 220, and additional fixation devices 422 may be inserted.

K-wire hole 424 may include any opening sized to receive a k-wire. A k-wire is a surgical pin that may provide temporary, provisional, and/or supplemental fixation. K-wires may be sterilized, sharpened, and/or smooth. K-wires may be composed of any suitable material, such as stainless steel. K-wires may be made of bioabsorbable or non-bioabsorbable materials. A k-wire may be inserted into k-wire hole 424 in any suitable manner, such as using a power or hand drill. K-wires may be of any suitable size. Examples of k-wire sizes may include a 0.054 inch diameter and a 0.062 inch diameter. In some embodiments, k-wire holes 424 may have a fixed orientation so as to direct k-wires in a particular direction.

Beam 432 may include any device for traversing through opening 430 and residing proximate to a subchondral fragment when plate 410 is placed on radius 200. An example of beam 432 may include beam 132. Beam 432 may be comprised of any suitable material. For example, embodiments of beam 432 may be comprised of a bioabsorbable material, a non-bioabsorbable material, or a combination of both. Examples of materials for beam 432 may include, but are not limited to, metals such as titanium alloy. In some embodiments, beam 432 may also include radio-opaque materials to allow visualization on radiographs.

Positioning device 442 may include any device for traversing through opening 440 and engaging beam 432 when beam 432 is installed. One example of positioning device 442 may include positioning device 142. Positioning device 442 may be comprised of any suitable material. For example, embodiments of positioning device 442 may be comprised of a bioabsorbable material, a non-bioabsorbable material, or a combination of both. Examples of materials for positioning device 442 may include, but are not limited to, metals such as titanium alloy. In some embodiments, positioning device 442 may also include radio-opaque materials to allow visualization on radiographs.

In some embodiments, bone fixation system 400 may not include beams 432 and/or positioning devices 442. In some embodiments, openings 440 for positioning devices 442 may also receive fixation devices 422. For example, in one embodiment, openings 420a and 440 may be the same size. For example, fixation devices 422 and positioning devices 442 may have the same diameter, and openings 420a and 440 may receive either fixation devices 422 or positioning devices 440.

In the example of bone fixation system 400, plate 410 does not extend the full length of radius 200. Rather, plate 410 terminates where central column portion 414 meets lateral column portion 416. In this example, this termination point may correspond to a position near the pronator quadratus muscle on the distal forearm. Teachings of certain embodiments recognize that providing a plate 410 that terminates where central column portion 414 meets lateral column portion 416 may allow for a smaller incision area when compared to longer volar plates. Teachings of certain embodiments also recognize that bone fixation system 400 with plate 410 may be installed without moving the flexor pollicis longus muscle.

FIGS. 7A and 7B show a bone fixation system 400' according to one embodiment. FIG. 7A shows a top view, and FIG. 7B shows a bottom view. Bone fixation system 400' is similar to bone fixation system 400 except that bone fixation system 400' features a plate 410' in place of plate 410.

Similar to plate 410, plate 410' features a metaphasis portion 412, a central column portion 414, and a lateral column portion 416. In addition, plate 410' also features a shaft portion 418. Shaft portion 418 extends from the junction of central column portion 414 and lateral column portion 416 and is configured to conform to the diaphasis of radius 200. Shaft portion 418 may be of any suitable length. Example sizes of shaft portion 418 may include meta-diaphyseal, diaphyseal, and full length.

Shaft portion 418 may include any suitable openings. In one example embodiment, shaft portion 418 includes one opening 420a and a row of oblong openings 420b. In this example, the openings on shaft portion 418 are configured to receive fixation devices 422.

Figure 8A:
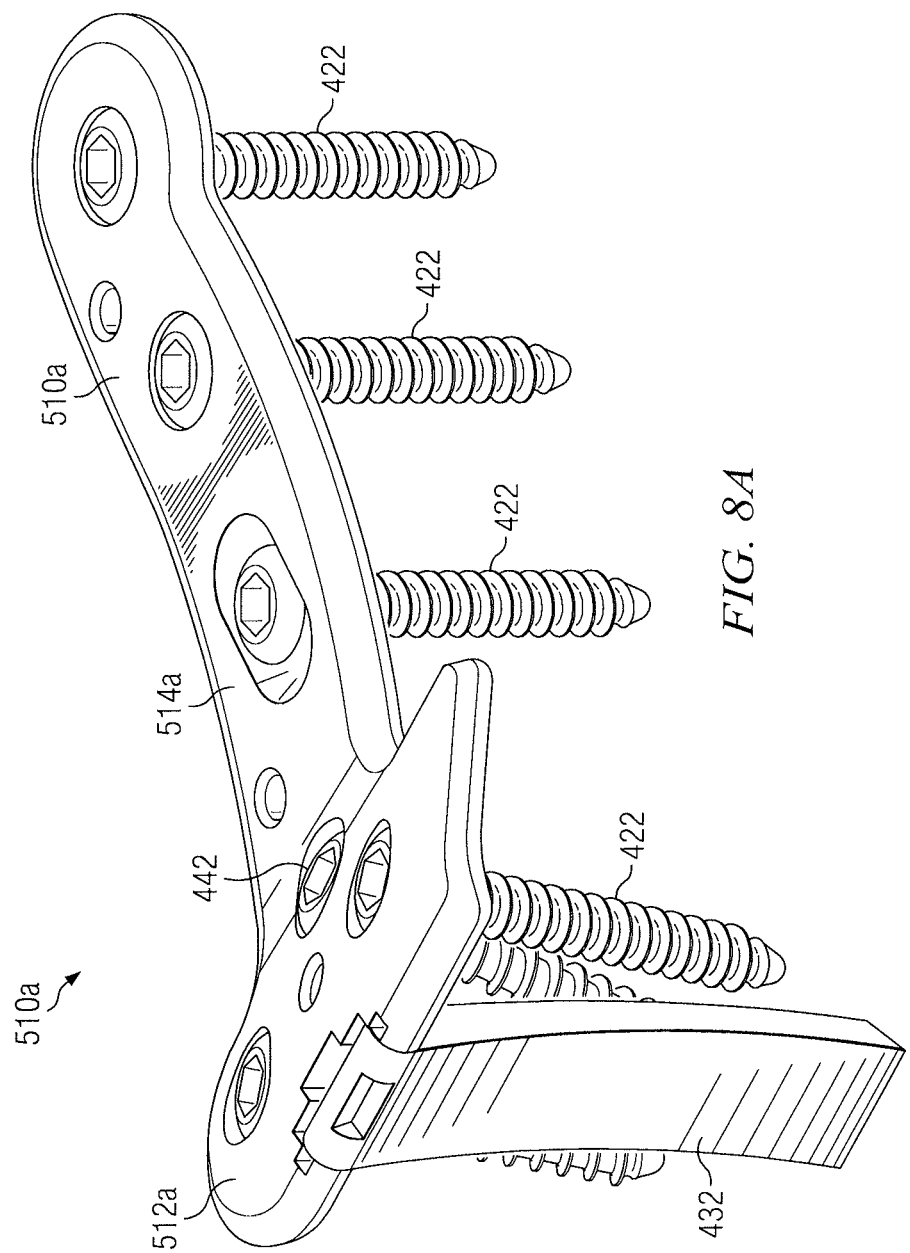
FIG. 8A shows a bone fixation system according to one embodiment.
Figure 8B:
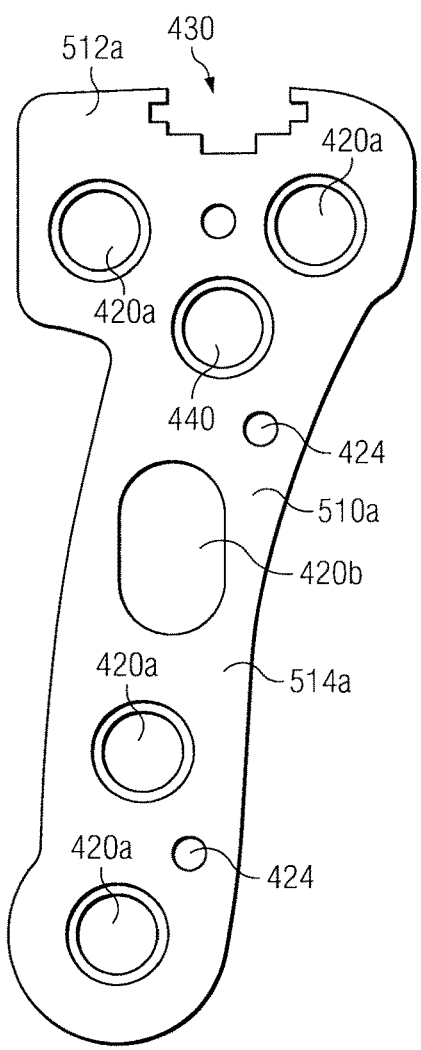
FIG. 8B shows a top view of the plate of FIG. 8A.

FIG. 8A shows a bone fixation system 500a according to one embodiment. Bone fixation system 500a is similar to bone fixation system 500 except that bone fixation system 500a features a plate 510a in place of plate 410. FIG. 8B shows a top view of plate 510a of FIG. 8A.

In this example embodiment, plate 510a includes a metaphysis portion 512a configured to conform to the metaphysis of radius 200 and a central column portion 514a configured to conform to the central column of the diaphysis of radius 200. Teachings of certain embodiments recognize that omitting a lateral column portion from plate 510a may allow for fixation of central column fractures with less hardware and effort.

Figure 9B:
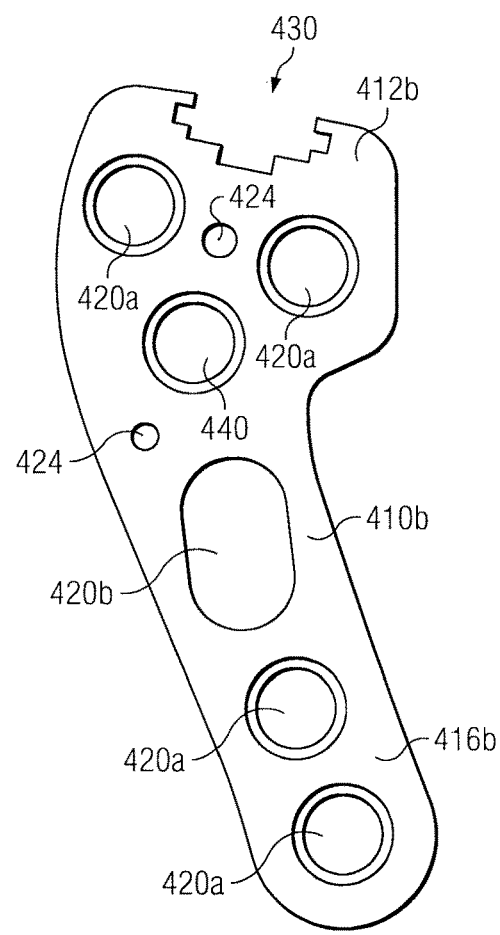
FIG. 9B shows a top view of the plate of FIG. 9A.

FIG. 9A shows a bone fixation system 500b according to one embodiment. Bone fixation system 500b is similar to bone fixation system 500 except that bone fixation system 500b features a plate 510b in place of plate 410. FIG. 9B shows a top view of plate 510b of FIG. 9A.

In this example embodiment, plate 510b includes a metaphysis portion 512b configured to conform to the metaphysis of radius 200 and a lateral column portion 516b configured to conform to the lateral column of the diaphysis of radius 200. Teachings of certain embodiments recognize that omitting a central column portion from plate 510b may allow for fixation of central column fractures with less hardware and effort.

In some embodiments, bone fixation systems 500a and 500b may be installed together on the same radius 200. Teachings of certain embodiments recognize that installing bone fixation systems 500a and 500b together may reduce effort necessary to treat some complex two-column fractures at one time.

Styloid Fixation Plates

Figure 10A:
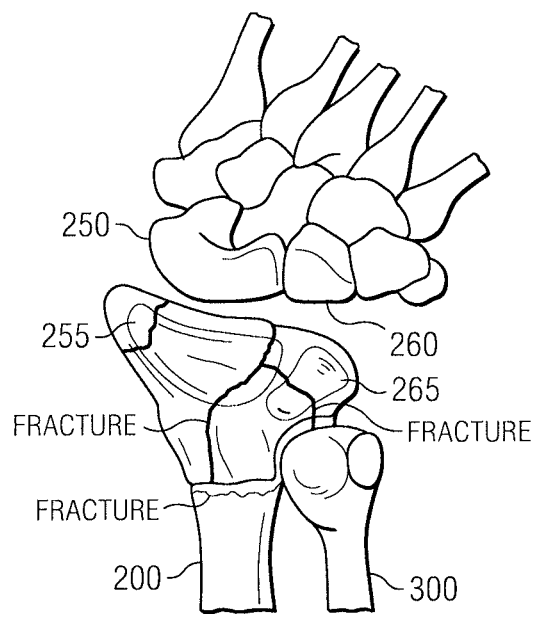
FIGS. 10A and 10B show additional views of the example radius and ulna of FIG. 5.
Figure 10B:
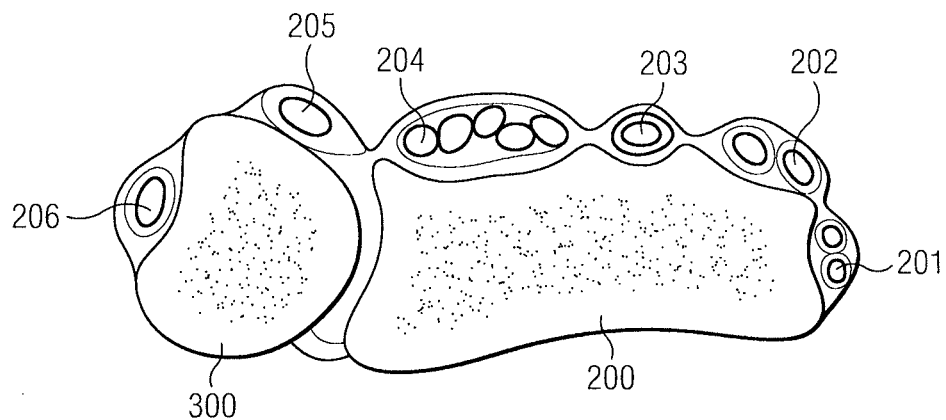
Figure 11B:
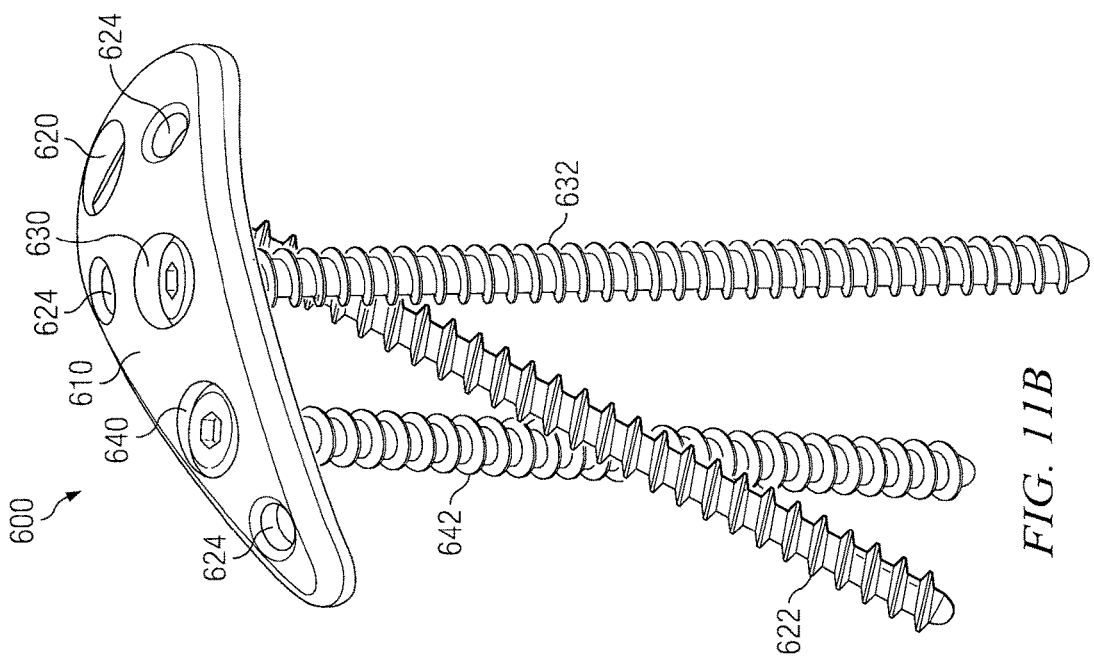
FIGS. 11A-11F show perspective views of a bone fixation system according to one embodiment.
Figure 11A:
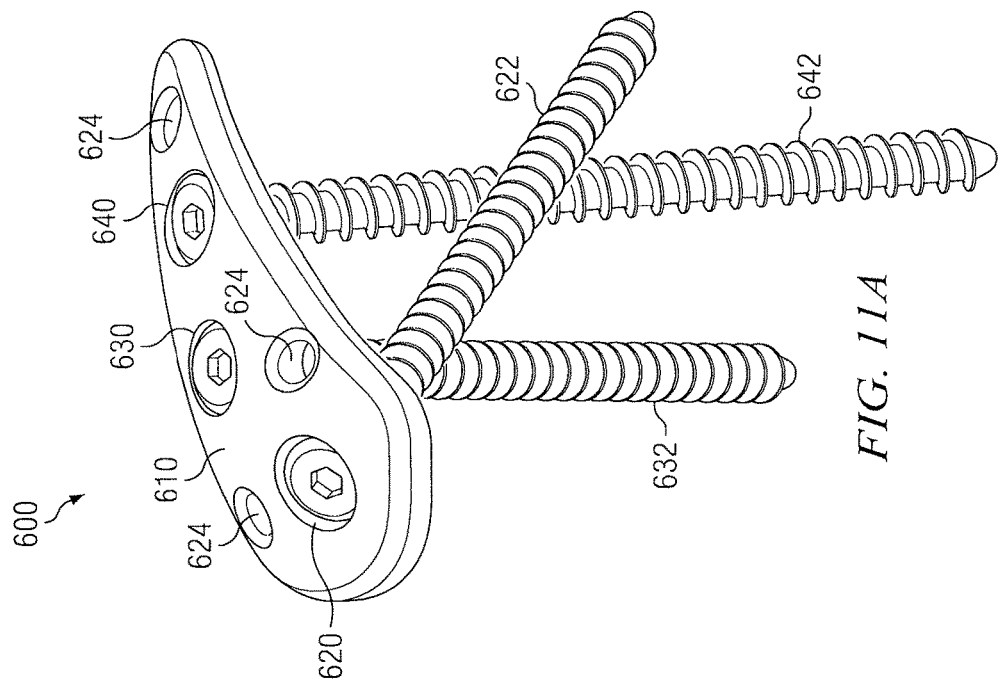
Figures 11C, 11D:
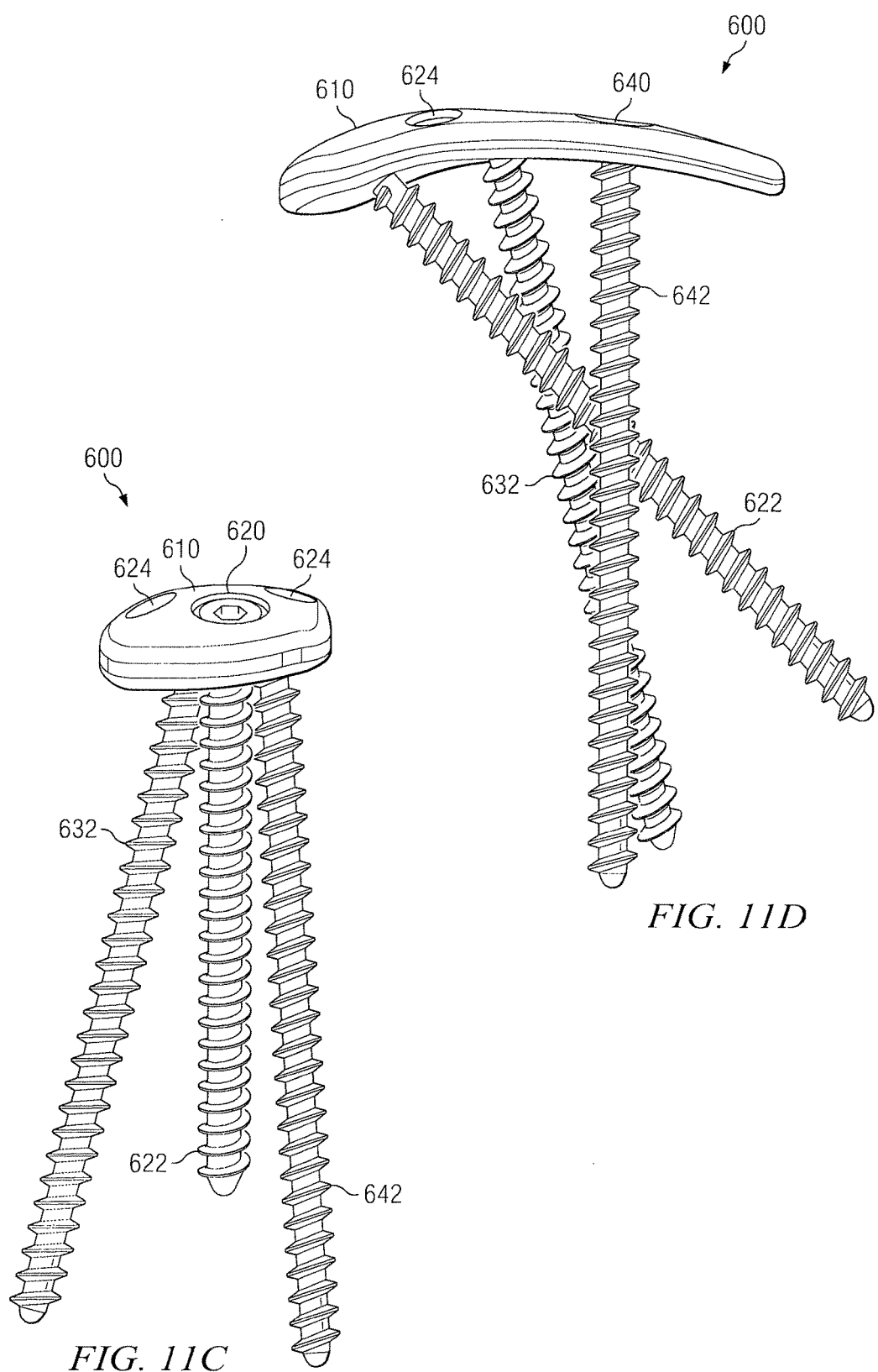
Figure 11E:
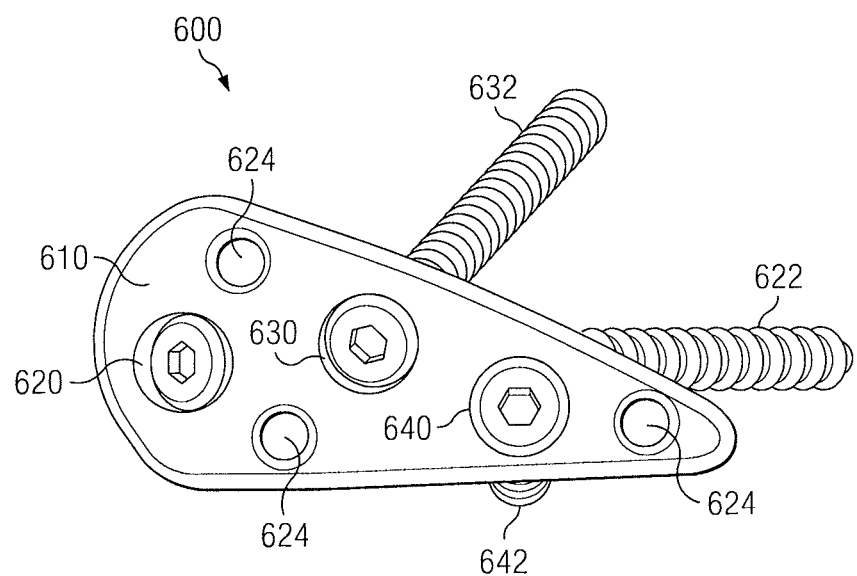
Figure 11F:
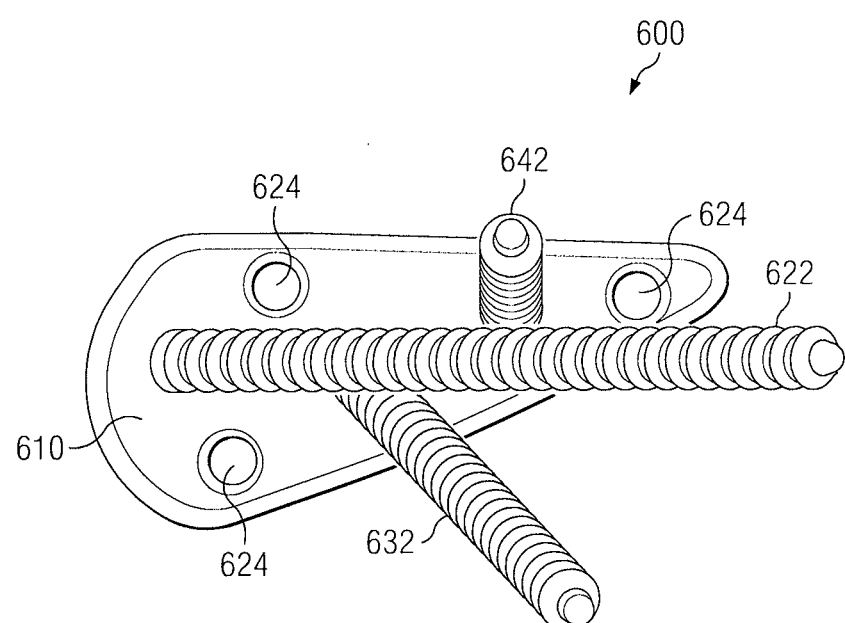

FIGS. 10A and 10B show additional views of the example radius 200 and ulna 300 of FIG. 5. FIG. 10A shows the relationship between radius 200 and scaphoid 250, scaphoid facet 255, lunate 260, and lunate facet 265. FIG. 10A also shows several distal fragments, including a radial styloid fragment.

FIG. 10B shows a crossectional view of radius 200, ulna 300, and extensor compartments 201-206. Extensor compartment 201 (first compartment) includes the extensor pollicis brevis and abductor pollicis longus tendons. Extensor compartment 202 (second compartment) includes the extensor carpi radialis longus and extensor carpi radialis brevis tendons. Extensor compartment 203 (third compartment) includes the extensor pollicis longus tendon. Extensor compartment 204 (fourth compartment) includes extensor digitorum muscle and the extensor indicis tendon. Extensor compartment 205 (fifth compartment) includes the extensor digiti minimi tendon. Extensor compartment 206 (sixth compartment) includes the extensor carpi ulnaris.

FIGS. 11A-11F show perspective views of a bone fixation system 600 according to one embodiment. FIGS. 12A and 12B show bone fixation system 600 installed on radius 200 between extensor compartment 201 and extensor compartment 202.

In some embodiments, bone fixation system 600 includes a plate 610 having one or more openings 620, 630, and 640, and one or more k-wire holes 624. Openings 620, 630, and 640 may receive fixation devices 622, 632, and 642.

Plate 610 may be dimensioned in any suitable manner. In some embodiments, the dimensions and contour of plate 610 is determined based on measurements from scans of a bone. As one example, plate 110 may be dimensioned based on measurements determined from a particular fractured bone. As another example, bones may be categorized according to size and/or contour, and different variations of plate 610 may be configured to conform to one or more of the different categories. Plate 610 may still be considered to conform to a bone even if such conformance is only approximate or imperfect. For example, plate 610 may be manufactured such that it generally conforms to a large number of bones in the population.

Plate 610 may be comprised of any suitable material. For example, embodiments of plate 610 may be comprised of a bioabsorbable material, a non-bioabsorbable material, or a combination of both. Examples of materials for plate 610 may include, but are not limited to, metals such as titanium alloy, polymers, and laminates. In some embodiments, plate 610 may also include radio-opaque materials to allow visualization on radiographs.

Plate 610 may include any number of openings, such as openings 620, 630, and 640. An opening may include any threaded or unthreaded, fixed or variable angle, locking or non-locking, partially or fully enclosed void in plate 610. In some embodiments, openings may be recessed such that they may receive a fixation device without the head of the fixation device extending above the surface of the plate.

In some embodiments, plate 610 may be configured to conform to radius 200. In the embodiment illustrated in FIGS. 12A and 12B, for example, plate 610 is configured to conform to radius 200 between extensor compartment 201 and extensor compartment 202. Teachings of certain embodiments recognize that configuring plate 610 between extensor compartment 201 and extensor compartment 202 may allow plate 610 to be installed without lifting or moving any tendon compartments.

In some embodiments, plate abut without violating extensor compartment 201 and/or extensor compartment 202. In one example embodiment, plate 610 may include an apex region configured to conform to radius 200 proximate to the intersect of extensor compartment 201 and extensor compartment 202. For example FIG. 12B shows extensor compartment 201 and extensor compartment 202 overlapping at an intersection, and plate 610 fits proximate to but without disrupting the intersection of extensor compartment 201 and extensor compartment 202.

Fixation devices 622, 632, and 642 may include any device for engaging radius 200. For example, in one embodiment, fixation device 122 is are screws or pegs operable to secure plate 610 to radius 200. Additional examples of fixation devices 622, 632, and 642 may include locking and non-locking smooth pegs, locking and non-locking cortical screws, and locking and non-locking cannulated compression screws.

In some embodiments, fixation device 622 may be configured to traverse through opening 620 and engage at least part of the radial styloid and/or the medial cortex of radius 200. In some embodiments, fixation devices 632 and 642 may be configured to traverse through opening 620 and engage at least part of the subchondral region of radius 200. Teachings of certain embodiments recognize that fixation devices 622, 632, and 642 together may stabilize the location of plate 610 relative to radius 200. For example, teachings of certain embodiments recognizing that using multiple fixation devices may prevent plate 610 from rotating.

Fixation devices 622, 632, and 642 may be comprised of any suitable material. For example, embodiments of fixation devices 622, 632, and 642 may be comprised of a bioabsorbable material, a non-bioabsorbable material, or a combination of both. Examples of materials for fixation devices 622, 632, and 642 may include, but are not limited to, metals such as titanium alloy. In some embodiments, fixation devices 622, 632, and 642 may also include radio-opaque materials to allow visualization on radiographs.

K-wire hole 624 may include any opening sized to receive a k-wire. A k-wire is a surgical pin that may provide temporary, provisional, and/or supplemental fixation. K-wires may be sterilized, sharpened, and/or smooth. K-wires may be composed of any suitable material, such as stainless steel. K-wires may be made of bioabsorbable or non-bioabsorbable materials.

In operation, plate 610 may be positioned on radius 200 between extensor compartment 201 and extensor compartment 202. Fixation device 622 may traverse through opening 620 into radius 200, such as the radial styloid and/or the medial cortex of radius 200. Fixation devices 632 and 642 may traverse through openings 630 and 640 into radius 200, such as subchondral regions of radius 200.

As explained above, bone fixation system 600 may provide fixation to the radial styloid of radius 200 as well as provide fixation for other types of fractures. Teachings of certain embodiments also recognize the capability to provide a volar plate to provide fixation of the ulnar styloid as well as other distal ulnar fractures.

Figure 13B:
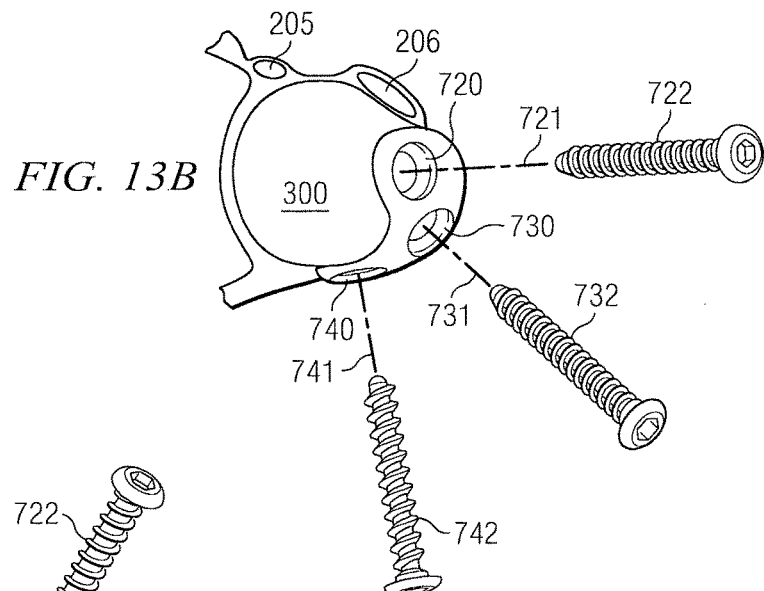
FIGS. 13A and 13B show perspective views of a bone fixation system according to one embodiment.
Figure 13A:
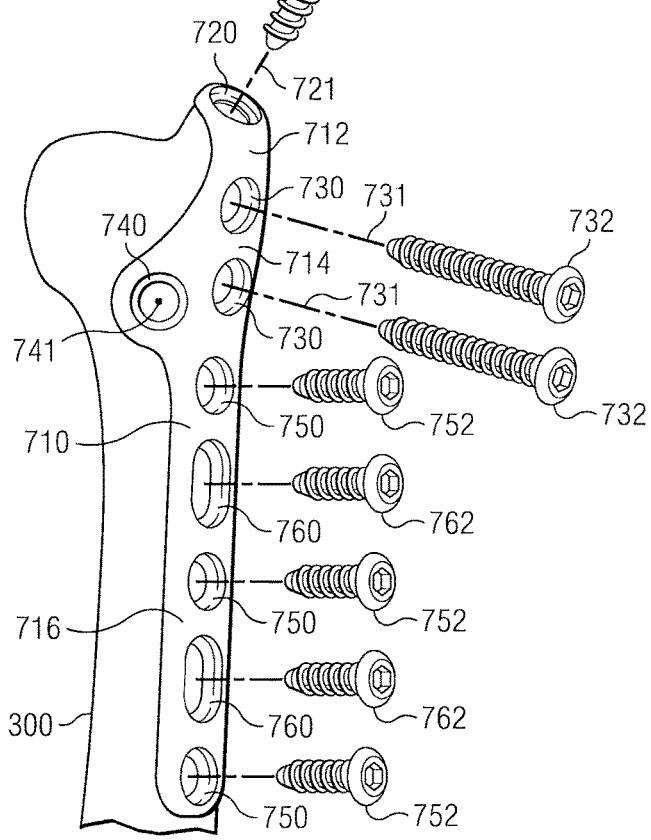

FIGS. 13A and 13B show perspective views of a bone fixation system 700 according to one embodiment. In some embodiments, bone fixation system 700 includes a plate 710 having a styloid tip portion 712, a head portion 714, and a shaft portion 716. In this example, styloid tip portion includes an opening 720, head portion 714 includes openings 730 and 740, and shaft portion 716 includes openings 750 and 760. Openings 720, 730, 740, 750, and 760 may receive fixation devices 722, 732, 742, 752, and 762.

Plate 710 may be comprised of any suitable material. For example, embodiments of plate 710 may be comprised of a bioabsorbable material, a non-bioabsorbable material, or a combination of both. Examples of materials for plate 110 may include, but are not limited to, metals such as titanium alloy, polymers, and laminates. In some embodiments, plate 710 may also include radio-opaque materials to allow visualization on radiographs.

In some embodiments, plate 710 may be configured to conform to the volar side of ulna 300. In the embodiment illustrated in FIGS. 13A-13B, for example, plate 710 includes a styloid tip portion 712, a head portion 714, and a shaft portion 716. In this example, styloid tip portion 710 is configured to conform to the ulnar styloid of ulna 300; head portion 714 is configured to conform to the head of ulna 300; and shaft portion 716 is configured to conform to the shaft of ulna 300.

Plate 710 may be dimensioned in any suitable manner. In some embodiments, the dimensions and contour of plate 710 is determined based on measurements from scans of a bone. As one example, plate 710 may be dimensioned based on measurements determined from a particular fractured bone. As another example, bones may be categorized according to size and/or contour, and different variations of plate 710 may be configured to conform to one or more of the different categories. Plate 710 may still be considered to conform to a bone even if such conformance is only approximate or imperfect. For example, plate 710 may be manufactured such that it generally conforms to a large number of bones in the population, each of which may have a unique shape.

The outer boundaries of plate 710 may have any suitable dimensions. In one example embodiment, styloid tip portion 712 is dimensioned to conform to ulna 300 such that ulna 300 does not violate extensor compartment 206, the distal radio-ulnar joint, and/or the pronator quadratus muscle.

Plate 710 may include any number of openings, such as openings 720, 730, 740, 750, and 760. An opening may include any threaded or unthreaded, fixed or variable angle, locking or non-locking, partially or fully enclosed void in plate 710. In some embodiments, openings may be recessed such that they may receive a fixation device without the head of the fixation device extending above the surface of the plate. In the example embodiment of FIGS. 13A-13B, openings 720, 730, 740, 750, and 760 are configured to receive fixation devices 722, 732, 742, 752, and 762.

In some embodiments, styloid tip portion 712 includes opening 720. In some embodiments, styloid tip portion 712 is configured to conform to the ulnar styloid of ulna 300, and opening 720 is oriented relative to styloid tip portion 712 such that axis 721 projects through opening 720 and the ulnar styloid. Opening 720 may be configured to receive fixation device 722 along axis 721. Axis 721 may project through any portion of opening 720 and is not necessarily in the center of opening 720.

In some embodiments, head portion 714 includes openings 730 and 740. In some embodiments, head portion 714 is configured to conform to the head of ulna 300. Opening 730 may be oriented relative to head portion 714 such that axis 731 projects through opening 730 and the head of ulna 300, and opening 740 may be oriented relative to head portion 714 such that axis 741 projects through opening 740 and the head of ulna 300. Opening 730 may be configured to receive fixation device 732 along axis 731, and opening 740 may be configured to receive fixation device 742 along axis 741.

In some embodiments, axis 741 projects between extensor compartments 205 and 206, as shown in FIG. 13B. In some embodiments, axis 731 is skew to axis 741 such that they are not intersecting and are not parallel, as shown in FIGS. 13A and 13B. In the example of FIGS. 13A and 13B, head portion 714 includes two openings 730 having parallel axis 731.

In some embodiments, shaft portion 716 includes openings 750 and 760. In some embodiments, shaft portion 716 is configured to conform to the shaft of ulna 300. Opening 750 may be oriented relative to head portion 714 such that axis 751 projects through opening 750 and the head of ulna 300, and opening 760 may be oriented relative to head portion 714 such that axis 761 projects through opening 760 and the head of ulna 300. Opening 750 may be configured to receive fixation device 752 along axis 761, and opening 760 may be configured to receive fixation device 762 along axis 761.

In the example of FIG. 13A, openings 750 and 760 are coplanar and/or collinear. In this example, however, openings 730 are not collinear with openings 750 and 760.

Fixation devices 722, 732, 742, 752, and 762 may include any device for engaging ulna 300. Examples of fixation devices 722, 732, 742, 752, and 762 may include fixation devices 122 and 422. In some embodiments, at least some of fixation devices 722, 732, 742, 752, and 762 are screws or pegs operable to secure plate 710 to ulna 300. Additional examples of fixation devices 722, 732, 742, 752, and 762 may include locking and non-locking smooth pegs, locking and non-locking cortical screws, and locking and non-locking cannulated compression screws. In some embodiments, fixation devices 722, 732, 742, 752, and 762 may be similar or the same, such as having similar diameters, threads, and lengths.

Fixation devices 722, 732, 742, 752, and 762 may be comprised of any suitable material. For example, embodiments may be comprised of a bioabsorbable material, a non-bioabsorbable material, or a combination of both. Examples of materials may include, but are not limited to, metals such as titanium alloy. Some embodiments may also include radio-opaque materials to allow visualization on radiographs.

In some embodiments, openings 720, 730, 740, and/or 750 may be defined by a threaded hole in plate 710. In these embodiments, fixation devices may have a threaded head portion configured to engage the threaded hole. In some embodiments, fixation devices also include a threaded shaft portion for engaging ulna 300.

In some embodiments, opening 760 may be an oblong opening. Teachings of certain embodiments recognize that an oblong opening may aid in positioning a plate on a bone and may be used to provide compression. For example, plate 710 may be attached to ulna 300 by inserting fixation devices 762 through oblong openings 760 to engage bone. Plate 710 may then be repositioned relative to ulna 300, allowing fixation device 762 to move relative to oblong opening 760. Once plate 710 is in a suitable position, fixation device 762 may be tightened to ulna 300.

Figure 14A:
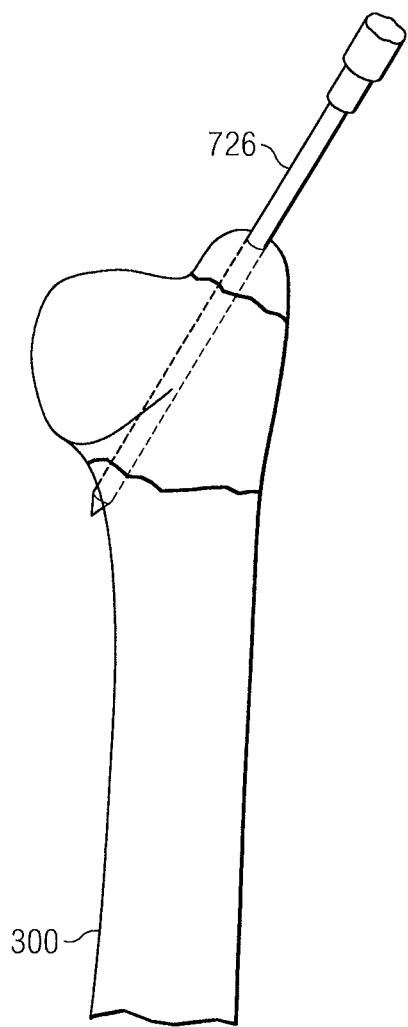
FIGS. 14A-14D show progressive views of the bone fixation system of FIGS. 13A and 13B being installed on the ulna of FIG. 5 according to one embodiment.
Figure 14B:
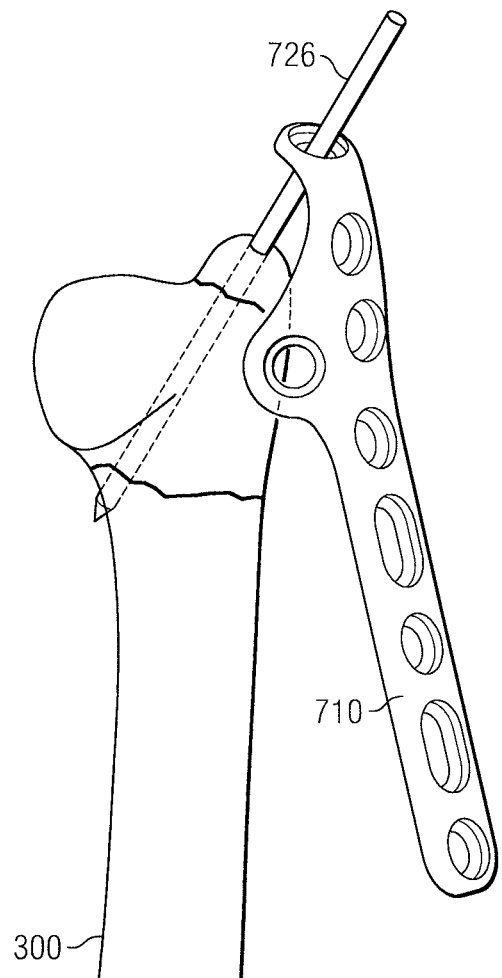
Figure 14C:
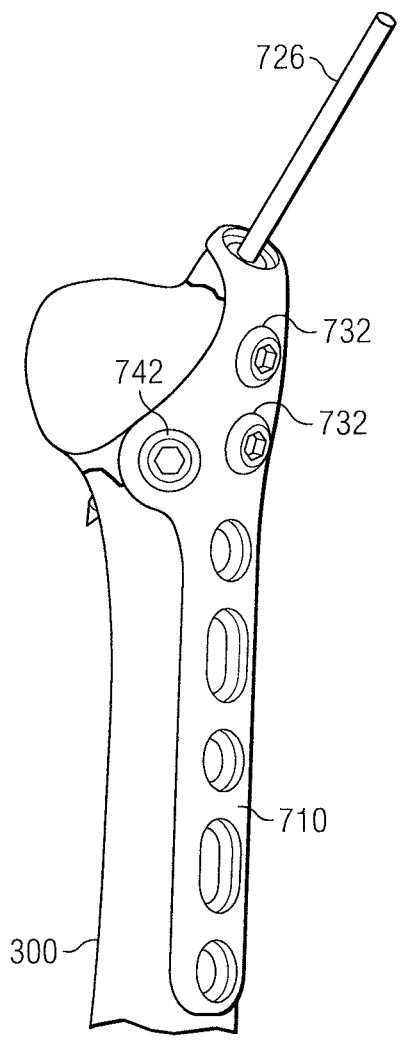
Figure 14D:
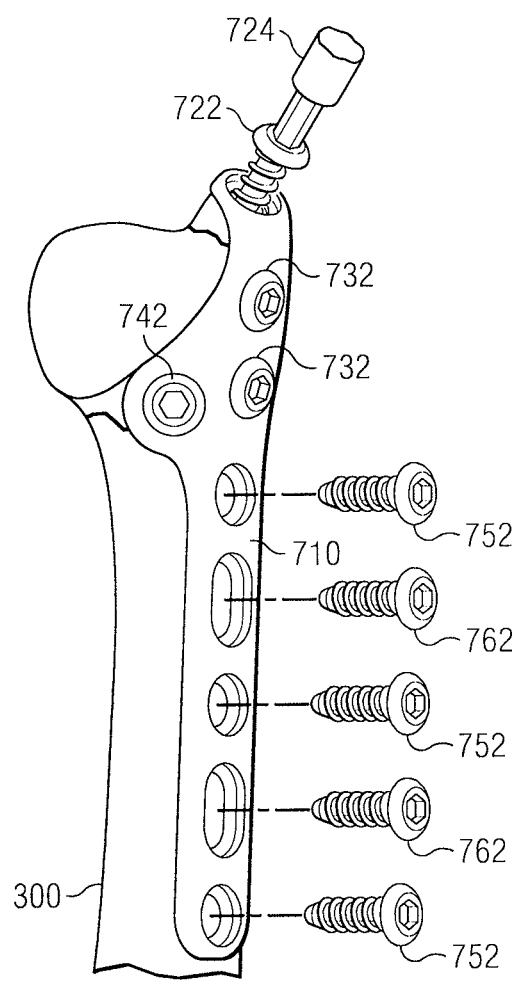

FIGS. 14A-14D show progressive views of the bone fixation system 700 being installed on ulna 300 according to one embodiment. In FIG. 14A, a k-wire 726 is inserted to provide provisional fixation of an ulnar styloid fragment to ulna 300. In FIG. 14B, plate 710 is provided such that k-wire 726 moves through opening 720 and plate 710 moves towards ulna 300. In FIG. 14C, fixation devices 732 and 742 are provided through openings 730 and 740. In FIG. 14D, k-wire 726 is removed, and fixation device 722 is provided through opening 720 using a driver 724.

Figure 15D:
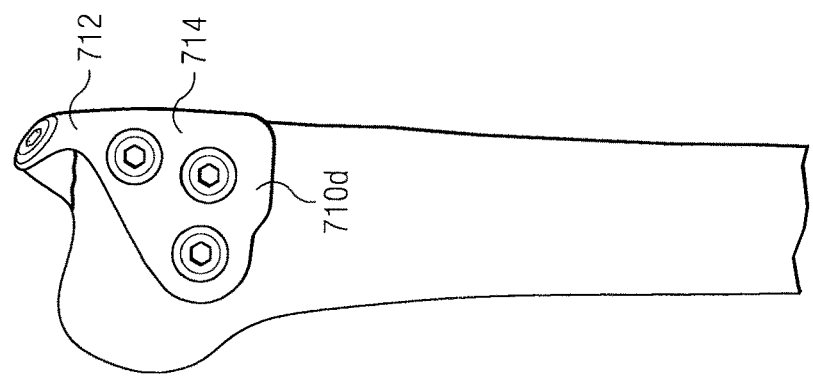
FIGS. 15A-15D show variations of the plate of the bone fixation system of FIGS. 13A and 13B installed on different fractured ulnas.
Figure 15C:
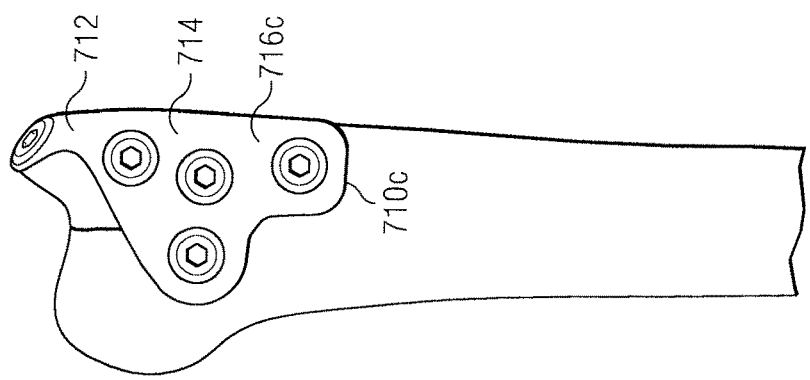
Figure 15B:
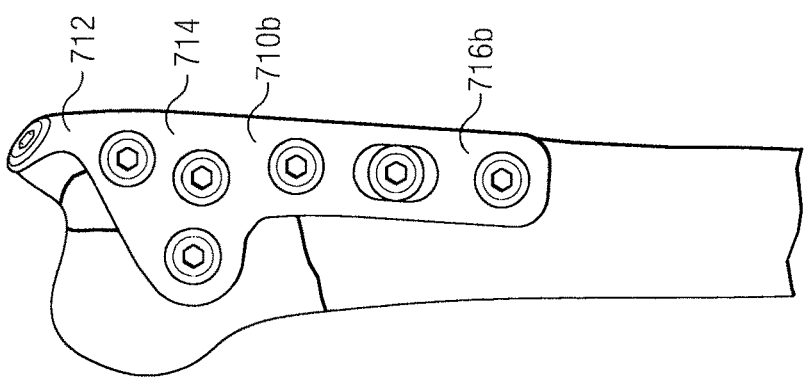
Figure 15A:
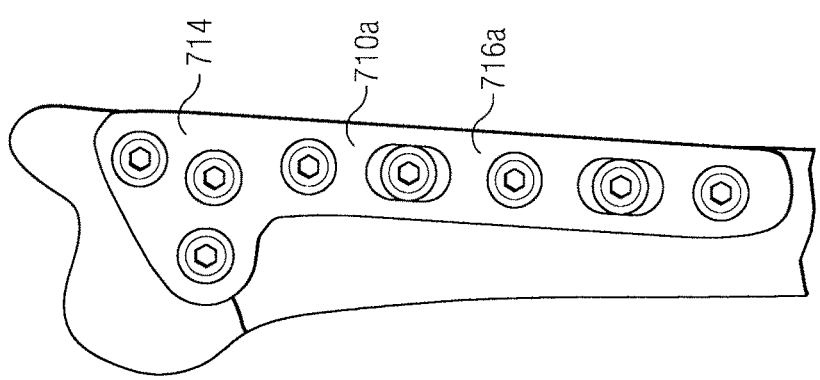

FIGS. 15A-15D show variations of plate 710 installed on different fractured ulnas. FIG. 15A shows a plan view of plate 710a installed on ulna 300a. Unlike plate 710, plate 710a does not include a styloid tip portion 712. Teachings of certain embodiments recognize that styloid tip portion 712 may be removed if the styloid of ulna 300 is not fractured. In some embodiments, styloid tip portion 712 may be removed from plate 710 to yield plate 710a. In other embodiments, plate 710a is manufactured without a styloid tip portion 712.

FIG. 15B shows a plan view of plate 710b installed on ulna 300b. Unlike plate 710, plate 710b features a shaft portion 716b with only three openings. Teachings of certain embodiments recognize that shaft length may be modified depending on where fractures are located on ulna 300. For example, teachings of certain embodiments recognize a plate 710 may be stabilized against ulna 300 as long as three openings in plate 710 are provided proximal to the fracture in ulna 300. Thus, in the example of FIG. 15B, and shaft portion provides three openings proximal to the fractures in ulna 300b.

FIG. 15C shows a plan view of plate 710c installed on ulna 300c. Unlike plate 710, plate 710c features a shaft portion 716b with only one opening. As explained above, teachings of certain embodiments recognize a plate 710 may be stabilized against ulna 300 as long as three openings in plate 710 are provided proximal to the fracture in ulna 300. Thus, in the example of FIG. 15C, head portion 714 provides two openings proximal to the fracture in ulna 300b, and shaft portion provides one opening proximal to the fracture in ulna 300b.

FIG. 15D shows a plan view of plate 710d installed on ulna 300d. Unlike plate 710, plate 710d does not have a shaft portion 716. In this example, head portion 714 provides three openings proximal to the fracture in ulna 300c, thus allowing shaft portion 716 to be removed in some embodiments.

As noted above, in some embodiments plates 710a-710d may be modified from plate 710 by removing portions such as styloid tip portion 712 and/or some or all of shaft portion 716. Portions may be removed from plate 710 in any suitable manner. In some embodiments, portions may be removed by cutting or breaking off pieces from plate 710. In some embodiments, plate 710 may include perforations, indentations, or weaknesses allowing portions of plate 710 to be removed more easily. For example, in some embodiments plate 710 may include a perforation between styloid tip portion 712 and head portion 714 that enables styloid tip portion 712 to be removed without machine tools.

Dorsal Plates

As explained above, volar fixation systems such as bone fixation systems 400, 500a, 500b, 600, and 700 may provide fixation to a variety of bone fractures by attaching to the volar side of radius 200 and/or ulna 300. Teachings of certain embodiments also recognize the capability to provide fixation and/or fusion to the dorsal side of radius 200 and/or ulna 300.

Figure 16A:
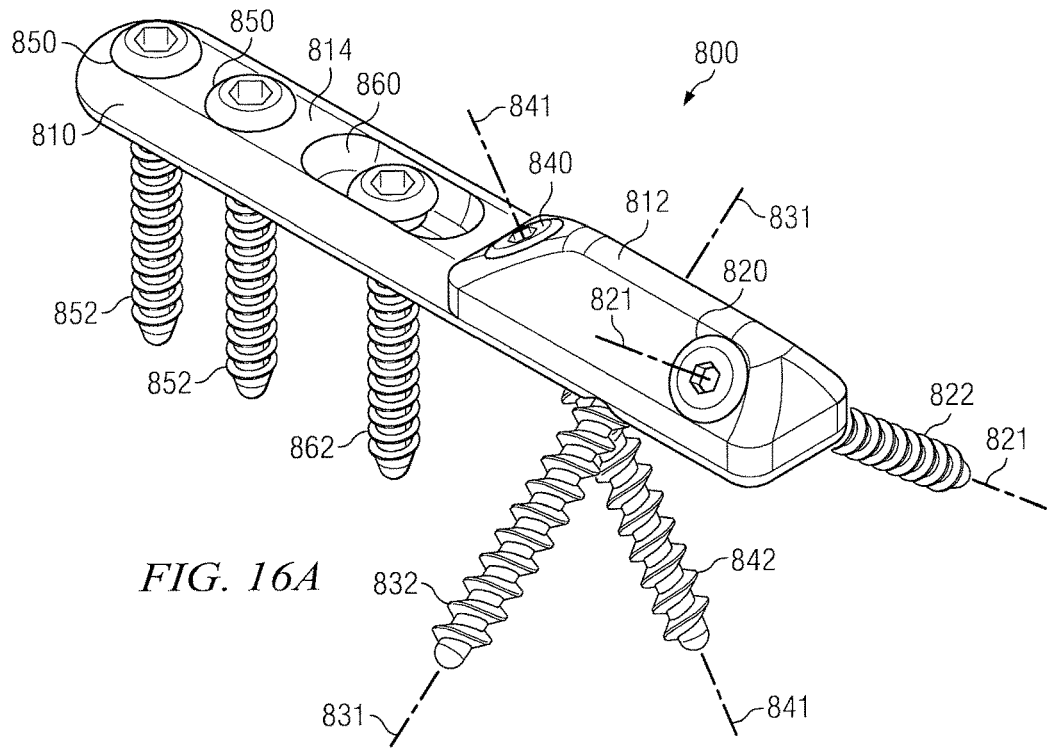
FIGS. 16A-16G show a bone fixation system according to one embodiment.
Figure 16B:
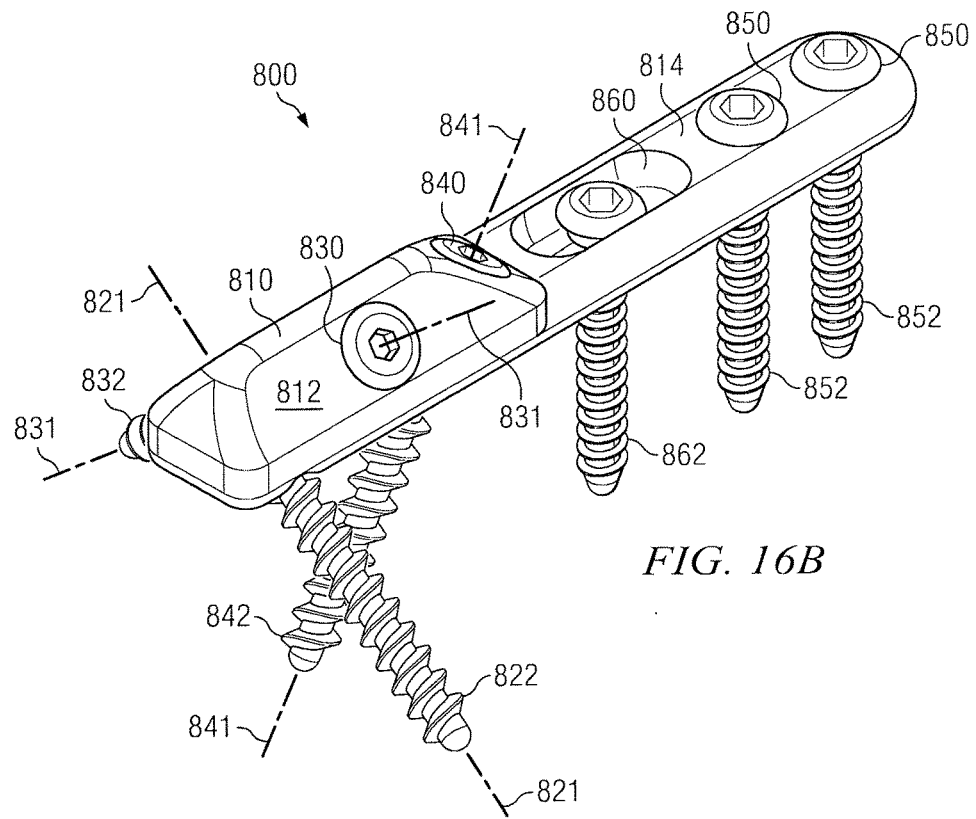
Figure 16C:
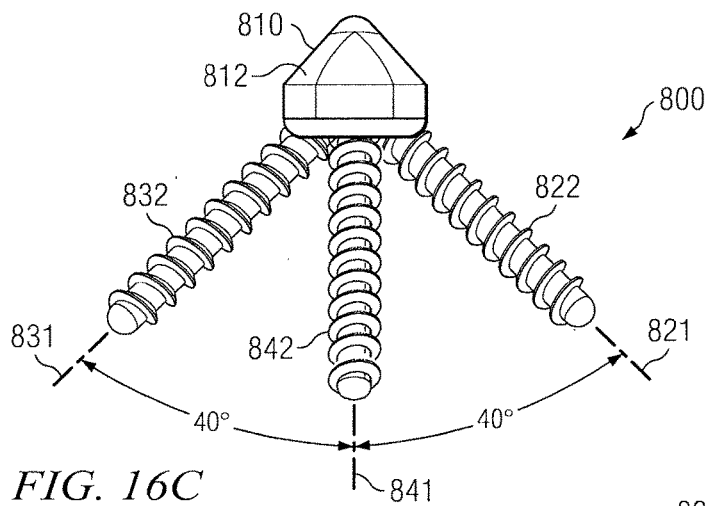
Figure 16D:
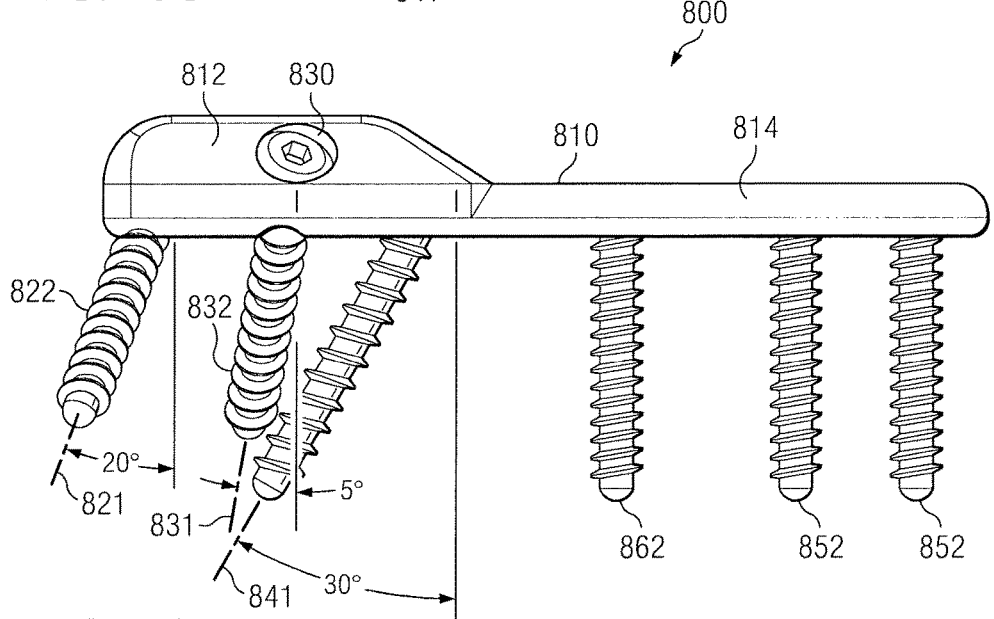
Figure 16E:
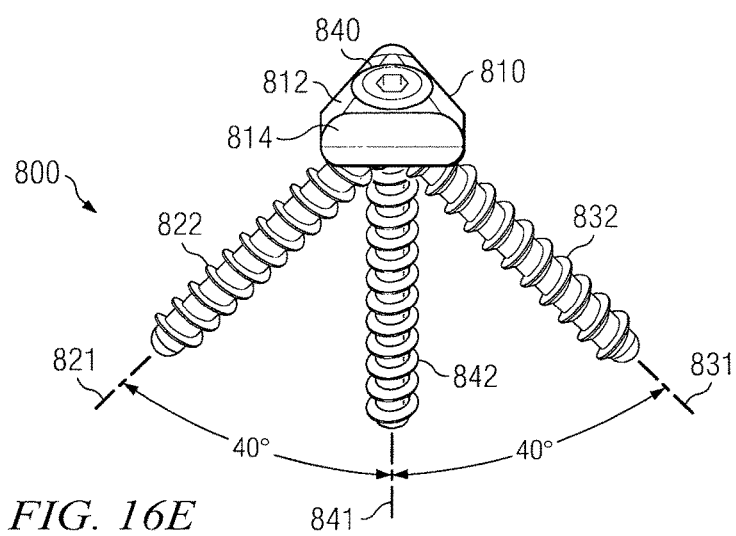
Figure 16F:
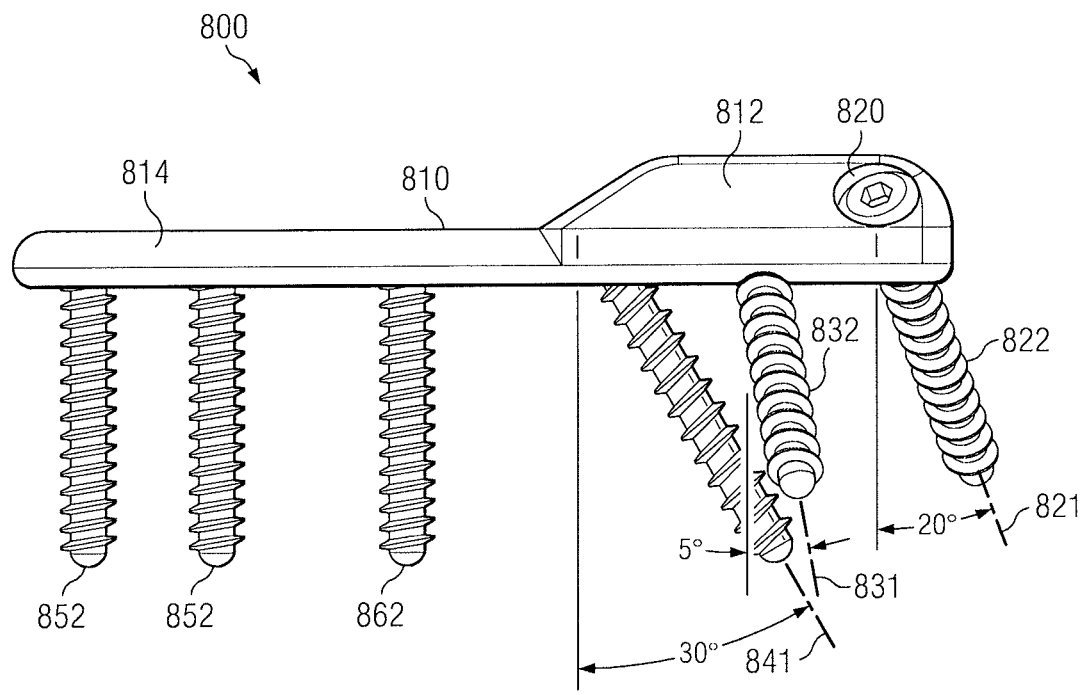
Figure 16G:
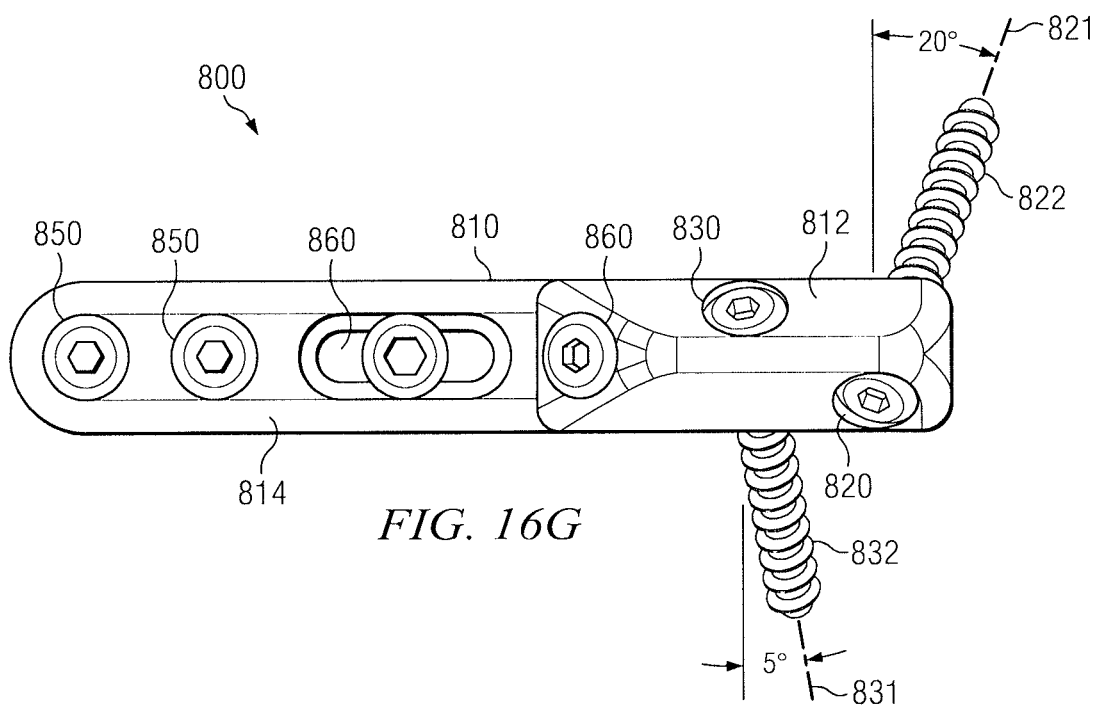

FIGS. 16A-16G show a bone fixation system 800 according to one embodiment. FIGS. 16A and 16B show perspective views of bone fixation system 800, FIG. 16C shows a distal end of bone fixation system 800, FIG. 16D shows a side view of bone fixation system 800, FIG. 16E shows a distal end of bone fixation system 800, FIG. 16F shows a side view of bone fixation system 800 opposite from FIG. 16D, and FIG. 16G shows a top view of bone fixation system 800.

In some embodiments, bone fixation system 800 includes a plate 810 having one or more openings 820, 830, 840, 850, and 860. In operation, bone fixation system 800 may be installed on radius 200 between compartment 202 and compartment 204.

Plate 810 may be dimensioned in any suitable manner. In some embodiments, the dimensions and contour of plate 810 is determined based on measurements from scans of a bone. As one example, plate 810 may be dimensioned based on measurements determined from a particular fractured bone. As another example, bones may be categorized according to size and/or contour, and different variations of plate 810 may be configured to conform to one or more of the different categories. Plate 810 may still be considered to conform to a bone even if such conformance is only approximate or imperfect. For example, plate 810 may be manufactured such that it generally conforms to a large number of bones in the population.

Plate 810 may be comprised of any suitable material. For example, embodiments of plate 810 may be comprised of a bioabsorbable material, a non-bioabsorbable material, or a combination of both. Examples of materials for plate 810 may include, but are not limited to, metals such as titanium alloy, polymers, and laminates. In some embodiments, plate 810 may also include radio-opaque materials to allow visualization on radiographs.

Plate 810 may include any number of openings, such as openings 820, 830, 840, 850, and 860. An opening may include any threaded or unthreaded, fixed or variable angle, locking or non-locking, partially or fully enclosed void in plate 810. In some embodiments, openings may be recessed such that they may receive a fixation device without the head of the fixation device extending above the surface of the plate.

In some embodiments, plate 810 may be configured to conform to radius 200. In particular, plate 810 may be configured to conform to radius 200 between extensor compartment 202 and extensor compartment 204. Teachings of certain embodiments recognize that plate 810 may be installed between extensor compartment 202 and extensor compartment 204 by moving some or all of the contents of extensor compartment 203, as will be explained in greater detail below.

In the example of FIGS. 16A-16G, plate 810 includes a fixation portion 812 and a shaft portion 814. In this example, fixation portion 812 and shaft portion 814 are configured to conform to radius 200 between extensor compartment 202 and extensor compartment 204.

As shown in FIGS. 16A-16G, fixation portion 812 may include openings 820, 830, and 840; and shaft portion 814 includes openings 850 and 860. In some embodiments, at least some of openings 820, 830, 840, 850, and 860 may be generally collinear and/or coplanar. For example, in FIGS. 16A-16G, openings 820, 830, 840, 850, and 860 are drawn to be collinear as a reference line may be drawn intersecting openings 820, 830, 840, 850, and 860. In this example, openings 820, 830, 840, 850, and 860 are also coplanar as a reference plane may be drawn through axis 841 and openings 820, 830, 840, 850, and 860. In this example, the reference plane may be defined by axis 841 and by an opening 850.

In some embodiments, fixation portion 812 includes openings 820, 830, and 840. Openings 820, 830, and 840 may be configured to receive fixation devices 822, 832, and 842 respectively. In some embodiments, fixation device 822 may traverse through opening 820 along axis 821, fixation device 832 may traverse through opening 830 along axis 831, and fixation device 842 may traverse through opening 840 along axis 841.

In the example of FIGS. 16A-16G, axes 821, 831, and 841 are skew in that they are not parallel and are not intersecting. In this example, axes 821 and 831 are not generally coplanar with the reference plane defined by axis 841 and opening 850.

In this example, opening 820 is oriented such that when plate 810 is installed against radius 200 and fixation device 822 is received along axis 821, fixation device 822 may provide fixation into the styloid of radius 200 and/or provide subchondral support to the scaphoid facet 255. Also in this example, opening 830 is oriented such that when plate 810 is installed against radius 200 and fixation device 832 is received along axis 831, fixation device 832 may provide subchondral support to the lunate facet 265.

In this example, opening 840 is oriented such that when plate 810 is installed against radius 200 and fixation device 842 is received along axis 841, fixation device 842 may provide fixation into a distal fragment of radius 200. In some embodiments, opening 840 is oriented such that when fixation device 842 is received along axis 841, the tip of fixation device 842 is positioned distal to the head of fixation device 842. Thus, axis 841 may be oriented at an obtuse angle relative to shaft portion 814. In the example of FIGS. 16A-16G, axis 841 is oriented at a 120 degree angle relative to shaft portion 814.

In some embodiments, shaft portion 814 includes openings 850 and 860. Openings 850 and 860 may be configured to receive fixation devices 852 and 862 respectively. In some embodiments, fixation device 852 may traverse through opening 850 along axis 851, and fixation device 862 may traverse through opening 860 along axis 861.

Fixation devices 822, 832, 842, 852, and 862 may include any device for engaging radius 200. Examples of fixation devices 822, 832, 842, 852, and 862 may include fixation devices 122 and 422. In some embodiments, at least some of fixation devices 822, 832, 842, 852, and 862 are screws or pegs operable to secure plate 810 to radius 200. Additional examples of fixation devices 822, 832, 842, 852, and 862 may include locking and non-locking smooth pegs, locking and non-locking cortical screws, and locking and non-locking cannulated compression screws. In some embodiments, fixation devices 822, 832, 842, 852, and 862 may be similar or the same, such as having similar diameters, threads, and lengths.

Fixation devices 822, 832, 842, 852, and 862 may be comprised of any suitable material. For example, embodiments may be comprised of a bioabsorbable material, a non-bioabsorbable material, or a combination of both. Examples of materials may include, but are not limited to, metals such as titanium alloy. Some embodiments may also include radio-opaque materials to allow visualization on radiographs.

In some embodiments, openings 820, 830, 840, and/or 850 may be defined by a threaded hole in plate 810. In these embodiments, fixation devices may have a threaded head portion configured to engage the threaded hole. In some embodiments, fixation devices also include a threaded shaft portion for engaging radius 200.

In some embodiments, opening 860 may be an oblong opening. Teachings of certain embodiments recognize that an oblong opening may aid in positioning a plate on a bone and may be used to provide compression. For example, plate 810 may be attached to radius 200 by inserting fixation devices 862 through oblong openings 860 to engage bone. Plate 810 may then be repositioned relative to radius 200, allowing fixation device 862 to move relative to oblong opening 860. Once plate 810 is in a suitable position, fixation device 862 may be tightened to radius 200.

Figure 17A:
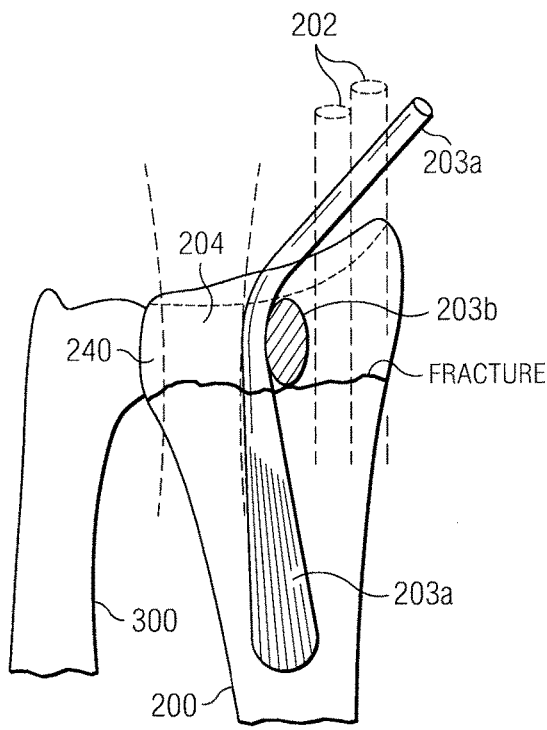
FIGS. 17A-17G show progressive views of the bone fixation system of FIGS. 16A-16G being installed on the radius of FIG. 5 according to one embodiment.

FIGS. 17A-17G show progressive views of bone fixation system 800 being installed on radius 200 according to one embodiment. In FIG. 17A, radius 200 is shown with compartments 202, 203, and 204. In this example, compartment 203 also includes EPL tendon 203*a* and Lister's Tubercle 203*b*. In FIG. 17A, radius 200 is shown having a fractured fragment 240.

Figure 17B:
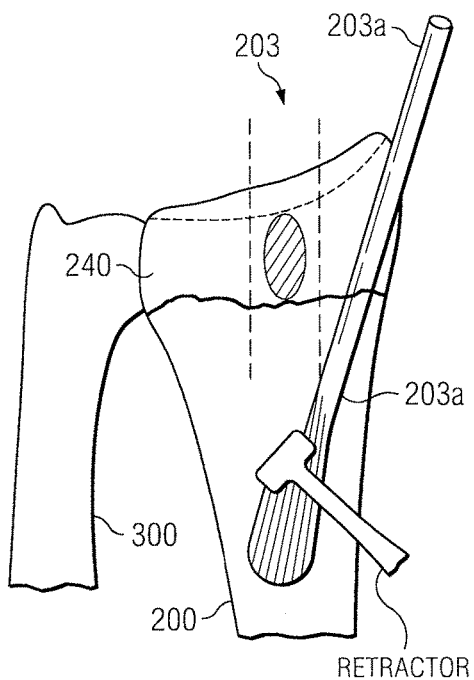
Figure 17C:
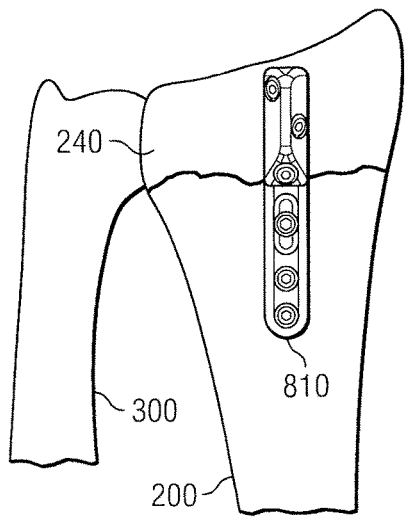

In FIG. 17B, Lister's Tubercle 203*b* is removed, and EPL tendon 203*a* is transposed out of compartment 203. In FIG. 17C, plate 810 is placed on radius 200. In this example, plate 810 is placed in compartment 203 over the former location of Lister's Tubercle 203*b*.

Figure 17D:
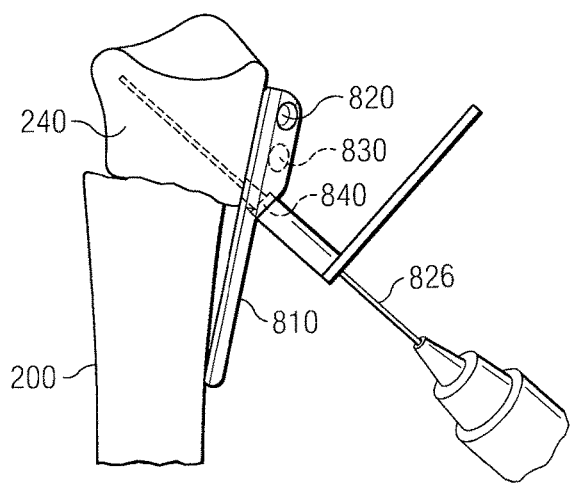
Figure 17E:
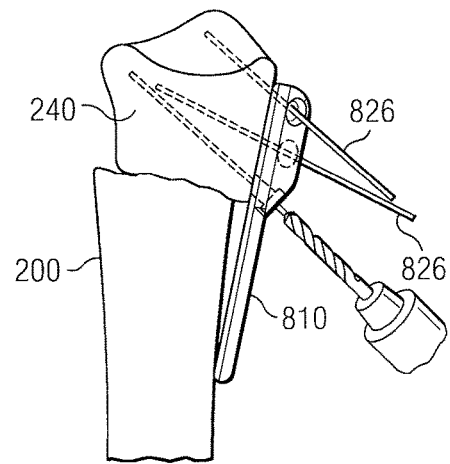

In FIG. 17D, a k-wire 826 is driven through opening 840 to provide provisional fixation to fragment 240. In FIG. 17E, k-wires 826 are also driven through openings 820 and 830 to provide additional fixation to fragment 240.

Figure 17F:
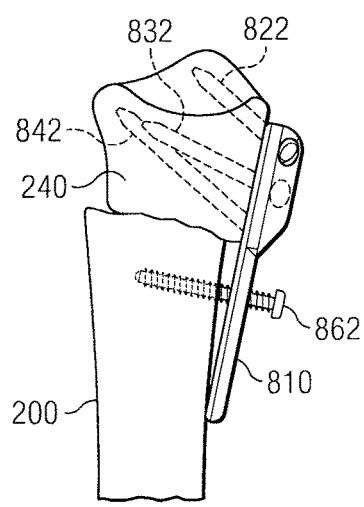
Figure 17G:
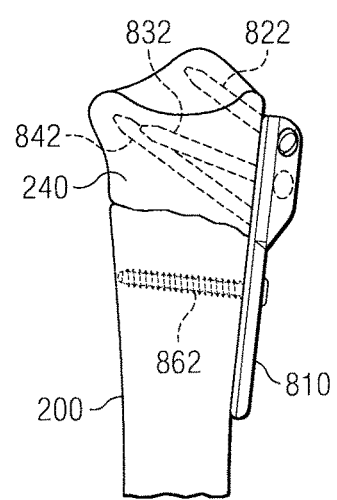

In FIG. 17F, k-wires 826 are removed, and fixation devices 822, 832, and 842 are inserted through openings 820, 830, and 840 to engage fragment 240. Fixation device 862 is also inserted through opening 860 to engage radius 200. In this example, fixation device 862 is partially inserted so as to allow plate 810 to move relative to radius 200. In FIG. 17G, plate 810 is repositioned, and fixation device 862 is tightened against radius 200. Teachings of certain embodiments recognize that fixation device 862 provides an efficient mechanism by reducing the fracture between fragment 240 and radius 200 by pulling plate 810 towards radius 200. Thus, in this example, plate 810 acts as a buttress for translation of fragment 240 after fixation device 862 is tightened.

Figure 18A:
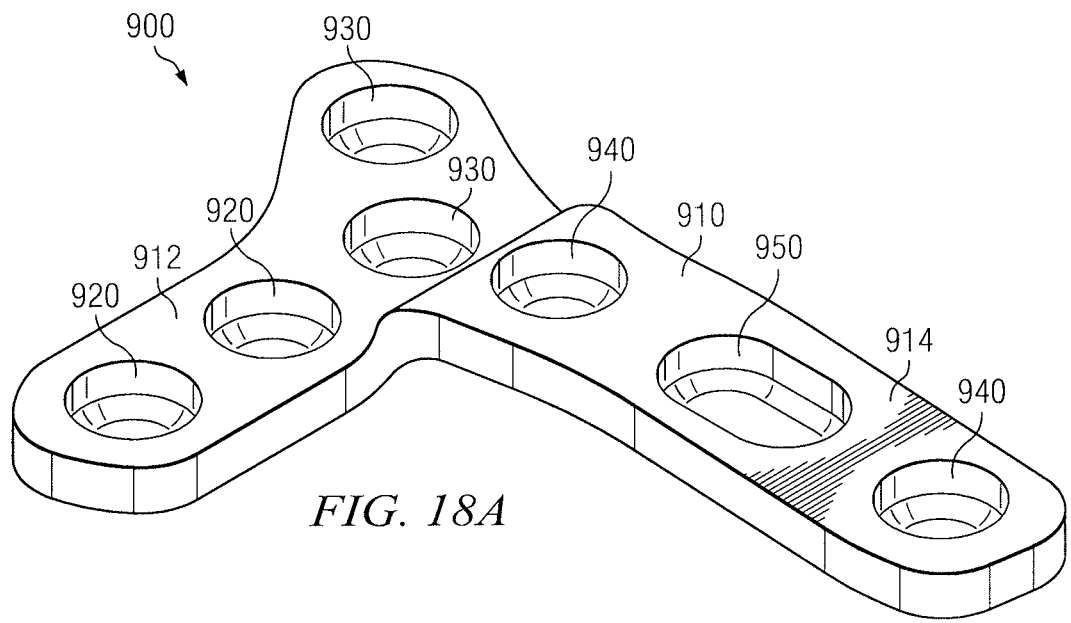
FIGS. 18A and 18B show a bone fusion system according to one embodiment.
Figure 18B:
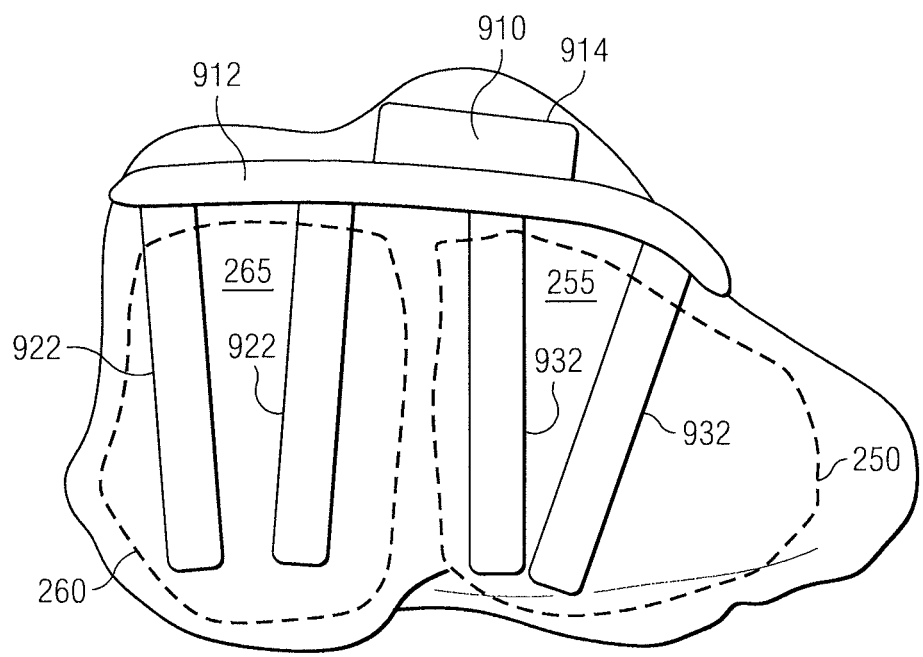

FIGS. 18A and 18B show a bone fusion system 900 according to one embodiment. FIG. 18A shows plate 910 of bone fusion system 900, and FIG. 18B shows bone fusion system 900 installed against scaphoid 250 and lunate 260. In operation, plate 910 may be secured to radius 200, scaphoid 250, and lunate 260 so as to fuse these three bones together. Teachings of certain embodiments recognize that such fusion may be suitable treating arthritis as well as fractures.

Plate 910 may be dimensioned in any suitable manner. In some embodiments, the dimensions and contour of plate 910 is determined based on measurements from scans of a bone. As one example, plate 910 may be dimensioned based on measurements determined from a particular fractured bone. As another example, bones may be categorized according to size and/or contour, and different variations of plate 910 may be configured to conform to one or more of the different categories. Plate 910 may still be considered to conform to a bone even if such conformance is only approximate or imperfect. For example, plate 910 may be manufactured such that it generally conforms to a large number of bones in the population.

Plate 910 may be comprised of any suitable material. For example, embodiments of plate 910 may be comprised of a bioabsorbable material, a non-bioabsorbable material, or a combination of both. Examples of materials for plate 910 may include, but are not limited to, metals such as titanium alloy, polymers, and laminates. In some embodiments, plate 910 may also include radio-opaque materials to allow visualization on radiographs.

Plate 910 may include any number of openings, such as openings 920, 930, 940, and 950. An opening may include any threaded or unthreaded, fixed or variable angle, locking or non-locking, partially or fully enclosed void in plate 910. In some embodiments, openings may be recessed such that they may receive a fixation device without the head of the fixation device extending above the surface of the plate.

In some embodiments, plate 910 may be configured to conform to radius 200, scaphoid 250, and/or lunate 260. For example, plate 910 may be configured to conform to radius 200 between extensor compartment 202 and extensor compartment 204. Teachings of certain embodiments recognize that plate 910 may be installed between extensor compartment 202 and extensor compartment 204 by moving some or all of the contents of extensor compartment 203, as will be explained in greater detail below. As another example, plate 910 may be configured to conform to radius 200 after the styloid and/or the distal lip of the distal radius has been removed. As another example, plate 910 may be configured to conform to scaphoid 250 and/or lunate 260. For example, FIG. 18B shows plate 910 having a curved fusion portion 912 that approximately matches the contour of scaphoid 250.

In the example of FIGS. 18A and 18B, plate 910 includes a fusion portion 912 and a shaft portion 914. In this example, fusion portion 912 is configured to conform to scaphoid 250 and lunate 260, and shaft portion 914 is configured to conform to radius 200 between extensor compartment 202 and extensor compartment 204. In some embodiments, fusion portion 912 and shaft portion 914 reside on different planes. For example, in the illustrated embodiment, fusion portion 912 is more volar than shaft portion 914 to allow fusion portion 912 to more closely conform to scaphoid 250 and lunate 260.

In some embodiments, fusion portion 912 includes openings 920 and 930. Openings 920 and 930 may be configured to receive fixation devices 922 and 932 respectively. In this example, openings 920 are oriented such that when plate 910 is installed and fixation devices 922 are received through openings 920, fixation devices 922 may provide fixation into lunate 260. Also in this example, openings 930 are oriented such that when plate 910 is installed and fixation devices 932 are received through openings 930, fixation devices 932 may provide fixation into scaphoid 250.

In some embodiments, shaft portion 914 includes openings 940 and 950. Openings 940 and 950 may be configured to receive fixation devices 942 and 952 respectively.

Fixation devices 922, 932, 942, and 952 may include any device for engaging radius 200, scaphoid 250, and/or lunate 260. Examples of fixation devices 922, 932, 942, and 952 may include fixation devices 122 and 422. In some embodiments, at least some of fixation devices 922, 932, 942, and 952 are screws or pegs operable to secure plate 910 to radius 200, scaphoid 250, and/or lunate 260. Additional examples of fixation devices 922, 932, 942, and 952 may include locking and non-locking smooth pegs, locking and non-locking cortical screws, and locking and non-locking cannulated compression screws. In some embodiments, fixation devices 922, 932, 942, and 952 may be similar or the same, such as having similar diameters, threads, and lengths.

Fixation devices 922, 932, 942, and 952 may be comprised of any suitable material. For example, embodiments may be comprised of a bioabsorbable material, a non-bioabsorbable material, or a combination of both. Examples of materials may include, but are not limited to, metals such as titanium alloy. Some embodiments may also include radio-opaque materials to allow visualization on radiographs.

In some embodiments, openings 920, 930, and/or 940 may be defined by a threaded hole in plate 910. In these embodiments, fixation devices may have a threaded head portion configured to engage the threaded hole. In some embodiments, fixation devices also include a threaded shaft portion for engaging radius 200, scaphoid 250, and/or lunate 260.

In some embodiments, opening 950 may be an oblong opening. Teachings of certain embodiments recognize that an oblong opening may aid in positioning a plate on a bone and may be used to provide compression. For example, plate 910 may be attached to radius 200 by inserting fixation devices 952 through oblong openings 950 to engage bone. Plate 910 may then be repositioned relative to radius 200, allowing fixation device 952 to move relative to oblong opening 950. Once plate 910 is in a suitable position, fixation device 952 may be tightened to radius 200.

Figure 19A:
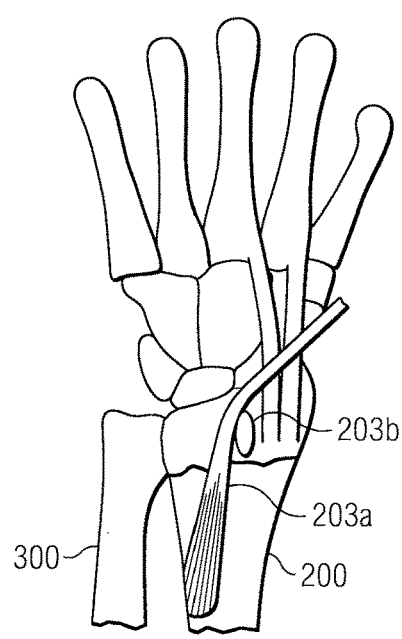
FIGS. 19A-19D show progressive views of the bone fusion system of FIGS. 18A and 18B being installed on the radius, scaphoid, and lunate of FIG. 10A according to one embodiment.
Figure 19B:
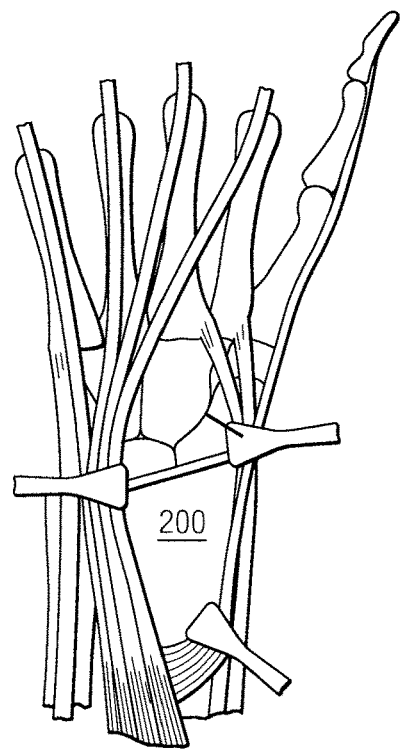

FIGS. 19A-19D show progressive views of bone fusion system 900 being installed on radius 200, scaphoid 250, and lunate 260 according to one embodiment. In FIG. 19A, radius 200 is shown EPL tendon 203a and Lister's Tubercle 203b. In FIG. 19B, Lister's Tubercle 203b is removed, and EPL tendon 203a is transposed out of compartment 203.

Figure 19C:
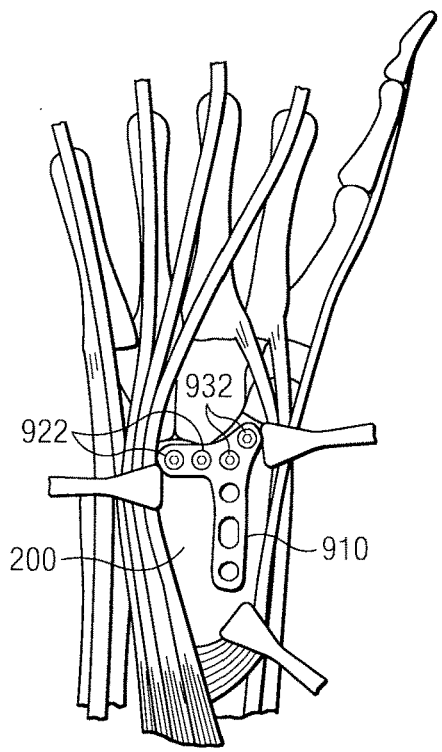
Figure 19D:
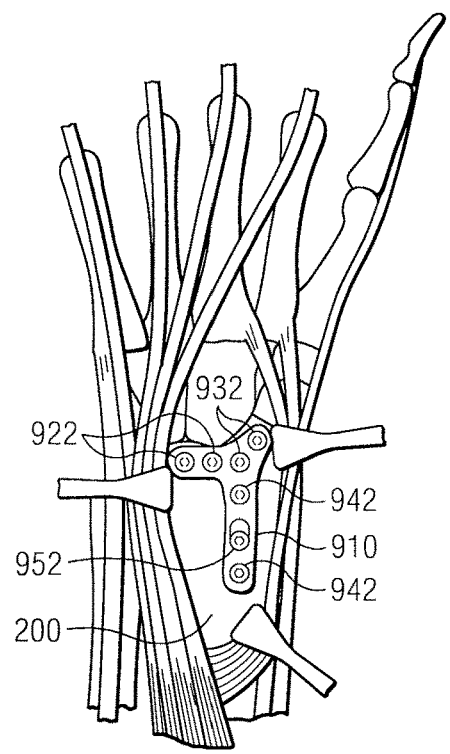

In FIG. 19C, plate 910 is placed on radius 200, scaphoid 250, and lunate 260. In this example, plate 910 is placed in compartment 203 over the former location of Lister's Tubercle 203b. Fixation devices 922 and 932 are then inserted through openings 920 and 930 to engage scaphoid 250 and lunate 260. In FIG. 19D, fixation devices 942 and 952 are inserted through openings 940 and 950 to engage radius 200.

As explained above, bone fixation system 900 may be installed on the dorsal side of radius 200. In some circumstances, however, fixation may also be provided to the volar side of radius 200. For example, in some circumstances, a dissection may be performed on the volar side for other reasons only to discover that the original reasons for the volar dissection are no longer applicable. For example, the radiograph may not fully show the type or extent of fractures of radius 200. In such circumstances, fixation and/or fusion may be provided to the volar side of radius 200 rather than starting a new procedure on the dorsal side of radius 200.

FIGS. 20A and 20B show a bone fusion system 900' according to one embodiment. FIG. 20A shows plate 910' of bone fusion system 900', and FIG. 20B shows bone fusion system 900' installed against scaphoid 250 and lunate 260. In operation, plate 910' may be secured to radius 200, scaphoid 250, and lunate 260 so as to fuse these three bones together from the volar side. In some embodiments, plate 910 may resemble plate 910' and may be configured to provide fusion from either the volar or dorsal sides. For example, in some embodiments, a right-handed volar plate 910' may have a similar shape and dimensions to a left-handed dorsal plate 910.

Plate 910' may be dimensioned in any suitable manner. In some embodiments, the dimensions and contour of plate 910' is determined based on measurements from scans of a bone. As one example, plate 910' may be dimensioned based on measurements determined from a particular fractured bone. As another example, bones may be categorized according to size and/or contour, and different variations of plate 910' may be configured to conform to one or more of the different categories. Plate 910' may still be considered to conform to a bone even if such conformance is only approximate or imperfect. For example, plate 910' may be manufactured such that it generally conforms to a large number of bones in the population.

Plate 910' may be comprised of any suitable material. For example, embodiments of plate 910' may be comprised of a bioabsorbable material, a non-bioabsorbable material, or a combination of both. Examples of materials for plate 910' may include, but are not limited to, metals such as titanium alloy, polymers, and laminates. In some embodiments, plate 910' may also include radio-opaque materials to allow visualization on radiographs.

Plate 910' may include any number of openings, such as openings 920', 930', 940', and 950'. An opening may include any threaded or unthreaded, fixed or variable angle, locking or non-locking, partially or fully enclosed void in plate 910'. In some embodiments, openings may be recessed such that they may receive a fixation device without the head of the fixation device extending above the surface of the plate.

In the example of FIGS. 20A and 20B, plate 910' includes a fusion portion 912' and a shaft portion 914'. In this example, fusion portion 912' is configured to conform to scaphoid 250 and lunate 260, and shaft portion 914' is configured to conform to radius 200 between extensor compartment 202 and extensor compartment 204.

In some embodiments, fusion portion 912' includes openings 920' and 930'. Openings 920' and 930' may be configured to receive fixation devices 922' and 932' respectively. In this example, openings 920' are oriented such that when plate 910' is installed and fixation devices 922' are received through openings 920', fixation devices 922' may provide fixation into lunate 260. Also in this example, openings 930' are oriented such that when plate 910' is installed and fixation devices 932' are received through openings 930', fixation devices 932' may provide fixation into scaphoid 250.

In some embodiments, shaft portion 914' includes openings 940' and 950'. Openings 940' and 950' may be configured to receive fixation devices 942' and 952' respectively.

Fixation devices 922', 932', 942', and 952' may include any device for engaging radius 200, scaphoid 250, and/or lunate 260. Examples of fixation devices 922', 932', 942', and 952' may include fixation devices 122 and 422. In some embodiments, at least some of fixation devices 922', 932', 942', and 952' are screws or pegs operable to secure plate 910' to radius 200, scaphoid 250, and/or lunate 260. Additional examples of fixation devices 922', 932', 942', and 952' may include locking and non-locking smooth pegs, locking and non-locking cortical screws, and locking and non-locking cannulated compression screws. In some embodiments, fixation devices 922', 932', 942', and 952' may be similar or the same, such as having similar diameters, threads, and lengths.

Fixation devices 922', 932', 942', and 952' may be comprised of any suitable material. For example, embodiments may be comprised of a bioabsorbable material, a non-bioabsorbable material, or a combination of both. Examples of materials may include, but are not limited to, metals such as titanium alloy. Some embodiments may also include radio-opaque materials to allow visualization on radiographs.

In some embodiments, openings 920', 930', and/or 940' may be defined by a threaded hole in plate 910'. In these embodiments, fixation devices may have a threaded head portion configured to engage the threaded hole. In some embodiments, fixation devices also include a threaded shaft portion for engaging radius 200, scaphoid 250, and/or lunate 260.

In some embodiments, opening 950' may be an oblong opening. Teachings of certain embodiments recognize that an oblong opening may aid in positioning a plate on a bone and may be used to provide compression. For example, plate 910' may be attached to radius 200 by inserting fixation devices 952' through oblong openings 950' to engage bone. Plate 910' may then be repositioned relative to radius 200, allowing fixation device 952' to move relative to oblong opening 950'. Once plate 910' is in a suitable position, fixation device 952' may be tightened to radius 200.

Figure 21A:
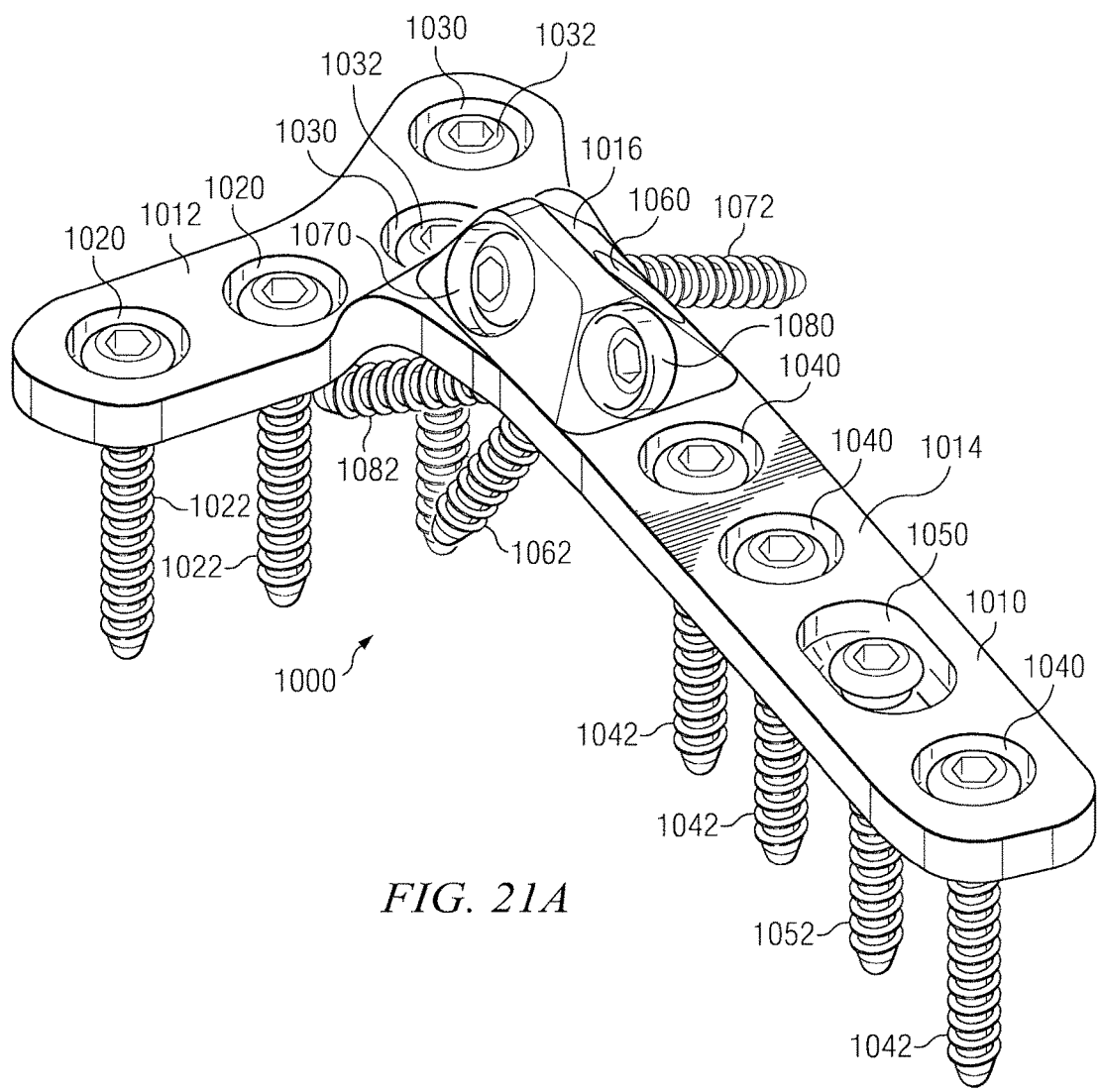
FIG. 21A shows a bone fixation/fusion system according to one embodiment.
Figure 21B:
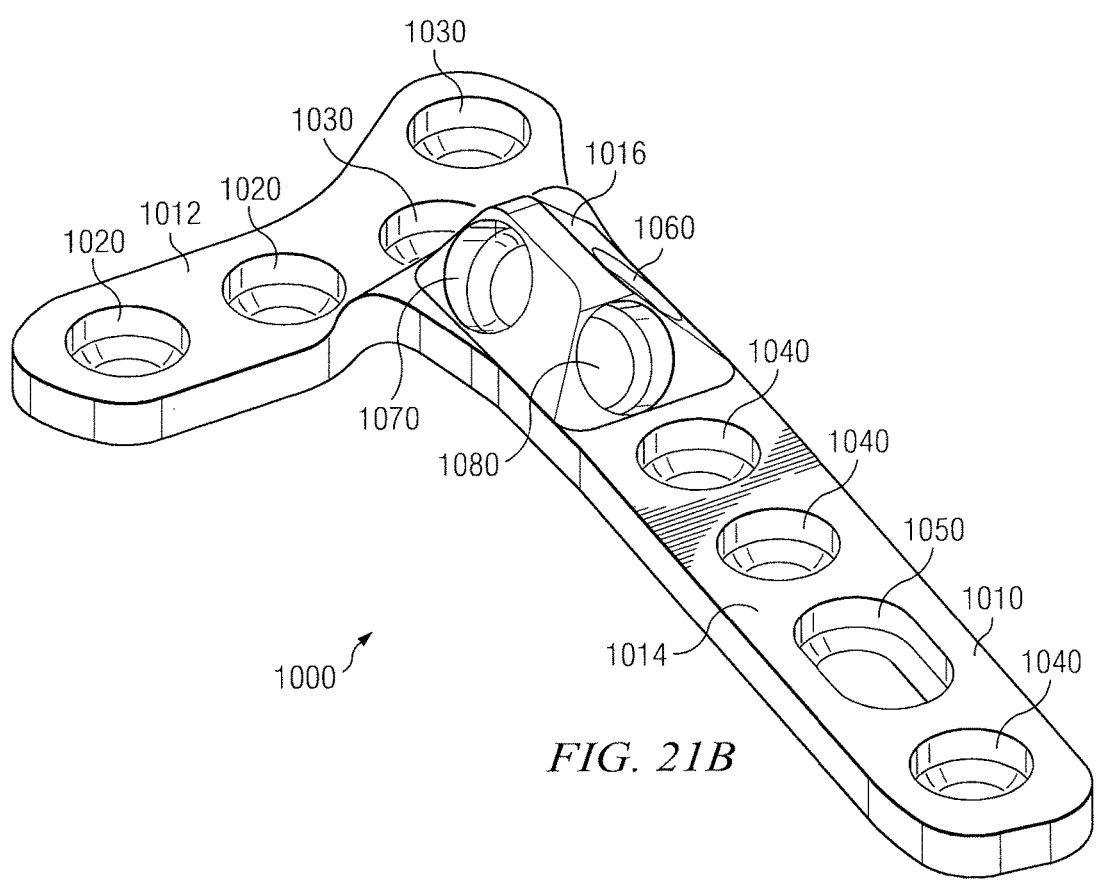
FIG. 21B shows the plate of the bone fixation/fusion system of FIG. 21A.

FIG. 21A shows a bone fixation/fusion system 1000 according to one embodiment. FIG. 21B shows plate 1010 of bone fixation/fusion system 1000. In operation, plate 1010 may be secured to radius 200, scaphoid 250, and lunate 260 so as to fuse these three bones together. In some embodiments, bone fixation/fusion system 1000 may resemble a combination of bone fixation system 800 and bone fusion system 900.

Plate 1010 may be dimensioned in any suitable manner. In some embodiments, the dimensions and contour of plate 1010 is determined based on measurements from scans of a bone. As one example, plate 1010 may be dimensioned based on measurements determined from a particular fractured bone. As another example, bones may be categorized according to size and/or contour, and different variations of plate 1010 may be configured to conform to one or more of the different categories. Plate 1010 may still be considered to conform to a bone even if such conformance is only approximate or imperfect. For example, plate 1010 may be manufactured such that it generally conforms to a large number of bones in the population.

Plate 1010 may be comprised of any suitable material. For example, embodiments of plate 1010 may be comprised of a bioabsorbable material, a non-bioabsorbable material, or a combination of both. Examples of materials for plate 1010 may include, but are not limited to, metals such as titanium alloy, polymers, and laminates. In some embodiments, plate 1010 may also include radio-opaque materials to allow visualization on radiographs.

Plate 1010 may include any number of openings, such as openings 1020, 1030, 1040, 1050, 1060, 1070, and 1080. An opening may include any threaded or unthreaded, fixed or variable angle, locking or non-locking, partially or fully enclosed void in plate 1010. In some embodiments, openings may be recessed such that they may receive a fixation device without the head of the fixation device extending above the surface of the plate.

In some embodiments, plate 1010 may be configured to conform to radius 200, scaphoid 250, and/or lunate 260. For example, plate 1010 may be configured to conform to radius 200 between extensor compartment 202 and extensor compartment 204. Teachings of certain embodiments recognize that plate 1010 may be installed between extensor compartment 202 and extensor compartment 204 by moving some or all of the contents of extensor compartment 203, as will be explained in greater detail below. As another example, plate 1010 may be configured to conform to radius 200 after the styloid and/or the distal lip of the distal radius has been removed. As another example, plate 1010 may be configured to conform to scaphoid 250 and/or lunate 260. For example, plate 1010 may have a curved fusion portion 1012 that approximately matches the contour of scaphoid 250.

In the example of FIGS. 21A and 21B, plate 910 includes a fusion portion 1012, a shaft portion 1014, and a fixation portion 1016. In this example, fusion portion 1012 is configured to conform to scaphoid 250 and lunate 260, and shaft portion 1014 and fixation portion 1016 are configured to conform to radius 200 between extensor compartment 202 and extensor compartment 204. In some embodiments, fusion portion 1012 and fixation portion 1016 reside on different planes. For example, in the illustrated embodiment, fusion portion 1012 is more volar than fixation portion 1016 to allow fusion portion 1012 to more closely conform to scaphoid 250 and lunate 260.

In some embodiments, fusion portion 1012 includes openings 1020 and 1030. Openings 1020 and 1030 may be configured to receive fixation devices 1022 and 1032 respectively. In this example, openings 1020 are oriented such that when plate 1010 is installed and fixation devices 1022 are received through openings 1020, fixation devices 1022 may provide fixation into lunate 260. Also in this example, openings 1030 are oriented such that when plate 1010 is installed and fixation devices 1032 are received through openings 1030, fixation devices 1032 may provide fixation into scaphoid 250.

In some embodiments, shaft portion 1014 includes openings 1040 and 1050. Openings 1040 and 1050 may be configured to receive fixation devices 1042 and 1052 respectively.

As shown in FIGS. 21A and 21B, fixation portion 1016 may include openings 1060, 1070, and 1080. Openings 1060, 1070, and 1080 may be configured to receive fixation devices 1062, 1072, and 1082. In some embodiments, openings 1060, 1070, and 1080 are oriented similarly to openings 820, 830, and 840 of plate 810. For example, in some embodiments, openings 1060, 1070, and 1080 may be generally collinear and/or coplanar with openings 1040 and 1050. For example, in FIGS. 21A and 21B, openings 1040, 1050, 1060, 1070, and 1080 are drawn to be collinear as a reference line may be drawn intersecting openings 1040, 1050, 1060, 1070, and 1080. In this example, openings 1040, 1050, 1060, 1070, and 1080 are also generally coplanar as a reference plane may be drawn through a central axis of opening 1080 and openings 1040, 1050, 1060, 1070, and 1080.

In this example, opening 1060 is oriented such that when plate 1010 is installed against radius 200 and fixation device 1062 is received, fixation device 1062 may provide subchondral support to the scaphoid facet 255. Also in this example, opening 1070 is oriented such that when plate 1010 is installed against radius 200 and fixation device 1072 is received, fixation device 1072 may provide subchondral support to the lunate facet 265. Also in this example, opening 1080 is oriented such that when plate 1010 is installed against radius 200 and fixation device 1082 is received, fixation device 1082 may provide fixation into a distal fragment of radius 200.

Fixation devices 1022, 1032, 1042, 1052, 1062, 1072, and 1082 may include any device for engaging radius 200, scaphoid 250, and/or lunate 260. Examples of fixation devices 1022, 1032, 1042, 1052, 1062, 1072, and 1082 may include fixation devices 122 and 422. In some embodiments, at least some of fixation devices 1022, 1032, 1042, 1052, 1062, 1072, and 1082 are screws or pegs operable to secure plate 910 to radius 200, scaphoid 250, and/or lunate 260. Additional examples of fixation devices 1022, 1032, 1042, 1052, 1062, 1072, and 1082 may include locking and non-locking smooth pegs, locking and non-locking cortical screws, and locking and non-locking cannulated compression screws. In some embodiments, fixation devices 1022, 1032, 1042, 1052, 1062, 1072, and 1082 may be similar or the same, such as having similar diameters, threads, and lengths.

Fixation devices 1022, 1032, 1042, 1052, 1062, 1072, and 1082 may be comprised of any suitable material. For example, embodiments may be comprised of a bioabsorbable material, a non-bioabsorbable material, or a combination of both. Examples of materials may include, but are not limited to, metals such as titanium alloy. Some embodiments may also include radio-opaque materials to allow visualization on radiographs.

In some embodiments, openings 1020, 1030, 1040, 1060, 1070, and/or 1080 may be defined by a threaded hole in plate 1010. In these embodiments, fixation devices may have a threaded head portion configured to engage the threaded hole. In some embodiments, fixation devices also include a threaded shaft portion for engaging radius 200, scaphoid 250, and/or lunate 260.

In some embodiments, opening 1050 may be an oblong opening. Teachings of certain embodiments recognize that an oblong opening may aid in positioning a plate on a bone and may be used to provide compression. For example, plate 1010 may be attached to radius 200 by inserting fixation devices 1052 through oblong openings 950 to engage bone. Plate 1010 may then be repositioned relative to radius 200, allowing fixation device 1052 to move relative to oblong opening 1050. Once plate 1010 is in a suitable position, fixation device 1052 may be tightened to radius 200.

Figure 22A:
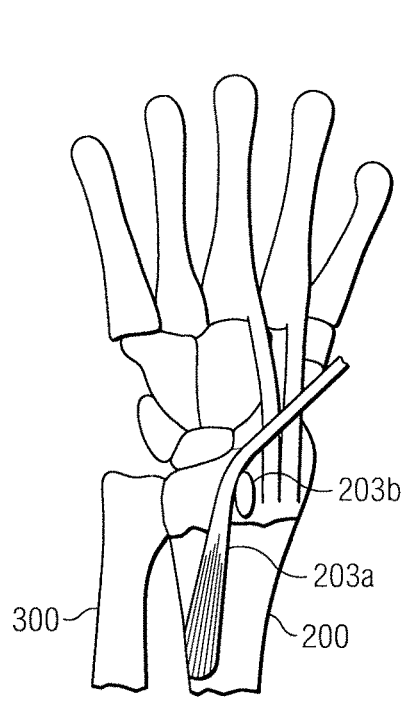
FIGS. 22A-22D show progressive views of the bone fusion system of FIG. 21A being installed on the radius, scaphoid, and lunate of FIG. 10A according to one embodiment.
Figure 22B:
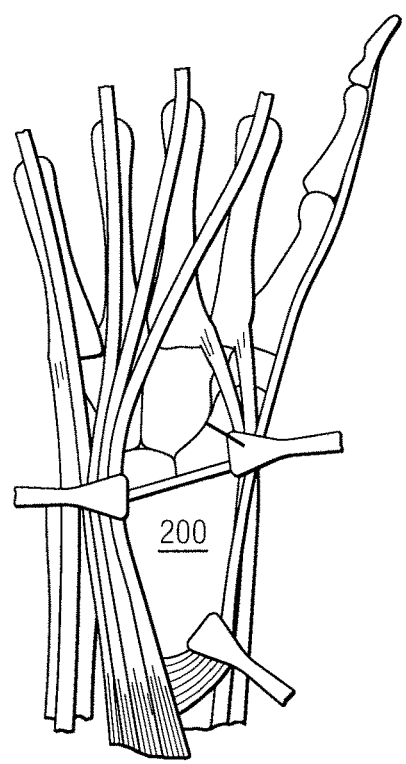

FIGS. 22A-22D show progressive views of bone fusion system 1000 being installed on radius 200, scaphoid 250, and lunate 260 according to one embodiment. In FIG. 22A, radius 200 is shown EPL tendon 203a and Lister's Tubercle 203b. In FIG. 22B, Lister's Tubercle 203b is removed, and EPL tendon 203a is transposed out of compartment 203.

Figure 22C:
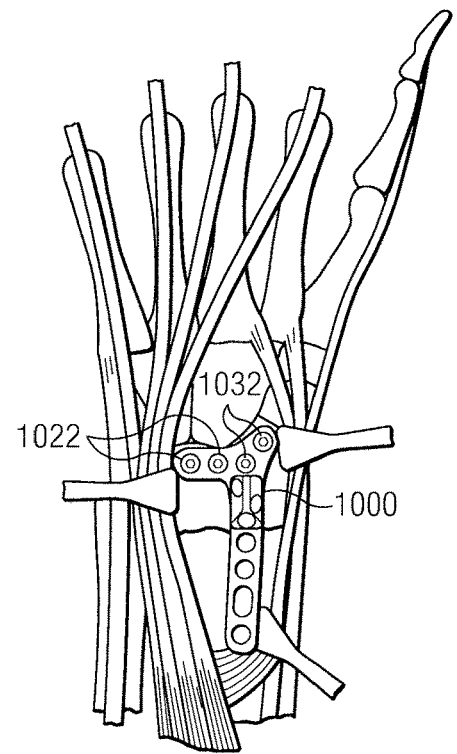
Figure 22D:
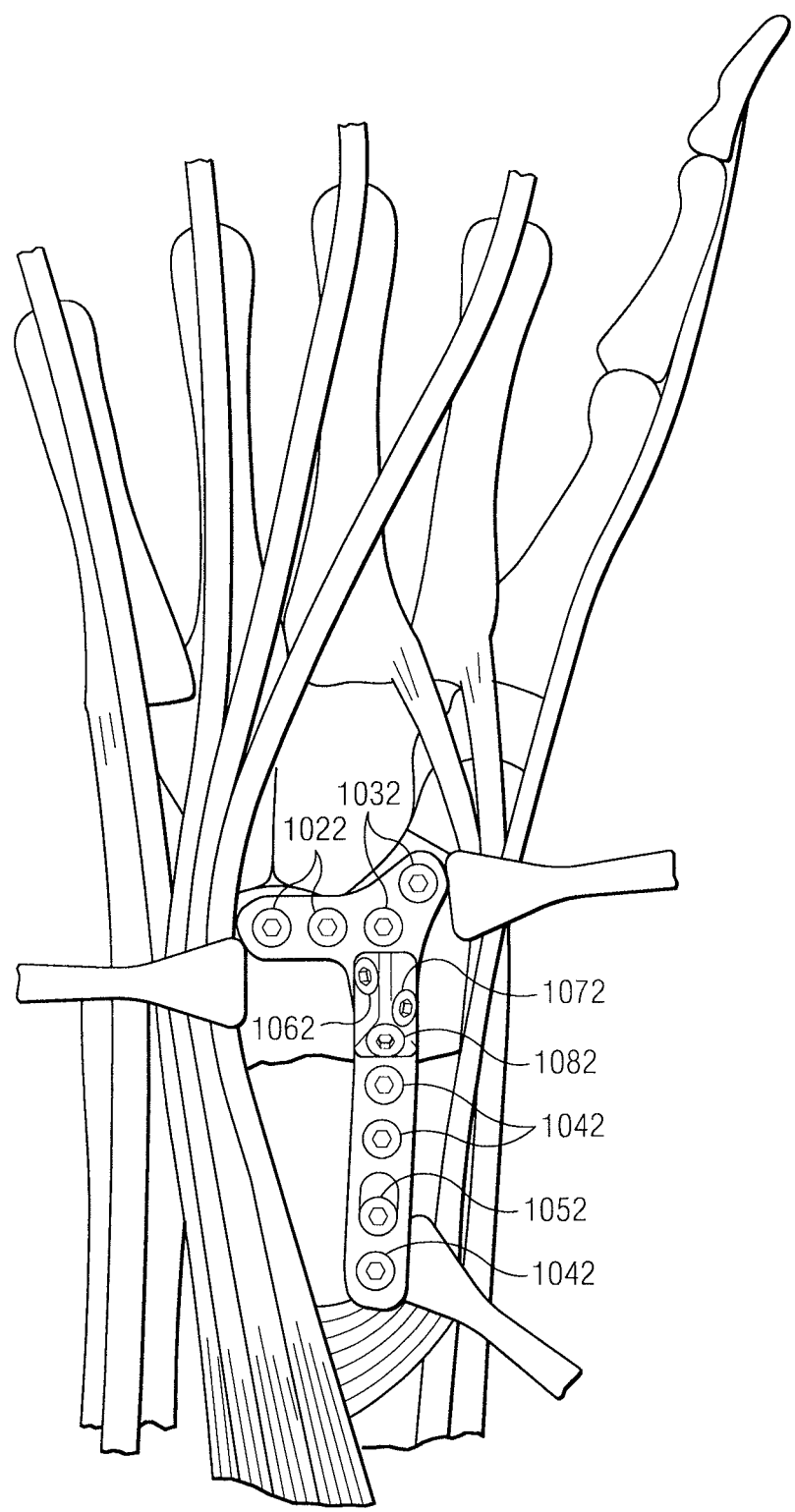

In FIG. 22C, plate 1010 is placed on radius 200, scaphoid 250, and lunate 260. In this example, plate 1010 is placed in compartment 203 over the former location of Lister's Tubercle 203b. Fixation devices 1022 and 1032 are then inserted through openings 1020 and 1030 to engage scaphoid 250 and lunate 260. In FIG. 22D, fixation devices 1042, 1052, 1062, 1072, and 1082 are inserted through openings 940 and 950 to engage radius 200.

Figure 23A:
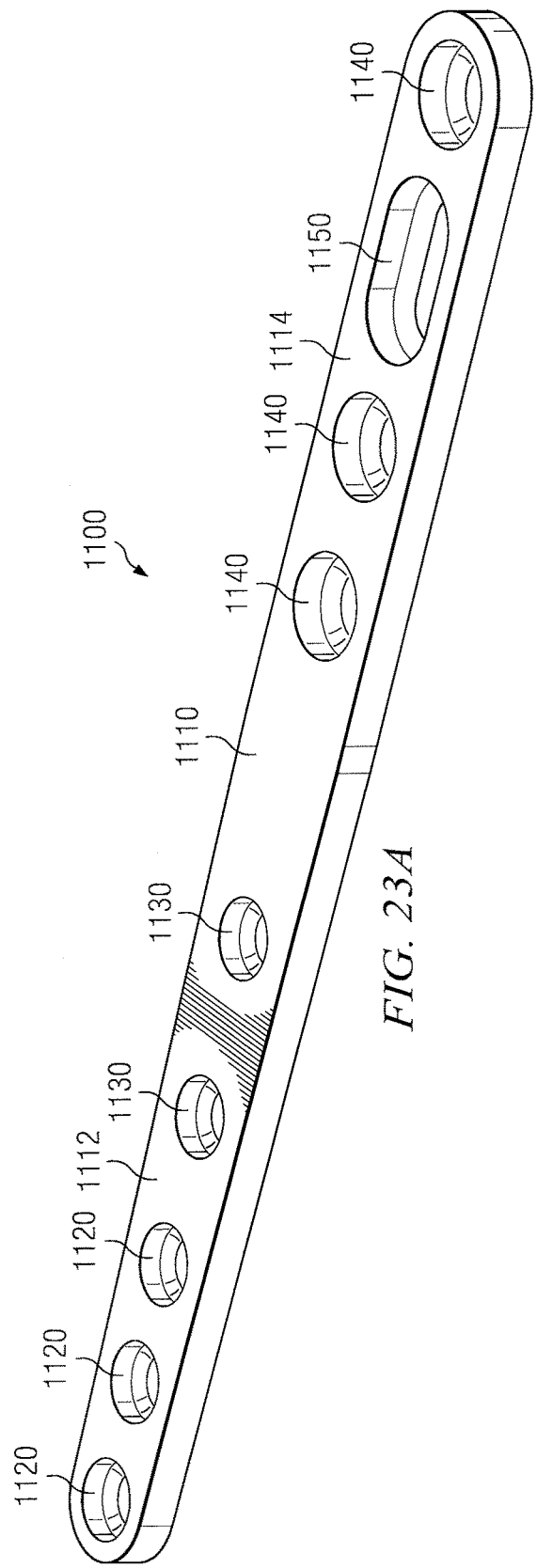
FIGS. 23A-23D show a bone fusion/spanning system according to one embodiment.
Figure 23C:
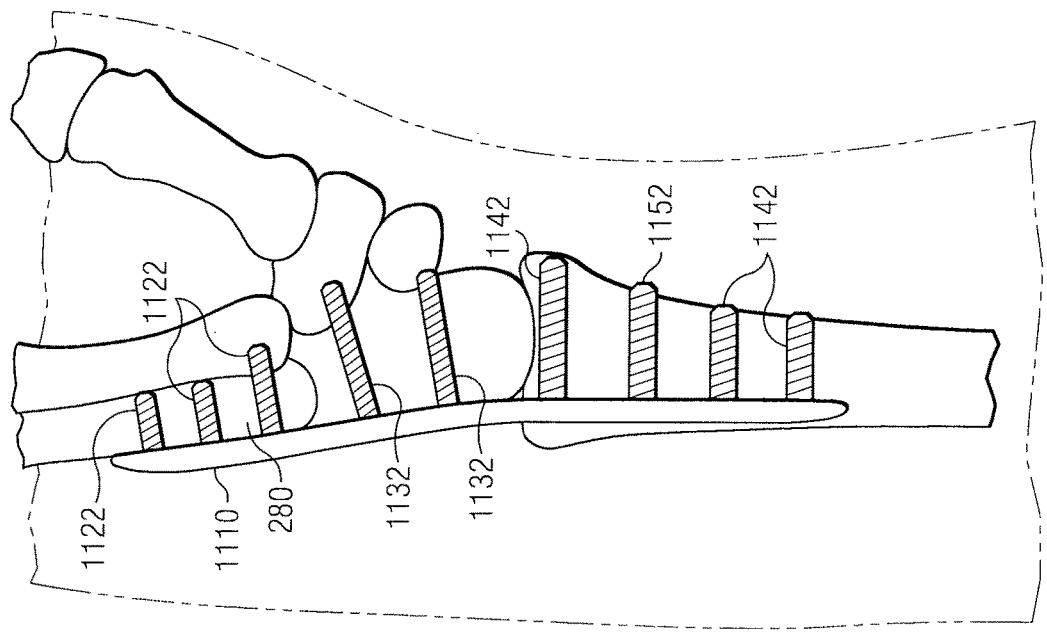
Figure 23B:
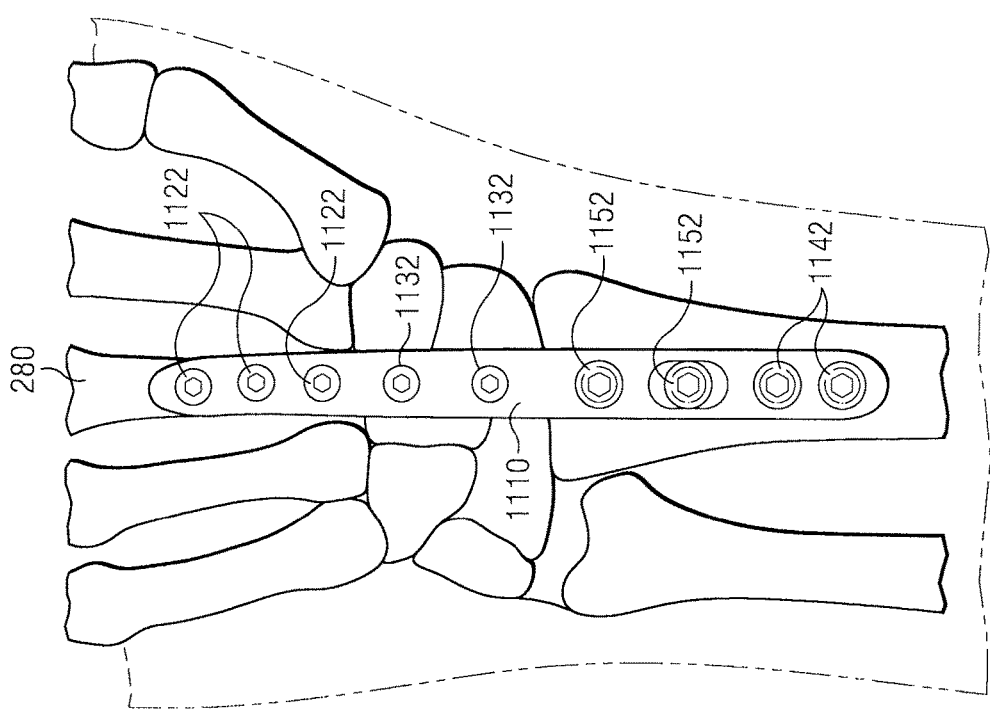
Figure 23D:
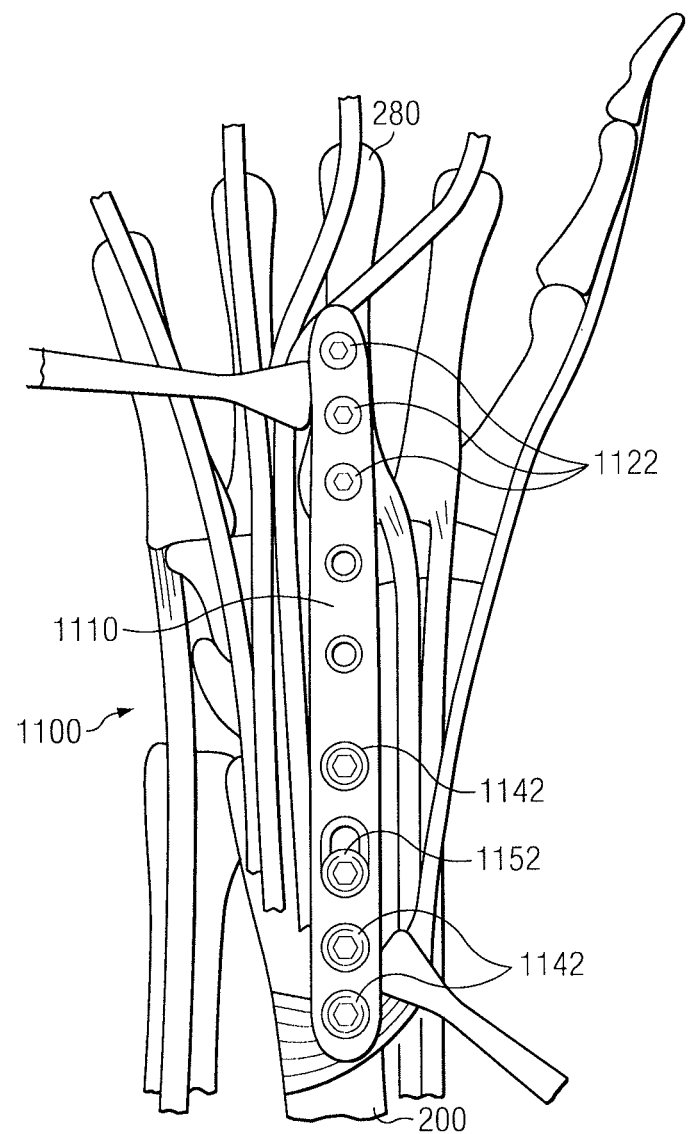

FIGS. 23A, 23B, 23C, and 23D show a bone fusion/spanning system 1100 according to one embodiment. FIG. 23A shows plate 1110 of bone fusion/spanning system 1100, and FIGS. 23B, 23C, and 23D show bone fusion/spanning system 1100 installed against radius 200. In operation, plate 1110 may be secured to radius 200 and a metacarpal 280.

Plate 1110 may be dimensioned in any suitable manner. In some embodiments, the dimensions and contour of plate 1110 is determined based on measurements from scans of a bone. As one example, plate 1110 may be dimensioned based on measurements determined from a particular fractured bone. As another example, bones may be categorized according to size and/or contour, and different variations of plate 1110 may be configured to conform to one or more of the different categories. Plate 1110 may still be considered to conform to a bone even if such conformance is only approximate or imperfect. For example, plate 1110 may be manufactured such that it generally conforms to a large number of bones in the population.

Plate 1110 may be comprised of any suitable material. For example, embodiments of plate 1110 may be comprised of a bioabsorbable material, a non-bioabsorbable material, or a combination of both. Examples of materials for plate 1110 may include, but are not limited to, metals such as titanium alloy, polymers, and laminates. In some embodiments, plate 1110 may also include radio-opaque materials to allow visualization on radiographs.

Plate 1110 may include any number of openings, such as openings 1120, 1130, 1140, and 1150. An opening may include any threaded or unthreaded, fixed or variable angle, locking or non-locking, partially or fully enclosed void in plate 1110. In some embodiments, openings may be recessed such that they may receive a fixation device without the head of the fixation device extending above the surface of the plate.

In some embodiments, plate 1110 may be configured to conform to radius 1100 and metacarpal 280. For example, plate 1110 may be configured to conform to radius 1100 between extensor compartment 202 and extensor compartment 204. Teachings of certain embodiments recognize that plate 1110 may be installed between extensor compartment 202 and extensor compartment 204 by moving some or all of the contents of extensor compartment 203. As another example, plate 1110 may be configured to conform to metacarpal 280.

In the illustrated examples, plate 1110 includes a spanning portion 1112 and a shaft portion 1114. In this example, spanning portion 1112 is configured to conform to metacarpal 280, and shaft portion 1114 is configured to conform to radius 200 between extensor compartment 202 and extensor compartment 204.

In some embodiments, spanning portion 1112 includes openings 1120 and 1130. Openings 1120 and 1130 may be configured to receive fixation devices 1122 and 1132 respectively. In this example, openings 1120 are oriented such that when plate 1110 is installed and fixation devices 1122 are received through openings 1120, fixation devices 1122 may engage metacarpal 280. Also in this example, openings 1130 are oriented such that when plate 1110 is installed and fixation devices 1132 are received through openings 1130, fixation devices 1132 may engage carpal bones such as scaphoid 250, lunate 260, the trapezoid, or the capitate.

Teachings of certain embodiments recognize that fixation devices 1132 may be inserted through openings 1130 to provide optional fusion as well as spanning. For example, in FIGS. 23E and 23C, fixation devices 1132 are installed to provide optional fusion. In FIG. 23D, on the other hand, fixation devices 1132 are omitted.

In some embodiments, shaft portion 1114 includes openings 1140 and 1150. Openings 1140 and 1150 may be configured to receive fixation devices 1142 and 1152 respectively.

Fixation devices 1122, 1132, 1142, and 1152 may include any device for engaging radius 200, metacarpal 280, and/or carpal bones. Examples of fixation devices 1122, 1132, 1142, and 1152 may include fixation devices 122 and 422. In some embodiments, at least some of fixation devices 1122, 1132, 1142, and 1152 are screws or pegs operable to secure plate 1110 to radius 200, metacarpal 280, and/or carpal bones. Additional examples of fixation devices 1122, 1132, 1142, and 1152 may include locking and non-locking smooth pegs, locking and non-locking cortical screws, and locking and non-locking cannulated compression screws. In some embodiments, fixation devices 1122, 1132, 1142, and 1152 may be similar or the same, such as having similar diameters, threads, and lengths.

Fixation devices 1122, 1132, 1142, and 1152 may be comprised of any suitable material. For example, embodiments may be comprised of a bioabsorbable material, a non-bioabsorbable material, or a combination of both. Examples of materials may include, but are not limited to, metals such as titanium alloy. Some embodiments may also include radio-opaque materials to allow visualization on radiographs.

In some embodiments, openings 1120, 1130, and/or 1140 may be defined by a threaded hole in plate 1110. In these embodiments, fixation devices may have a threaded head portion configured to engage the threaded hole. In some embodiments, fixation devices also include a threaded shaft portion for engaging radius 200, metacarpal 280, and/or carpal bones.

In some embodiments, opening 1150 may be an oblong opening. Teachings of certain embodiments recognize that an oblong opening may aid in positioning a plate on a bone and may be used to provide compression. For example, plate 1110 may be attached to radius 200 by inserting fixation devices 1152 through oblong openings 1150 to engage bone. Plate 1110 may then be repositioned relative to radius 200, allowing fixation device 1152 to move relative to oblong opening 1150. Once plate 1110 is in a suitable position, fixation device 1152 may be tightened to radius 200.

In FIGS. 23A-23D, plate 1110 is relatively straight such that openings 1120, 1130, 1140, and 1150 are generally coplanar but not necessarily collinear. For example, FIG. 23B shows spanning portion 1112 having twenty degrees of dorsal tilt relative to shaft portion 1114. However, teachings of certain embodiments recognize that other angles may be provided, including, but not limited to, ten to thirty degrees.

In some embodiments, however, openings of plate 1110 may not necessarily be generally coplanar. For example, plate 1110 may have an ulnar bend between spanning portion 1112 and shaft portion 1114. Teachings of certain embodiments recognize that providing an angled plate may reposition metacarpal 280 such that the hand is in a more natural position relative to radius 200.

Figure 24:
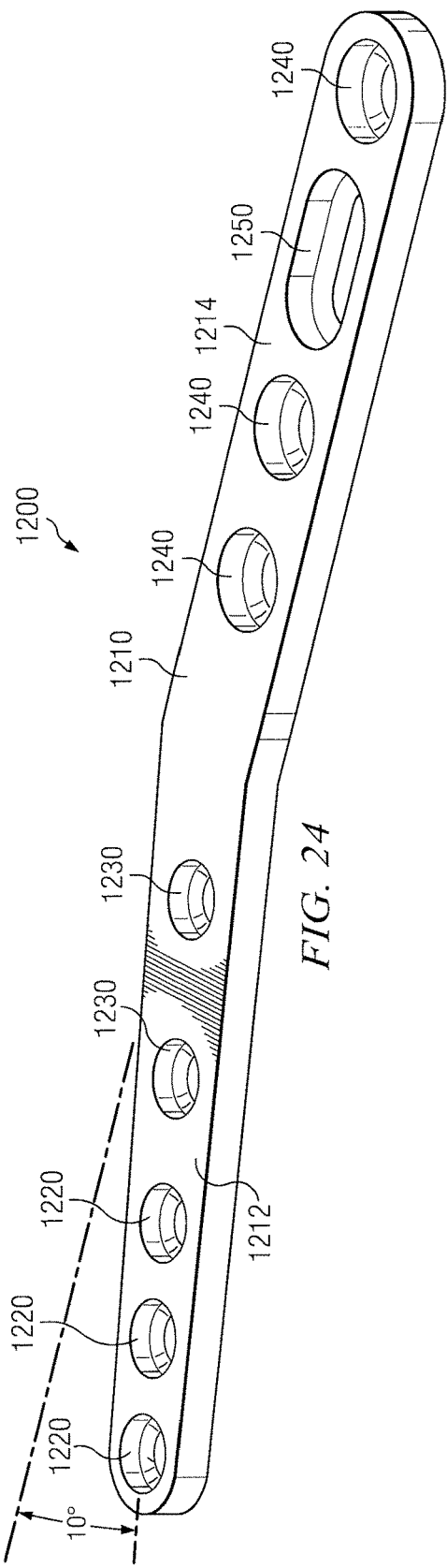
FIG. 24 shows a variation of the bone fusion/spanning system of FIGS. 23A-23D.

FIG. 24 shows a bone spanning/fusion system 1200 according to one embodiment. In this example, plate 1210 includes openings 1220, 1230, 1240, and 1250 similar to openings 1120, 1130, 1140, and 1150 of plate 1110.

Unlike plate 1110, plate 1210 provides an ulnar bend between spanning portion 1212 and shaft portion 1214. Teachings of certain embodiments recognize that an ulnar bend may reposition metacarpal 280 such that the hand is in a more natural position relative to radius 200. Teachings of certain embodiments also recognize that providing an ulnar bend may also improve hand strength.

In the illustrated example, spanning portion 1212 has an ulnar bend of ten degrees towards ulna 300. However, teachings of certain embodiments recognize that other angles may be provided, including, but not limited to, ten to fifteen degrees or even five to twenty degrees.

In the illustrated example, spanning portion 1212 also has a dorsal angle relative to shaft portion 1214. Teachings of certain embodiments recognize that providing a dorsal angle may reposition 280 such that the hand is in a more natural position relative to radius 200.

Figure 25D:
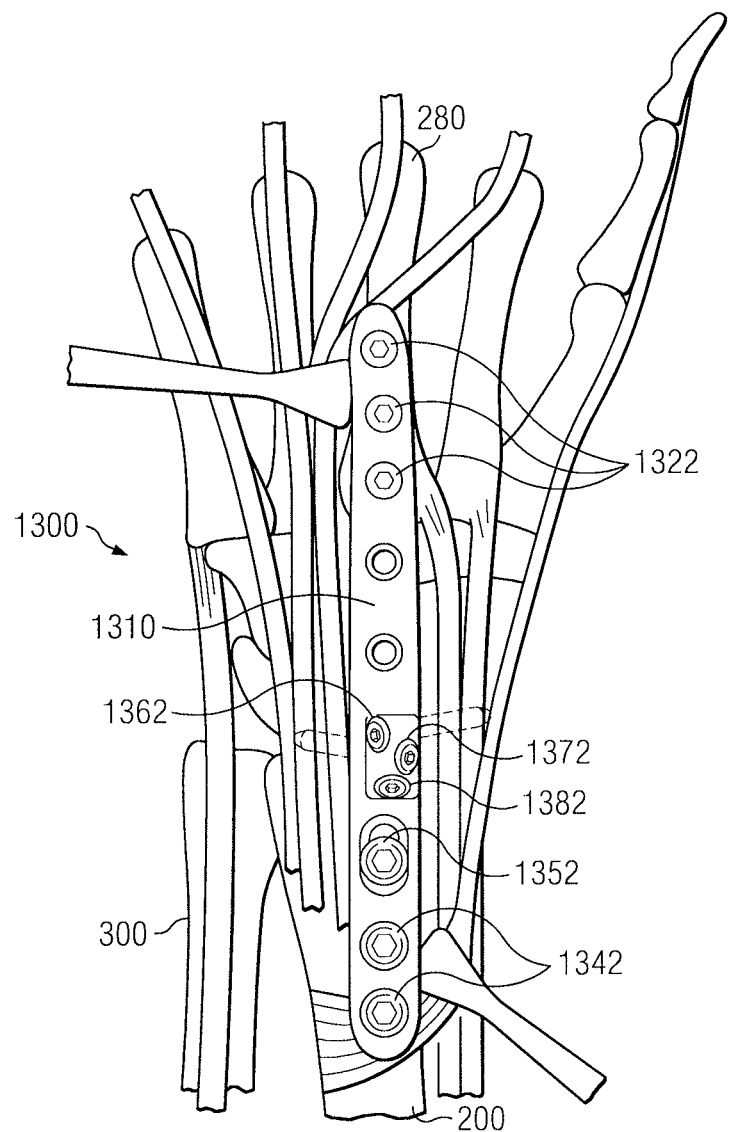

FIGS. 25A, 25B, 25C, and 25D show a bone fusion/ fixation/spanning system 1300 according to one embodiment. FIG. 25A shows plate 1310 of bone fusion/spanning system 1300, and FIGS. 25B, 25C, and 25D show bone fusion/fixation/spanning system 1300 installed against radius 200. In operation, plate 1310 may be secured to radius 200 and a metacarpal 280. In some embodiments, bone fixation/fusion system 1300 may resemble a combination of bone fixation system 800 and bone fusion/spanning system 1100.

Plate 1310 may be dimensioned in any suitable manner. In some embodiments, the dimensions and contour of plate 1310 is determined based on measurements from scans of a bone. As one example, plate 1310 may be dimensioned based on measurements determined from a particular fractured bone. As another example, bones may be categorized according to size and/or contour, and different variations of plate 1310 may be configured to conform to one or more of the different categories. Plate 1310 may still be considered to conform to a bone even if such conformance is only approximate or imperfect. For example, plate 1310 may be manufactured such that it generally conforms to a large number of bones in the population.

Plate 1310 may be comprised of any suitable material. For example, embodiments of plate 1310 may be comprised of a bioabsorbable material, a non-bioabsorbable material, or a combination of both. Examples of materials for plate 1310 may include, but are not limited to, metals such as titanium alloy, polymers, and laminates. In some embodiments, plate 1310 may also include radio-opaque materials to allow visualization on radiographs.

Plate 1310 may include any number of openings, such as openings 1320, 1330, 1340, 1350, 1360, 1370, and 1380. An opening may include any threaded or unthreaded, fixed or variable angle, locking or non-locking, partially or fully enclosed void in plate 1310. In some embodiments, openings may be recessed such that they may receive a fixation device without the head of the fixation device extending above the surface of the plate.

In some embodiments, plate 1310 may be configured to conform to radius 1300 and metacarpal 280. For example, plate 1310 may be configured to conform to radius 1300 between extensor compartment 202 and extensor compartment 204. Teachings of certain embodiments recognize that plate 1310 may be installed between extensor compartment 202 and extensor compartment 204 by moving some or all of the contents of extensor compartment 203. As another example, plate 1310 may be configured to conform to metacarpal 280.

In the illustrated examples, plate 1310 includes a spanning portion 1312, a shaft portion 1314, and a fixation portion 1316. In this example, spanning portion 1312 is configured to conform to metacarpal 280, and shaft portion 1314 and fixation portion 1316 are configured to conform to radius 200 between extensor compartment 202 and extensor compartment 204.

In some embodiments, spanning portion 1312 includes openings 1320 and 1330. Openings 1320 and 1330 may be configured to receive fixation devices 1322 and 1332 respectively. In this example, openings 1320 are oriented such that when plate 1310 is installed and fixation devices 1322 are received through openings 1320, fixation devices 1322 may engage metacarpal 280. Also in this example, openings 1330 are oriented such that when plate 1310 is installed and fixation devices 1332 are received through openings 1330, fixation devices 1332 may engage carpal bones such as scaphoid 250, lunate 260, the trapezoid, or the capitate.

Teachings of certain embodiments recognize that fixation devices 1332 may be inserted through openings 1330 to provide optional fusion as well as spanning. For example, in FIGS. 25B and 25C, fixation devices 1332 are installed to provide optional fusion. In FIG. 25D, on the other hand, fixation devices 1332 are omitted.

In some embodiments, shaft portion 1314 includes openings 1340 and 1350. Openings 1340 and 1350 may be configured to receive fixation devices 1342 and 1352 respectively.

In some embodiments, fixation portion 1316 may include openings 1360, 1370, and 1380. Openings 1360, 1370, and 1380 may be configured to receive fixation devices 1362, 1372, and 1382. In some embodiments, openings 1360, 1370, and 1380 are oriented similarly to openings 820, 830, and 840 of plate 810. For example, in some embodiments, openings 1360, 1370, and 1380 may be generally collinear and/or coplanar with openings 1340 and 1350. In FIG. 25B, openings 1340, 1350, 1360, 1370, and 1380 are drawn to be collinear as a reference line may be drawn intersecting openings 1340, 1350, 1360, 1370, and 1380. In this example, openings 1340, 1350, 1360, 1370, and 1380 are also generally coplanar as a reference plane may be drawn through a central axis of opening 1380 and openings 1340, 1350, 1360, 1370, and 1380.

In this example, opening 1360 is oriented such that when plate 1310 is installed against radius 200 and fixation device 1362 is received, fixation device 1362 may provide subchondral support to the scaphoid facet 255. Also in this example, opening 1370 is oriented such that when plate 1310 is installed against radius 200 and fixation device 1372 is received, fixation device 1372 may provide subchondral support to the lunate facet 265. Also in this example, opening 1380 is oriented such that when plate 1310 is installed against radius 200 and fixation device 1382 is received, fixation device 1382 may provide fixation into a distal fragment of radius 200.

Fixation devices 1322, 1332, 1342, 1352, 1362, 1372, and 1382 may include any device for engaging radius 200, metacarpal 280, and/or carpal bones. Examples of fixation devices 1322, 1332, 1342, 1352, 1362, 1372, and 1382 may include fixation devices 122 and 422. In some embodiments, at least some of fixation devices 1322, 1332, 1342, 1352, 1362, 1372, and 1382 are screws or pegs operable to secure plate 1310 to radius 200, metacarpal 280, and/or carpal bones. Additional examples of fixation devices 1322, 1332, 1342, 1352, 1362, 1372, and 1382 may include locking and non-locking smooth pegs, locking and non-locking cortical screws, and locking and non-locking cannulated compression screws. In some embodiments, fixation devices 1322, 1332, 1342, 1352, 1362, 1372, and 1382 may be similar or the same, such as having similar diameters, threads, and lengths.

Fixation devices 1322, 1332, 1342, 1352, 1362, 1372, and 1382 may be comprised of any suitable material. For example, embodiments may be comprised of a bioabsorbable material, a non-bioabsorbable material, or a combination of both. Examples of materials may include, but are not limited to, metals such as titanium alloy. Some embodiments may also include radio-opaque materials to allow visualization on radiographs.

In some embodiments, openings 1320, 1330, 1340, 1360, 1370, and/or 1380 may be defined by a threaded hole in plate 1310. In these embodiments, fixation devices may have a threaded head portion configured to engage the threaded hole. In some embodiments, fixation devices also include a threaded shaft portion for engaging radius 200, metacarpal 280, and/or carpal bones.

In some embodiments, opening 1350 may be an oblong opening. Teachings of certain embodiments recognize that an oblong opening may aid in positioning a plate on a bone and may be used to provide compression. For example, plate 1310 may be attached to radius 200 by inserting fixation devices 1352 through oblong openings 1350 to engage bone. Plate 1310 may then be repositioned relative to radius 200, allowing fixation device 1352 to move relative to oblong opening 1350. Once plate 1310 is in a suitable position, fixation device 1352 may be tightened to radius 200.

In FIG. 25C, the ends of plate 1310 are tapered such that the thickness of plate 1310 decreases towards the ends. Teachings of certain embodiments recognize that tapered ends may allow plate 1310 to slide into its installed position with less resistance. For example, a tapered end on spanning portion 1312 may allow plate 1310 to push aside flesh while sliding along metacarpal 280.

In FIGS. 25A-25D, plate 1310 is relatively straight such that openings 1320, 1330, 1340, and 1350 are generally coplanar but not necessarily collinear. For example, FIG. 25C shows spanning portion 1312 having twenty degrees of dorsal tilt relative to shaft portion 1314. However, teachings of certain embodiments recognize that other angles may be provided, including, but not limited to, ten to thirty degrees.

In some embodiments, however, openings of plate 1310 may not necessarily be generally coplanar. For example, plate 1310 may have an ulnar bend between spanning portion 1312 and shaft portion 1314. Teachings of certain embodiments recognize that providing an angled plate may reposition metacarpal 280 such that the hand is in a more natural position relative to radius 200.

Figure 26:
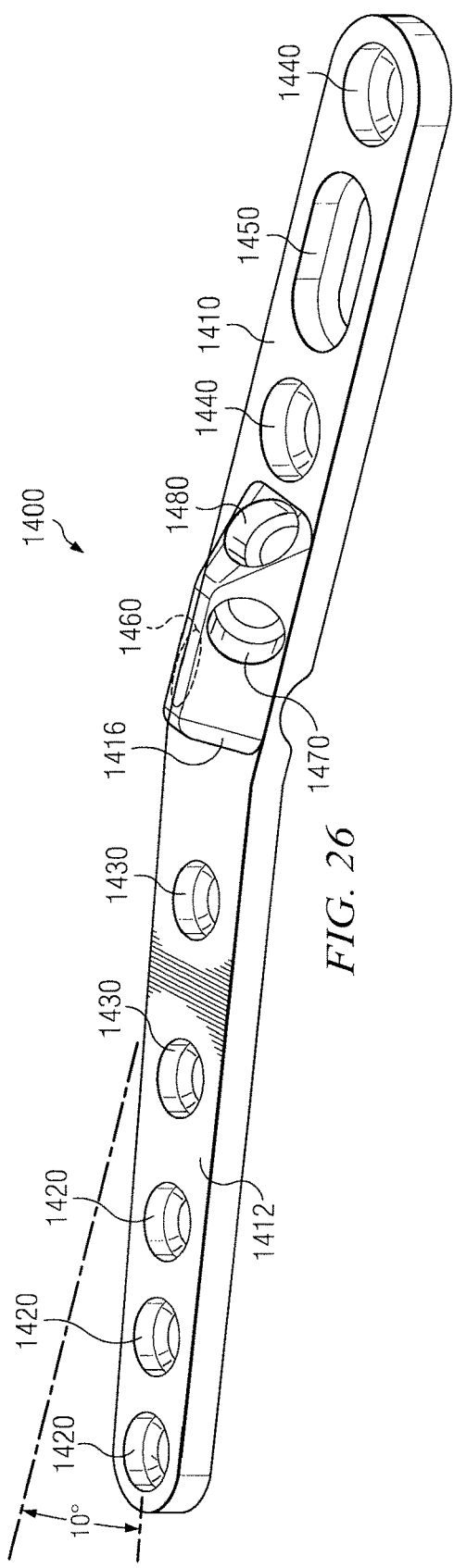
FIG. 26 shows a variation of the bone fusion/fixation/spanning system of FIGS. 25A-25D.

FIG. 26 shows a bone fusion/fixation/spanning system 1400 according to one embodiment. In this example, plate 1410 includes openings 1420, 1430, 1440, 1450, 1460, 1470, and 1480 similar to openings 1320, 1330, 1340, 1350, 1360, 1370, and 1380 of plate 1310.

Unlike plate 1310, plate 1410 provides an ulnar bend between spanning portion 1412 and shaft portion 1414. Teachings of certain embodiments recognize that an ulnar bend may reposition metacarpal 280 such that the hand is in a more natural position relative to radius 200. Teachings of certain embodiments also recognize that providing an ulnar bend may also improve hand strength.

In the illustrated example, spanning portion 1412 has an ulnar bend of ten degrees towards ulna 300. However, teachings of certain embodiments recognize that other angles may be provided, including, but not limited to, ten to fifteen degrees or even five to twenty degrees.

Modifications, additions, or omissions may be made to the systems and apparatuses described herein without departing from the scope of the invention. The components of the systems and apparatuses may be integrated or separated. Moreover, the operations of the systems and apparatuses may be performed by more, fewer, or other components. The methods may include more, fewer, or other steps. Additionally, steps may be performed in any suitable order.

Although several embodiments have been illustrated and described in detail, it will be recognized that substitutions and alterations are possible without departing from the spirit and scope of the present invention, as defined by the appended claims.

What is claimed is:

1. A method for restoring a subchondral bone fragment of a fractured bone, comprising:
   providing a beam proximate to the subchondral bone fragment; and
   rotating the beam about an axis of rotation so as to reposition the subchondral bone fragment, wherein rotating the beam comprises inserting a positioning device through the bone to engage the beam such that the beam rotates about the axis of rotation and repositions the subchondral bone fragment.

2. The method of claim 1, further comprising:
   providing a plate proximate to the fractured bone, the plate having an opening, wherein providing the beam comprises providing the beam through the opening, wherein the axis of rotation is proximate to the opening.

3. The method of claim 1, further comprising:
   providing a plate proximate to the fractured bone, the plate having an opening, wherein inserting the positioning device further comprises inserting the positioning device through the opening.

\* \* \* \* \*